(12) United States Patent
Thuring et al.

(10) Patent No.: US 9,388,175 B2
(45) Date of Patent: Jul. 12, 2016

(54) 2-ANILINE-4-ARYL SUBSTITUTED THIAZOLE DERIVATIVES

(75) Inventors: Johannes Wilhelmus John F. Thuring, Antwerp (BE); Gregor James MacDonald, Ranst (BE); Christopher James Grantham, Ash Aldershot (GB); Theodorus Dinklo, Beerse (BE); Anne Simone Josephine Lesage, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 1954 days.

(21) Appl. No.: 12/063,689

(22) Filed: Feb. 13, 2008

(65) Prior Publication Data

US 2011/0269748 A1 Nov. 3, 2011

Related U.S. Application Data

(63) Continuation of application No. PCT/EP2006/066015, filed on Sep. 5, 2006.

(30) Foreign Application Priority Data

Sep. 13, 2005 (EP) .................................... 05108395

(51) Int. Cl.
| | |
|---|---|
| *C07D 471/04* | (2006.01) |
| *C07D 277/42* | (2006.01) |
| *C07D 417/04* | (2006.01) |
| *C07D 417/12* | (2006.01) |
| *C07D 417/14* | (2006.01) |
| *C07D 513/04* | (2006.01) |

(52) U.S. Cl.
CPC ............ *C07D 471/04* (2013.01); *C07D 277/42* (2013.01); *C07D 417/04* (2013.01); *C07D 417/12* (2013.01); *C07D 417/14* (2013.01); *C07D 513/04* (2013.01)

(58) Field of Classification Search
USPC .................... 514/336, 370; 546/329; 548/190
See application file for complete search history.

(56) References Cited

U.S. PATENT DOCUMENTS

| 3,933,838 A | 1/1976 | Manghisi et al. |
|---|---|---|
| 6,187,797 B1 | 2/2001 | Pruitt et al. |
| 6,569,874 B1 | 5/2003 | Pruitt et al. |
| 2004/0073029 A1 | 4/2004 | Pruitt et al. |

(Continued)

FOREIGN PATENT DOCUMENTS

| EP | 0267986 A | 5/1988 |
|---|---|---|
| EP | 0275312 A | 7/1988 |
| EP | 1205478 A | 5/2002 |

(Continued)

OTHER PUBLICATIONS

Intelihealth, "Alzheimer's disease," online, accessed Jun. 30, 2008, http://www.intelihealth.com/IH/intlh/WSIHW000/8303/9117/195703.html?d=dmtHealthAZ.*
Intelihealth, "Dementia," online, accessed Sep. 22, 2009, http://www.intelihealth.com/IH/ihtIH/WSIHW000/24479/11184.html.*
Intelihealth, "Parkinson's disease," online, accessed Sep. 22, 2009, http://www.intelihealth.com/IH/ihtlH?d=dmtHealthAZ&c=201957.*
Intelihealth, "Schizophrenia" online, accessed Oct. 4, 2011, http://www.intelihealth.com/IH/ihtIH/WSIHW000/8271/8694/188010.html?d=dmtHealthAZ#prevent.*

(Continued)

*Primary Examiner* — Paul Zarek

(57) ABSTRACT

This invention concerns the use of a compound of formula (I)

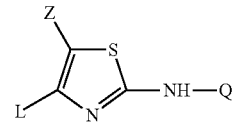

(I)

a N-oxide, a pharmaceutically acceptable addition salt, a quaternary amine and a stereochemically isomeric form thereof, wherein Z is hydrogen, halo, $C_{1-6}$alkyl, $Het^1$, HO—$C_{1-6}$alkyl-, cyano-$C_{1-6}$alkyl-, amino-C(=O)—$C_{1-6}$alkyl-, formylamino-$C_{1-6}$alkyl-, $C_{1-6}$alkyl-C(=O)—NH—$C_{1-6}$alkyl-, mono- or di($C_{1-6}$alkyl)amino-C(=O)—$C_{1-6}$alkyl-, phenyl-$C_{1-6}$alkyl-, or $Het^4$-$C_{1-6}$alkyl-;

Q is phenyl, pyridyl, benzofuranyl, 2,3-dihydro-benzofuranyl, pyrazolyl, isoxazolyl or indazolyl wherein each of said ring systems is optionally being substituted with up to three substituents each independently selected from halo, cyano, $C_{1-6}$alkyl, $C_{1-6}$alkyl-O—, $C_{1-6}$alkylthio, Ar or polyhalo$C_{1-6}$alkyl;

L is phenyl, pyridyl, pyrimidazolyl, 8-Azapyrimidazolyl, pyridazinyl, imidazothiazolyl or furanyl wherein each of said ring systems may optionally be substituted with one or two or more substituents, each substituent independently being selected from halo, hydroxy, amino, cyano, $C_{1-6}$alkyl or $C_{1-6}$alkyl-O—;

$Het^1$ represents morpholinyl; pyrazolyl or imidazolyl;

$Het^4$ represents morpholinyl, pyrazolyl or imidazolyl;

Ar represents phenyl optionally substituted with halo, $C_{1-6}$alkyl, $C_{1-6}$alkyl-O— or polyhalo$C_{1-6}$alkyl; for the manufacture of a medicament for the prevention or the treatment or prophylaxis of psychotic disorders, intellectual impairment disorders or diseases or conditions in which modulation of the α7 nicotinic receptor is beneficial.

4 Claims, No Drawings

(56) References Cited

U.S. PATENT DOCUMENTS

| | | |
|---|---|---|
| 2004/0254236 A1 | 12/2004 | Dong et al. |
| 2005/0004134 A1 | 1/2005 | Tsutsumi et al. |

FOREIGN PATENT DOCUMENTS

| | | |
|---|---|---|
| WO | WO 9603392 A1 | 2/1996 |
| WO | WO 9705131 A | 2/1997 |
| WO | WO 9815543 A | 4/1998 |
| WO | WO 9828282 A2 | 7/1998 |
| WO | WO 9921555 A2 | 5/1999 |
| WO | WO 0164674 A | 9/2001 |
| WO | WO 0174793 A | 10/2001 |
| WO | WO 0224200 A | 3/2002 |
| WO | WO 0242298 A | 5/2002 |
| WO | WO 03015773 A | 2/2003 |
| WO | WO 03062215 A | 7/2003 |
| WO | WO 2004096225 A | 11/2004 |
| WO | WO 2004110350 A | 12/2004 |
| WO | WO 2005070926 A | 8/2005 |

OTHER PUBLICATIONS

Banerjee, Carolin et al., "Cellular Expression of α7 Nicotinic Acetylcholine Receptor Protein in the emporal Cortex in Alzheimer's and Parkinson's Disease—A Stereological Approach", Neurobiology of Disease, (2000), pp. 666-672, vol. 7.

Bickford, Paula C. et al., "Restoration of sensory gating of auditory evoked response by nicotine in fimbria-fornix lesioned rats", Brain Research, (1995), pp. 235-240, vol. 705.

Brown, D.J. et al., "The Chemistry of heterocyclic compounds: Fused Pyrimidines", Book—The Chemistry of Heterocyclic compounds, (1971), pp. 261-304, Chapter IV.

Burghaus, Lothar et al., "Quantitative assessment of nicotinic acetylcholine receptor proteins in the cerebral cortex of Alzheimer patients", Molecular Brain Research, (2000), pp. 385-388, vol. 76.

Dalack, Gregory W. et al., "Nicotine Dependence in Schizophrenia: Clinical Phenomena and Laboratory Findings", Am J Psychiatry, Nov. 1998, pp. 1490-1500, vol. 155:11.

Dani, John A. et al., "Variations in desensitization of nicotinic acetylcholine receptors from hippocampus and midbrain dopamine areas", European Journal of Pharmacology, (2000), pp. 1-38, vol. 393.

Freedman, Robert et al., "Evidence in Postmortem Brain Tissue for Decreased Numbers of Hippocampal Nicotinic Receptors in Schizophrenia", Biol Psychiatry, (1995), pp. 22-33, vol. 38.

Freedman, Robert et al., "Linkage of a neurophysiological deficit in schizophrenia to a chromosome 15 locus", Proc. Natl. Acad. Sci. USA, Jan. 1997, pp. 587-592, vol. 94.

Griffith, Jay M. et al., "Nicotinic Receptor Desensitization and Sensory Gating Deficits in Schizophrenia", Biol Psychiatry, 1998, pp. 98-106, vol. 44.

Guan, Zhi-Zhong et al., "Decreased protein level of nicotinic receptor α7 subunit in the frontal cortex form schizophrenic brain", NeuroReport, Jun. 3, 1999, pp. 1779-1782, vol. 10 No. 8.

Hamill, O. P. et al., "Improved Patch-Clamp Techniques for High-Resolution Current Recording from Cells and Cell-Free Membrane Patches", Pflugers Arch, (1981) pp. 85-100, vol. 391.

Leonard, Sherry et al., "Association of Promoter Variants in the α7 Nicotinic Acetylcholine Receptor Subunit Gene With an Inhibitory Deficit Found in Schizophrenia", Arch Gen Psychiatry, Dec. 2002, pp. 1085-1096, vol. 59.

Marutle, Amelia et al., "Laminar distribution of nicotinic receptor subtypes in cortical regions in schizophrenia", Journal of Chemical Neuroanatomy, (2001), pp. 115-126, vol. 22.

Nagamatsu, Tomohisa et al., "Syntheses of 3-Substituted 1-Methyl-6-phenylpyrimido[5,4-e]-1,2,4-triazine-5,7(1$H$,6$H$)-diones (6-Phenyl Analogs of Toxoflavin) and Their 4-Oxides, and Evaluation of Antimicrobial Activity of Toxoflavins and Their Analogs", Chem. Pharm. Bull., (1993) pp. 362-368, vol. 41(2).

Nagamatsu, Tomohisa et al., "General syntheses of—alkyltoxoflavin and 8-alkylfervenulin derivatives of biological significance by the regioselective alkylation of reumycin derivatives and the rates of transalkylation from 1-alkyltoxoflavins into nucleophiles", J. Chem. Soc., Perkin Trans., 2001, pp. 130-137.

Ray, M.A. et al., "Neuronal nicotinic acetylcholine receptor subunits in autism: An immunohistochemical investigation in the thalamus", Neurobiology of Disease, (2005), pp. 366-377, vol. 19.

Ridley, Diana L. et al., "Differential effects of chronic drug treatment on α3* and α7 nicotinic receptor binding sites, in hippocampal neurons and SH-SY5Y cells", British Journal of Pharmacology, (2001), pp. 1286-1295, vol. 133.

Stetter, Hermann et al., The Catalyzed Nucleophilic Addition of Aldehydes to Electrophilic Double Bonds*, Organic Reactions, (1991), pp. 407-496, vol. 40, Chapter 4.

Virginio, Caterina et al., "Pharmacological properties of rat α7 nicotinic receptors expressed in native and recombinant cell systems", European Journal of Pharmacology, (2002), pp. 153-161, vol. 445.

* cited by examiner

2-ANILINE-4-ARYL SUBSTITUTED THIAZOLE DERIVATIVES

CROSS REFERENCE TO RELATED APPLICATIONS

This application claims priority of the benefits of the filing of Application No. PCT/EP2006/066015 filed Sep. 5, 2006, and Application No. EPO 05/108395.4 filed Sep. 13, 2005. The complete disclosures of the aforementioned related patent applications are hereby incorporated herein by reference for all purposes.

The present invention relates to compounds or pharmaceutically-acceptable salts thereof, processes for preparing them, pharmaceutical compositions containing them and their use in therapy. The invention particularly relates to positive modulators of nicotinic acetylcholine receptors, such positive modulator having the capability to increase the efficacy of nicotinic receptor agonists.

BACKGROUND OF THE INVENTION

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits. Members of the nAChR subunit gene family have been divided into two groups based on their amino acid sequences; one group containing so-called (3 subunits, and a second group containing a subunits. Three kinds of a subunits, $\alpha7$, $\alpha8$ and $\alpha9$, have been shown to form functional receptors when expressed alone and thus are presumed to form homooligomeric pentameric receptors.

An allosteric transition state model of the nAChR has been developed that involves at least a resting state, an activated state and a "desensitized" closed channel state, a process by which receptors become insensitive to the agonist. Different nAChR ligands can stabilize the conformational state of a receptor to which they preferentially bind. For example, the agonists ACh and (−)-nicotine respectively stabilize the active and desensitized states.

Changes of the activity of nicotinic receptors has been implicated in a number of diseases. Some of these, for example myasthenia gravis and ADNFLE (autosomal dominant nocturnal front lobe epilepsy) are associated with reductions in the activity of nicotinic transmission either because of a decrease in receptor number or increased desensitization.

Reductions in nicotinic receptors have also been hypothesized to mediate cognitive deficits seen in diseases such as Alzheimer's disease and schizophrenia.

The effects of nicotine from tobacco are also mediated by nicotinic receptors. and since the effect of nicotine is to stabilize receptors in a desensitized state, an increased activity of nicotinic receptors may reduce the desire to smoke.

Compounds which bind nAChRs have been suggested for the treatment of a range of clinical psychiatric and neurological disorders involving cognitive deficits in attention, alertness, and memory. These may include those that may benefit from selective enhancement in cholinergic transmission such as attention deficit, chronic psychotic disorders, jetlag, selected pain syndromes, and smoking cessation; and those thought to involve reduced cholinergic function such as, neurodegenerative disorders, central inflammatory or autoimmune diseases, brain trauma and cerebral vascular disease.

Modulation of $\alpha7$ nicotinic receptor activity is expected to be beneficial in a number of diseases including Alzheimer's disease, Mild Cognitive Impairment (MCI) and related syndromes, Lewy Body Dementia, vascular dementia, Multiple Sclerosis, post-encephalitic dementias, Parkinson's disease, Huntington's disease, Attention Deficit Hyperactivity Disorder (ADHD), schizophrenia, bipolar mood disorder, schizoaffective disorder, Tourette's syndrome, and brain trauma.

However, treatment with nicotinic receptor agonists which act at the same site as ACh is problematic because ACh not only activates, but also blocks receptor activity through processes which include desensitization and uncompetitive blockade. Furthermore, prolonged activation appears to induce a long-lasting inactivation. Therefore, agonists of ACh can be expected to reduce activity as well as enhance it.

At nicotinic receptors in general, and of particular note at the $\alpha7$-nicotinic receptor, desensitization limits the duration of action of an applied agonist.

DESCRIPTION OF THE INVENTION

We have surprisingly found that certain compounds can increase the efficacy of agonists at nicotinic acetylcholine receptors (nAChR). Compounds having this type of action (hereinafter referred to as "positive modulators") are likely to be particularly useful for treatment of conditions associated with reductions in nicotinic transmission. In a therapeutic setting such compounds could restore normal interneuronal communication without affecting the temporal profile of activation. In addition, positive modulators are not expected to produce long-term inactivation of receptors as may occur at prolonged application of agonists.

Positive nAChR modulators of the present invention useful for treatment or prophylaxis of psychotic disorders, intellectual impairment disorders or diseases or conditions in which modulation of the $\alpha7$ nicotinic receptor is beneficial, in particular for the treatment of a range of disorders that may benefit from selective enhancement in cholinergic transmission such as learning deficit, cognition deficit, attention deficit, chronic psychotic disorders, jetlag, selected pain syndromes, smoking cessation or memory loss, more in particular for the treatment of diseases in which modulation of the $\alpha7$ nicotinic receptor is beneficial, including Mild Cognitive Impairment and related syndromes, vascular dementia, post-encephalitic dementia, Attention deficit Hyperactivity, anxiety, schizophrenia, mania, manic depression, jetlag, bipola mood disorder and schizoaffective disorder.

The present invention concerns 2-aniline-4-aryl thiazole derivatives having positive modulator properties, in particular increasing the efficacy of agonists at the $\alpha7$ nicotinic receptor. The invention further relates to methods for their preparation and pharmaceutical compositions comprising them. The invention also relates to the use of 2-amino-4,5-trisubstituted thiazole derivatives for the manufacture of a medicament for the treatment or prophylaxis of psychotic disorders, intellectual impairment disorders or diseases or conditions in which modulation of the $\alpha7$ nicotinic receptor is beneficial, in particular in the treatment of a range of disorders involving reduced cholinergic function that may benefit from selective enhancement in cholinergic transmission such as learning deficit, cognition deficit, attention deficit or memory loss. In particular in the treatment of Mild Coginitive Impairment, Attention Deficit Hyperactivity Disorder, anxiety, schizophrenia, mania, manic depression or other neurological, degenerative disorders in which there is a loss of cholinergic function, including loss of cholinergic synapses, including jetlag, nicotine addiction and pain. More in particular for the treatment of diseases in which modulation of the α7 nicotinic receptor is beneficial, including Mild Cognitive Impairment and related syndromes, vascular dementia, post-encephalitic dementia, Attention deficit Hyperactivity, anxiety, schizophrenia, mania, manic depression, jetlag, bipolar mood disorder and schizoaffective disorder.

WO 01/64674 describes 2,4-disubstituted thiazole derivatives as cytokine inhibitors, in particular as TNF-α and/or IL-12 inhibitors.

WO 03/015773 describes 2-amino-4,5-trisubstituted thiazole derivatives as cytokine inhibitors, in particular as TNF-α and/or IL-12 inhibitors.

U.S. Pat. No. 6,187,797; U.S. Pat. No. 6,569,874; US patent application US 2004/073029 and PCT publication WO 98/28282 provide phenylthiazoles as factor Xa inhibitors useful as anticoagulant agents for treatment and prevention of thromboembolic disorders.

US patent application US 2004/0254236 provides aminoaryl substituted 5 membered heterocyclic compounds including thiazoles as cytokine inhibitors, in particular P38 inhibitors and their use as anti-inflammatory compounds.

European patent EP 0 267 986 provides 2-amino-4-phenyl-5-thiazoleethanols, as diuretics.

WO 96/03392 provides substituted thiazoles as anti-inflammatory agents that act by inhibiting enzymes in the arachidonic acid/prostaglandin pathway, in particular inhibiting the cyclooxygenase COX-2.

PCT publication WO99/21555 provides thiazoles as selective adenosine A3 receptor antagonists and their use as prophylactic and therapeutic agent for asthma, allergosis or inflammation.

PCT publication WO2004/110350 provides thiazoles with a phenyl substituted NH-group in position 2 as modulators of Aβ that act as BACE inhibitors, and which are accordingly useful in the treatment of amyloidoses.

The compounds of the present invention are distinguishable from the prior art because of their structure and their pharmacological activity as positive modulators of the α7 nicotinic acetylcholine receptor.

The present invention relates to the use of a compound for the manufacture of a medicament for the prevention or the treatment or prophylaxis of psychotic disorders, intellectual impairment disorders or diseases or conditions in which modulation of the α7 nicotinic receptor is beneficial, in particular in the treatment of cognitive deficits seen in diseases such as Alzheimer's disease and schizophrenia, more in particular in the treatment of MCI, ADHD, anxiety, schizophrenia, mania, manic depression or other neurological or psychiatric disorders in which there is loss of cholinergic function, including loss of cholinergic synapses, including jetlag, nicotine addiction and pain; wherein the compound is a compound of formula

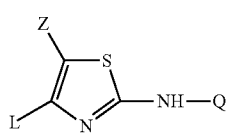

(I)

a N-oxide, a pharmaceutically acceptable addition salt, a quaternary amine and a stereochemically isomeric form thereof, wherein Z is hydrogen, halo; cyano; $C_{1-6}$alkyl; halo$C_{1-6}$alkyl; polyhalo$C_{1-6}$alkyl-; $C_{3-6}$cycloalkyl-C(=O)—; $C_{1-6}$alkyl-C(=O)—; $C_{1-6}$alkyl-O—C(=O)—; $Ar^1$; $Het^1$; $R''R'N—C(=O)—$; $Ar^2$—C(=O)—NH—; $Het^2$-C(=O)—NH—; $C_{3-6}$cycloalkyl-C(=O)—NH—; $C_{1-6}$alkyl-C(=O)—NH—; HO—$C_{1-6}$alkyl-; cyano-$C_{1-6}$alkyl-; amino-$C_{1-6}$alkyl-; formylamino-$C_{1-6}$alkyl-; mono- or di($C_{1-6}$alkyl)amino-$C_{1-6}$alkyl-; $C_{1-6}$alkyl-S(=O)$_2$—NH—$C_{1-6}$alkyl; $C_{1-6}$alkyl-O—C(=O)—NH—$C_{1-6}$alkyl; $R^xR^yN$—C(=O)—$C_{1-6}$alkyl-; $C_{1-6}$alkyl-O—C(=O)—$C_{1-6}$alkyl-; $C_{1-6}$alkyl-S(=O)$_2$—$C_{1-6}$alkyl-; $Ar^3$—S(=O)$_2$—$C_{1-6}$alkyl-; $Het^3$-S(=O)$_2$—$C_{1-6}$alkyl-; $Ar^4$—$C_{1-6}$alkyl-; $Het^4$-$C_{1-6}$alkyl-; $C_{1-6}$alkyl-C(=O)—NH—$C_{1-6}$alkyl-; $Ar^5$—C(=O)—NH—$C_{1-6}$alkyl-; $Het^5$-C(=O)—NH—$C_{1-6}$alkyl-; $C_{3-6}$cycloalkyl-C(=O)—NH—$C_{1-6}$alkyl-; $C_{1-6}$alkyl-O—$C_{1-6}$alkyl-; polyhalo$C_{1-6}$alkyl-O—$C_{1-6}$alkyl-; or amino-$C_{1-6}$alkyl-substituted with $C_{1-4}$alkyl substituted piperidinyl;

Q is phenyl, pyridyl, pyrimidinyl, pyrazinyl, pyrazolyl, pyrrolyl, thienyl, furanyl, benzthiazolyl, 2,3-dihydro-benzofuranyl, benzofuranyl benzoxazolyl, benzimidazolyl, indazolyl, oxazolyl, thiazolyl, isoxazolyl, isothiazolyl, imidazolyl, oxadiazolyl, pyridazinyl, triazolyl, thiadiazolyl or pyrimidazolyl, each of said rings optionally being substituted with up to three substituents each independently selected from halo; hydroxy; cyano; $C_{1-6}$alkyl; $C_{1-6}$alkyl-O—; $C_{1-6}$alkylthio; $C_{1-6}$alkyl-O—C(=O)—; polyhalo$C_{1-6}$alkyl; polyhalo$C_{1-6}$alkyl-O—, amino, mono- or di($C_{1-6}$alkyl)amino, formylamino, $C_{1-6}$alkyl-C(=O)—NH— or Ar;

L is phenyl, piperidinyl, pyrimidinyl, pyrazolyl, triazolyl, pyridyl, pyrimidazolyl, 8-Azapyrimidazolyl, pyridazinyl, imidazothiazolyl, benzodioxolyl, furanyl or 1,4-benzodioxanyl wherein each of said ring systems may optionally be substituted with one or two or more substituents, each substituent independently being selected from halo; hydroxy; amino; cyano; mono- or di($C_{1-6}$alkyl)amino; $C_{1-6}$alkyl; HO—$C_{1-6}$alkyl-; amino-$C_{1-6}$alkyl-; HO—C(=O)—$C_{1-6}$alkyl-; polyhalo$C_{1-6}$alkyl; polyhalo$C_{1-6}$alkyl-O—; $C_{1-6}$alkyl-O—; $C_{1-6}$alkylthio; $C_{1-6}$alkyl-O—C(=O)—; amino-C(=O)—; phenyl-$C_{1-6}$alkyl-O—C(=O)— or $C_{1-6}$alkyl-C(=O)—NH—; or L represents $C_{1-6}$alkyl, $C_{1-6}$alkyl-O—$C_{1-6}$alkyl or $C_{3-6}$cycloalkyl wherein said $C_{1-6}$alkyl, $C_{3-6}$cycloalkyl or $C_{1-6}$alkyl-O—$C_{1-6}$alkyl is optionally substituted with one or where possible two or more halo substituents;

Ar represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)—, polyhalo$C_{1-6}$alkyl-O— or polyhalo$C_{1-6}$alkyl;

$Ar^1$ represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)—, polyhalo$C_{1-6}$alkyl-O— or polyhalo$C_{1-6}$alkyl;

$Ar^2$ represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)—, polyhalo$C_{1-6}$alkyl-O— or polyhalo$C_{1-6}$alkyl;

$Ar^3$ represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)—, polyhalo$C_{1-6}$alkyl-O— or polyhalo$C_{1-6}$alkyl;

$Ar^4$ represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)—, polyhalo$C_{1-6}$alkyl-O— or polyhalo$C_{1-6}$alkyl;

$Ar^5$ and $Ar^6$ each independently represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)—, polyhalo$C_{1-6}$alkyl-O— or polyhalo $C_{1-6}$alkyl;

$Het^1$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl wherein each of said ring systems may optionally be substituted with up to 3 substituents, each substituent independently being selected from halo, hydroxy, amino, cyano or $C_{1-6}$alkyl;

$Het^2$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl wherein each of said ring systems may optionally be substituted with up to 3 substituents, each substituent independently being selected from halo, hydroxy, amino, cyano or $C_{1-6}$alkyl;

$Het^3$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl wherein each of said ring systems may optionally be substituted with up to 3 substituents, each substituent independently being selected from halo, hydroxy, amino, cyano or $C_{1-6}$alkyl;

$Het^4$ represents piperidinyl, piperazinyl, pyrrolidinyl, morpholinyl, imidazolyl, oxazolyl, oxadiazolyl, thiazolyl, isoxazolyl, isothiazolyl, thiomorpholinyl or pyrazolyl wherein each of said ring systems may optionally be substituted with up to 3 substituents, each substituent independently being selected from halo, hydroxy, amino, cyano or $C_{1-6}$alkyl;

$Het^5$ and $Het^6$ each independently represents piperidinyl, piperazinyl, pyridyl, pyrrolidinyl, morpholinyl, imidazolyl, oxazolyl, oxadiazolyl, thiazolyl, isoxazolyl, isothiazolyl, thiomorpholinyl or pyrazolyl wherein each of said ring systems may optionally be substituted with up to 3 substituents, each substituent independently being selected from halo, hydroxy, amino, cyano or $C_{1-6}$alkyl;

$R^u$ and $R^v$ each independently represent hydrogen, $C_{1-6}$alkyl, $Ar^6$, $Het^6$, $C_{3-6}$cycloalkyl, $C_{1-6}$alkyl-O—$C_{1-6}$alkyl or $R^u$ and $R^v$ taken together with the N atom to which they are attached form a 5 or 6 membered heterocycle selected from pyrrolidinyl, piperidinyl, thiomorpholinyl and morpholinyl wherein each of said ring systems may optionally be substituted with up to 3 substituents, each substituent independently being selected from halo, hydroxy, amino, cyano or $C_{1-6}$alkyl;

$R^x$ and $R^y$ each independently represent hydrogen, $C_{1-6}$alkyl, $Ar^6$, $Het^6$, $C_{3-6}$cycloalkyl, $C_{1-6}$alkyl-O—$C_{1-6}$alkyl or $R^x$ and $R^y$ taken together with the N atom to which they are attached form a 5 or 6 membered heterocycle selected from pyrrolidinyl, piperidinyl, thiomorpholinyl and morpholinyl wherein each of said ring systems may optionally be substituted with up to 3 substituents, each substituent independently being selected from halo, hydroxy, amino, cyano or $C_{1-6}$alkyl.

The present invention also relates to a compound of formula

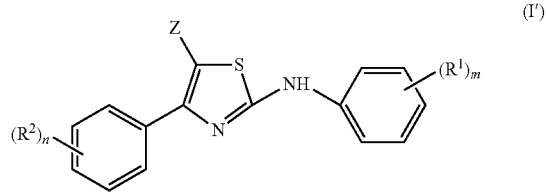

(I')

a N-oxide, a pharmaceutically acceptable addition salt, a quaternary amine and a stereochemically isomeric form thereof, wherein n is 0, 1, 2, 3 or 4;

m is 0, 1, 2, 3 or 4;

$R^1$ each independently represents halo; hydroxy; cyano; $C_{1-6}$alkyl; $C_{1-6}$alkyl-O—; $C_{1-6}$alkylthio; $C_{1-6}$alkyl-O—C(=O)—; polyhalo$C_{1-6}$alkyl-O— or polyhalo$C_{1-6}$alkyl-;

$R^2$ each independently represents halo; hydroxy; amino; cyano; mono- or di($C_{1-6}$alkyl)amino; $C_{1-6}$alkyl; HO—$C_{1-6}$alkyl-; amino-$C_{1-6}$alkyl-; HO—C(=O)—$C_{1-6}$alkyl-; polyhalo$C_{1-6}$alkyl; $C_{1-6}$alkyl-O—; $C_{1-6}$alkylthio; $C_{1-6}$alkyl-O—C(=O)—; amino-C(=O)—; polyhalo-$C_{1-6}$alkyl-O— or $C_{1-6}$alkyl-C(=O)—NH—;

Z is $Het^1$; $C_{1-6}$alkyloxy-C(=O)—; HO—$C_{1-4}$alkyl-, $C_{1-6}$alkyl-C(=O)—NH—$C_{1-4}$alkyl-; $C_{3-6}$cycloalkyl-C(=O)—NH—$C_{1-4}$alkyl-; cyano-$C_{1-4}$alkyl-; formylamino-$C_{1-4}$alkyl-; $Het^4$-$C_{1-4}$alkyl-; $Ar^4$—$C_{1-4}$alkyl-; $R^xR^yN$—C(=O)—$C_{1-4}$alkyl-; halo; $R^uR^vN$—C(=O)—; $C_{1-6}$alkyl-O—$C_{1-6}$alkyl or Z represents $C_{1-6}$alkyloxy-C(=O)—$C_{2-4}$alkyl-;

$Het^1$ represents morpholinyl, thiomorpholinyl, imidazolyl, pyrrolidinyl or pyrazolyl;

$Het^4$ represents morpholinyl, thiomorpholinyl, imidazolyl, pyrrolidinyl or pyrazolyl;

$Het^6$ represents pyridyl;

$Ar^4$ represents phenyl optionally substituted with halo, $C_{1-6}$alkyl, $C_{1-6}$alkyloxy, polyhalo$C_{1-6}$alkyloxy or polyhalo$C_{1-6}$alkyl;

$R^x$ and $R^y$ each independently represent hydrogen, $C_{1-6}$alkyl or $R^x$ and $R^y$ taken together with the N atom to which they are attached form a 5 or 6 membered heterocycle selected from pyrrolidinyl, thiomorpholinyl, piperidinyl or morpholinyl;

$R^u$ and $R^v$ each independently represent hydrogen, $C_{1-6}$alkyl or $Het^6$ or $R^u$ and $R^v$ taken together with the N atom to which they are attached form a 5 or 6 membered heterocycle selected from pyrrolidinyl, thiomorpholinyl, piperidinyl or morpholinyl;

provided that;

Z is other than ethoxycarbonyl-;

the compound is other than 4-phenyl-2-(phenylamino)-5-thiazoleacetonitrile [406470-24-4]; 5-[2-(4-morpholinyl)ethyl]-N,4-diphenyl-2-Thiazolamine [754921-77-2]; 5-Thiazolepropanoic acid, 2-[(4-bromophenyl)amino]-4-(4-methoxyphenyl)-, methyl ester (9CI) [571149-21-8]; 5-Thiazolepropanoic acid, 2-[(4-chlorophenyl)amino]-4-(4-methoxyphenyl)-, methyl ester (9CI) [406471-23-6]; 5-Thiazolepropanoic acid, 4-(4-methoxyphenyl)-2-[(4-methoxyphenyl)amino]-, methyl ester (9CI) [406469-54-3]; 5-Thiazolepropanoic acid, 4-(4-methoxyphenyl)-2-[(2,3,4-trifluorophenyl)amino]-, methyl ester (9CI) [402768-12-1]; 5-Thiazolepropanoic acid, 4-(4-methoxyphenyl)-2-(phenylamino)-, methyl ester (9Cl) [370840-06-5]; 5-Thiazoleethanol, 4-(4-chlorophenyl)-2-(phenylamino)-(9Cl) [117612-81-4] or 4-(4-fluorophenyl)-5-[2-(4-morpholinyl)ethyl]-N-phenyl-2-Thiazolamine [773792-81-7].

As well as to use of a compound of formula (I') for the manufacture of a medicament for the prevention or the treatment or prophylaxis of psychotic disorders, intellectual impairment disorders or diseases or conditions in which modulation of the α7 nicotinic receptor is beneficial, in particular in the treatment of cognitive deficits seen in diseases such as Alzheimer's disease and schizophrenia, more in particular in the treatment of Mild Cognitive Impairment, Attention Deficit Hyperactivity Disorder, anxiety, schizophrenia, mania, manic depression or other neurological, degenerative disorders in which there is a loss of cholinergic function, including loss of cholinergic synapses, including jetlag, nicotine addiction and pain. Even more in particular for the treatment of diseases in which modulation of the α7 nicotinic receptor is beneficial, including Mild Cognitive Impairment and related syndromes, vascular dementia, post-encephalitic dementia, Attention deficit Hyperactivity, anxiety, schizophrenia, mania, manic depression, jetlag, bipolar mood disorder and schizoaffective disorder.

In a further object, this invention provides the compounds of formula

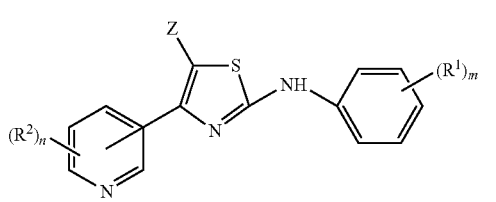

(I'')

a N-oxide, a pharmaceutically acceptable addition salt, a quaternary amine and a stereochemically isomeric form thereof, wherein n is 0, 1, 2, 3 or 4;
m is 0, 1, 2, 3 or 4;
$R^1$ each independently represents halo; hydroxy; $C_{1-6}$alkyl; $C_{1-6}$alkyloxy; $C_{1-6}$alkylthio; $C_{1-6}$alkyloxycarbonyl; polyhalo$C_{1-6}$alkyl-O— or polyhalo$C_{1-6}$alkyl;
$R^2$ each independently represents halo; hydroxy; amino; cyano; mono- or di($C_{1-6}$alkyl)amino; $C_{1-6}$alkyl; HO—$C_{1-6}$alkyl-; amino-$C_{1-6}$alkyl-; HO—C(=O)—$C_{1-6}$alkyl-; polyhalo$C_{1-6}$alkyl; $C_{1-6}$alkyl-O—; $C_{1-6}$alkylthio; $C_{1-6}$alkyl-O—C(=O)—; aminocarbonyl; polyhalo $C_{1-6}$alkyl-O— or $C_{1-6}$alkyl-C(=O)—NH—;
Z is $Het^1$; $C_{1-6}$alkyloxy-C(=O)—; HO—$C_{1-4}$alkyl-; $C_{1-6}$alkyl-C(=O)—NH—$C_{1-4}$alkyl-; $C_{3-6}$cycloalkyl-C(=O)—NH—$C_{1-4}$alkyl-; cyano-$C_{1-4}$alkyl-; formylamino-$C_{1-4}$alkyl-; $Het^4$-$C_{1-4}$alkyl-; $Ar^4$—$C_{1-4}$alkyl-; $R^xR^yN$—C(=O)—$C_{1-4}$alkyl-; halo; halo$C_{1-6}$alkyl; $C_{1-6}$alkyl; $C_{1-6}$alkyl-O—$C_{1-6}$alkyl; mono- or di($C_{1-4}$alkyl)amino-$C_{1-6}$alkyl; $C_{1-6}$alkyl-O—C(=O)—NH—$C_{1-6}$alkyl; $C_{1-6}$alkyl-S(=O)$_2$—NH—$C_{1-6}$alkyl; $Het^5$-C(=O)—NH—$C_{1-6}$alkyl; $Ar^5$—C(=O)—NH—$C_{1-6}$alkyl or Z represents $C_{1-6}$alkyloxy-C(=O)—$C_{2-4}$alkyl-; in particular Z is $Het^1$; $C_{1-6}$alkyl-C(=O)—NH—$C_{1-4}$alkyl-; $C_{3-6}$cycloalkyl-C(=O)—NH—$C_{1-4}$alkyl-; cyano-$C_{1-4}$alkyl-; formylamino-$C_{1-4}$alkyl-; $Het^4$-$C_{1-4}$alkyl-; $Ar^4$—$C_{1-4}$alkyl-; $R^xR^yN$—C(=O)—$C_{1-4}$alkyl-; $C_{1-6}$alkyl-O—$C_{1-6}$alkyl; $C_{1-6}$alkyl-O—C(=O)—NH—$C_{1-6}$alkyl; $C_{1-6}$alkyl-S(=O)$_2$—NH—$C_{1-6}$alkyl; $Het^5$-C(=O)—NH—$C_{1-6}$alkyl; $Ar^5$—C(=O)—NH—$C_{1-6}$alkyl or Z represents $C_{1-6}$alkyloxy-C(=O)—$C_{2-4}$alkyl-;

$Het^1$ represents morpholinyl, thiomorpholinyl, imidazolyl, pyrrolidinyl or pyrazolyl;
$Het^4$ represents morpholinyl, thiomorpholinyl, imidazolyl, pyrrolidinyl or pyrazolyl;
$Het^5$ represents isoxazolyl or pyridyl wherein each of said ring systems may optionally be substituted with up to 3 substituents, each substituent independently being selected from halo or $C_{1-6}$alkyl;
$Ar^4$ represents phenyl optionally substituted with halo, $C_{1-6}$alkyl, $C_{1-6}$alkyloxy, polyhalo$C_{1-6}$alkyloxy or polyhalo$C_{1-6}$alkyl;
$Ar^5$ represents phenyl optionally substituted with halo, $C_{1-6}$alkyl, $C_{1-6}$alkyloxy, polyhalo$C_{1-6}$alkyloxy or polyhalo$C_{1-6}$alkyl;
$R^x$ and $R^y$ each independently represent hydrogen, $C_{1-6}$alkyl, $C_{1-6}$alkyl-O—$C_{1-6}$alkyl or $R^x$ and $R^y$ taken together with the N atom to which they are attached form a 5 or 6 membered heterocycle selected from pyrrolidinyl, thiomorpholinyl, piperidinyl or morpholinyl;
provided that;
the compound is other than 5-Thiazolemethanamine, 2-[[4-fluoro-3-(trifluoromethyl)phenyl]amino]-N,N-dimethyl-4-(3-pyridinyl)-(9Cl) [499984-77-9];
the compound is other than 4-thiazolepropanamine, N-methyl-2-(phenylamino)-5-(2-pyridinyl)-[743384-14-7]; or
when the pyridyl ring is attached at position 3 or 4 to the thiazole ring, Z is other than hydroxyl-$C_{1-2}$alkyl, halo, methyl, ethoxycarbonyl-, methoxycarbonyl-, dimethylaminomethyl-, dimethylaminoethyl-, ethylaminomethyl- or morpholinyl-$C_{1-2}$alkyl.

As well as to the use of a compound of formula (I'') for the manufacture of a medicament for the prevention or the treatment or prophylaxis of psychotic disorders, intellectual impairment disorders or diseases or conditions in which modulation of the α7 nicotinic receptor is beneficial, in particular in the treatment of cognitive deficits seen in diseases such as Alzheimer's disease and schizophrenia, more in particular in the treatment of MCI, ADHD, anxiety, schizophrenia, mania, manic depression or other neurological or psychiatric disorders in which there is loss of cholinergic function, including loss of cholinergic synapses, including jetlag, nicotine addiction and pain. Even more in particular for the treatment of diseases in which modulation of the α7 nicotinic receptor is beneficial, including Mild Cognitive Impairment and related syndromes, vascular dementia, post-encephalitic dementia, Attention deficit Hyperactivity, anxiety, schizophrenia, mania, manic depression, jetlag, bipolar mood disorder and schizoaffective disorder.

In a further object, this invention provides the compounds of formula

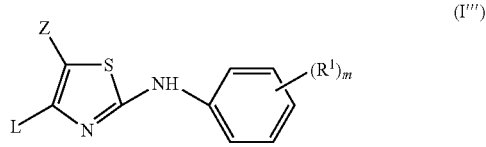

(I''')

a N-oxide, a pharmaceutically acceptable addition salt, a quaternary amine and a stereochemically isomeric form thereof, wherein m is 0, 1, 2, 3 or 4; in particular m is 0, 1 or 2;

$R^1$ each independently represents halo; hydroxy; $C_{1-6}$alkyl; $C_{1-6}$alkyloxy; $C_{1-6}$alkylthio; $C_{1-6}$alkyloxycarbonyl; polyhalo$C_{1-6}$alkyl-O— or polyhalo$C_{1-6}$alkyl; in particular $R^1$ each independently represents halo; $C_{1-6}$alkyloxy- or polyhalo$C_{1-6}$alkyl; more in particular $R^1$ each independently represents chloro, methoxy or trifluoromethyl;

Z is $C_{1-6}$alkyloxy-C(=O)—; HO—$C_{1-4}$alkyl; $C_{1-6}$alkyl-C(=O)—; $C_{3-6}$cycloalkyl-C(=O)— or $C_{1-6}$alkyloxy-C(=O)—$C_{1-6}$alkyl; in particular Z is $C_{1-6}$alkyloxy-C(=O)—; HO—$C_{1-4}$alkyl or $C_{1-6}$alkyl-C(=O)—; more in particular Z is ethoxycarbonyl; methoxycarbonyl; HO-methyl; or methyl-C(=O)—; and L is $C_{1-6}$alkyl; $C_{1-6}$alkyl-O—$C_{1-6}$alkyl or $C_{3-6}$cycloalkyl wherein said $C_{1-6}$alkyl; $C_{1-6}$alkyl-O—$C_{1-6}$alkyl or $C_{3-6}$cycloalkyl is optionally substituted with one or where possible two or more halo substituents; in particular L is methyl; propyl; isopropyl; methoxymethyl; methoxyethyl; difluoromethyl or trifluoromethyl.

As well as to the use of a compound of formula (I''') for the manufacture of a medicament for the prevention or the treatment or prophylaxis of psychotic disorders, intellectual impairment disorders or diseases or conditions in which modulation of the α7 nicotinic receptor is beneficial, in particular in the treatment of cognitive deficits seen in diseases such as Alzheimer's disease and schizophrenia, more in particular in the treatment of MCI, ADHD, anxiety, schizophrenia, mania, manic depression or other neurological or psychiatric disorders in which there is loss of cholinergic function, including loss of cholinergic synapses, including jetlag, nicotine addiction and pain. Even more in particular for the treatment of diseases in which modulation of the α7 nicotinic receptor is beneficial, including Mild Cognitive Impairment and related syndromes, vascular dementia, post-encephalitic dementia, Attention deficit Hyperactivity, anxiety, schizophrenia, mania, manic depression, jetlag, bipolar mood disorder and schizoaffective disorder.

As used hereinabove or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{3-6}$cycloalkyl is generic to cyclopropyl, cyclobutyl, cyclopentyl and cyclohexyl.

The L or Q radical as described above for the compounds of formula (I) may be attached to the remainder of the molecule of formula (I) through any ring carbon or heteroatom as appropriate. For example, when Q is pyridyl, it may be 2-pyridyl, 3-pyridyl or 4-pyridyl.

Lines drawn into ring systems indicate that the bond may be attached to any suitable ring atom. When the ring system is a bicyclic ring system, the bond may be attached to any suitable ring atom of either of the two rings.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example methyl with one or more fluoro atoms, for example, difluoromethyl or trifluoromethyl, 1,1-difluoro-ethyl and the like. In case more than one halogen atoms are attached to an alkyl group within the definition of polyhalo$C_{1-4}$alkyl or polyhalo$C_{1-6}$alkyl, they may be the same or different.

The heterocycles as mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

Further, the heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzothiazolyl, it may be 2-benzothiazolyl, 4-benzothiazolyl, 5-benzothiazolyl, 6-benzothiazolyl and 7-benzothiazolyl.

When any variable occurs more than one time in any constituent, each definition is independent.

It will be appreciated that some of the compounds of formula (I), (I'), (I'') or (I''') and their N-oxides, addition salts, quaternary amines and stereochemically isomeric forms may contain one or more centers of chirality and exist as stereochemically isomeric forms.

The term "stereochemically isomeric forms" as used hereinbefore or hereinafter defines all the possible stereoisomeric forms which the compounds of formula (I), (I'), (I'') or (I''') and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I), (I'), (I'') or (I''') and their N-oxides, salts, solvates, quaternary amines substantially free, i.e. associated with less than 10%, preferably less than 5%, in particular less than 2% and most preferably less than 1% of the other isomers. Stereochemically isomeric forms of the compounds of formula (I), (I'), (I'') or (I''') are obviously intended to be embraced within the scope of this invention.

For therapeutic use, salts of the compounds of formula (I), (I'), (I'') or (I''') are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of formula (I), (I'), (I'') or (I''') are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I), (I'), (I") or (I''') containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term addition salt as used hereinabove also comprises the solvates which the compounds of formula (I), (I'), (I") or (I''') as well as the salts thereof, are able to form. Such solvates are for example hydrates, alcoholates and the like.

The term "quaternary amine" as used hereinbefore defines the quaternary ammonium salts which the compounds of formula (I), (I'), (I") or (I''') are able to form by reaction between a basic nitrogen of a compound of formula (I), (I'), (I") or (I''') and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include for example chloro, bromo, iodo, trifluoroacetate and acetate. The counterion of choice can be made using ion exchange resin columns.

The N-oxide forms of the present compounds are meant to comprise the compounds of formula (I), (I'), (I") or (I''') wherein one or several tertiary nitrogen atoms are oxidized to the so-called N-oxide.

Some of the compounds of formula (I), (I'), (I") or (I''') may also exist in their tautomeric form. Such forms although not explicitly indicated in the above formula are intended to be included within the scope of the present invention.

A first group of compounds are those compounds of formula (I) wherein one or more of the following restrictions apply;

(i) Z is hydrogen, halo; $C_{1-6}$alkyl; polyhalo$C_{1-6}$alkyl-; $C_{3-6}$cycloalkyl-C(=O)—; $C_{1-6}$alkyl-C(=O)—; amino-C(=O)—; cyano; $C_{1-6}$alkyl-O—C(=O)—; $Ar^1$; $Het^1$; HO—$C_{1-6}$alkyl-; cyano-$C_{1-6}$alkyl-; amino-$C_{1-6}$alkyl-; mono- or di($C_{1-6}$alkyl)amino-$C_{1-6}$alkyl-; $R^xR^yN$—C(=O)—$C_{1-6}$alkyl-; formylamino-$C_{1-6}$alkyl-; $C_{1-6}$alkyl-O—C(=O)—$C_{1-6}$alkyl-; $C_{1-6}$alkyl-C(=O)—NH—$C_{1-6}$alkyl-; $Ar^3$—C(=O)—NH—; $Het^3$-C(=O)—NH—; $C_{3-6}$cycloalkyl-C(=O)—NH—$C_{1-6}$alkyl-; $C_{1-6}$alkyl-O—$C_{1-6}$alkyl-; $Ar^4$—$C_{1-6}$alkyl-; $Het^4$-$C_{1-6}$alkyl-; polyhalo$C_{1-6}$alkyl-O—$C_{1-6}$alkyl-; or amino-$C_{1-6}$alkyl-substituted with $C_{1-4}$alkyl substituted piperidinyl; in particular Z is halo; polyhalo$C_{1-6}$alkyl-; $C_{3-6}$cycloalkyl-C(=O)—; $C_{1-6}$alkyl-C(=O)—; amino-C(=O)—; cyano; $C_{1-6}$alkyl-O—C(=O)—; $Ar^1$; $Het^1$; HO—$C_{1-6}$alkyl-; cyano-$C_{1-6}$alkyl-; amino-$C_{1-6}$alkyl-; mono- or di($C_{1-6}$alkyl)amino-$C_{1-6}$alkyl-; $R^xR^yN$—C(=O)—$C_{1-6}$alkyl-; formylamino-$C_{1-6}$alkyl-; $C_{1-6}$alkyl-O—C(=O)—$C_{1-6}$alkyl-; $C_{1-6}$alkyl-C(=O)—NH—$C_{1-6}$alkyl-; $Ar^3$—C(=O)—NH—; $Het^3$-C(=O)—NH—; $C_{3-6}$cycloalkyl-C(=O)—NH—$C_{1-6}$alkyl-; $C_{1-6}$alkyl-O—$C_{1-6}$alkyl-; $Ar^4$—$C_{1-6}$alkyl-; $Het^4$-$C_{1-6}$alkyl-; polyhalo$C_{1-6}$alkyl-O—$C_{1-6}$alkyl-; or amino-$C_{1-6}$alkyl-substituted with $C_{1-4}$alkyl substituted piperidinyl;

(ii) Q is phenyl, pyridyl, pyrimidinyl, pyrazinyl, pyrazolyl, pyrrolyl, thienyl, furanyl, benzthiazolyl, 2,3-dihydrobenzofuranyl, benzofuranyl benzoxazolyl, benzimidazolyl, indazolyl, oxazolyl, thiazolyl, isoxazolyl, isothiazolyl, imidazolyl, oxadiazolyl, pyridazinyl, triazolyl, thiadiazolyl or pyrimidazolyl, each of said rings optionally being substituted with up to three substituents each independently selected from halo; hydroxy; cyano; $C_{1-6}$alkyl; $C_{1-6}$alkyl-O—; $C_{1-6}$alkylthio; $C_{1-6}$alkyl-O—C(=O)—; polyhalo$C_{1-6}$alkyl-O—; polyhalo$C_{1-6}$alkyl or Ar;

(iii) L is phenyl, pyrimidinyl, pyrazolyl, triazolyl, pyridyl, pyrimidazolyl, piperidinyl, 8-Azapyrimidazolyl, pyridazinyl, imidazothiazolyl, benzodioxolyl, 1,4-benzodioxanyl, or furanyl wherein each of said ring systems may optionally be substituted with one or two or more substituents, each substituent independently being selected from halo; hydroxy; amino; cyano; mono- or di($C_{1-6}$alkyl)amino; $C_{1-6}$alkyl; HO—$C_{1-6}$alkyl-; amino-$C_{1-6}$alkyl-; HO—C(=O)—$C_{1-6}$alkyl-; polyhalo $C_{1-6}$alkyl; polyhalo$C_{1-6}$alkyl-O—; $C_{1-6}$alkyl-O—; $C_{1-6}$alkylthio; $C_{1-6}$alkyl-O—C(=O)—; amino-C(=O) or $C_{1-6}$alkyl-C(=O)—NH—;

(iv) Ar represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)—, polyhalo$C_{1-6}$alkyl-O— or polyhalo $C_{1-6}$alkyl;

(v) $Ar^1$ represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)— or polyhalo$C_{1-6}$alkyl-O— or polyhalo $C_{1-6}$alkyl;

(vi) $Ar^3$ represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)— or polyhalo$C_{1-6}$alkyl-O— or polyhalo $C_{1-6}$alkyl;

(vii) $Ar^4$ represents phenyl optionally substituted one or where possible two, three or more substituents each independently selected from halo, hydroxy, cyano, $C_{1-6}$alkyl, $C_{1-6}$alkyl-O—, $C_{1-6}$alkylthio, $C_{1-6}$alkyl-O—C(=O)— or polyhalo$C_{1-6}$alkyl-O— or polyhalo $C_{1-6}$alkyl;

(viii) $Het^1$ represents piperidinyl, piperazinyl, morpholinyl, imidazolyl, oxazolyl, oxadiazolyl, thiazolyl, isoxazolyl, isothiazolyl, thiomorpholinyl or pyrazolyl wherein each of said ring systems may optionally be substituted with up to 3 substituents, each substituent independently being selected from halo, hydroxy, amino, cyano or $C_{1-6}$alkyl;

(ix) $Het^3$ represents piperidinyl, piperazinyl, morpholinyl, imidazolyl, oxazolyl, oxadiazolyl, thiazolyl, isoxazolyl, isothiazolyl, thiomorpholinyl or pyrazolyl wherein each of said ring systems may optionally be substituted with up to 3 substituents, each substituent independently being selected from halo, hydroxy, amino, cyano or $C_{1-6}$alkyl;
(x) $Het^4$ represents piperidinyl, piperazinyl, morpholinyl, imidazolyl, oxazolyl, oxadiazolyl, thiazolyl, isoxazolyl, isothiazolyl, thiomorpholinyl or pyrazolyl wherein each of said ring systems may optionally be substituted with up to 3 substituents, each substituent independently being selected from halo, hydroxy, amino, cyano or $C_{1-6}$alkyl;
(xi) $R^x$ and $R^y$ each independently represent hydrogen, $C_{1-6}$alkyl or $R^x$ and $R^y$ taken together with the N atom to which they are attached form a 5 or 6 membered heterocycle selected from pyrrolidinyl, imidazolidinyl, pyrazolidinyl, piperidinyl, thiomorpholinyl and morpholinyl wherein each of said ring systems may optionally be substituted with up to 3 substituents, each substituent independently being selected from halo, hydroxy, amino, cyano or $C_{1-6}$alkyl.

An interesting embodiment of the present invention concerns those compounds of formula (I) wherein one or more of the following restrictions apply:
(i) Z is hydrogen, halo, $C_{1-6}$alkyl, $C_{1-6}$alkyl-C(=O)—, $C_{1-6}$alkyl-O—C(=O)—, $Ar^1$, $Het^1$, $R^uR^vN$—C(=O)—, HO—$C_{1-6}$alkyl-, cyano-$C_{1-6}$alkyl-, halo $C_{1-6}$alkyl, amino-$C_{1-6}$alkyl, $Het^2$-C(=O)—NH—, formylamino-$C_{1-6}$alkyl-, mono- or di($C_{1-6}$alkyl)amino-$C_{1-6}$alkyl-, $R^xR^yN$—C(=O)—$C_{1-6}$alkyl-, $C_{1-6}$alkyl-O—C(=O)—$C_{1-6}$alkyl-, $Ar^4$—$C_{1-6}$alkyl-, $Het^4$-$C_{1-6}$alkyl-, $C_{1-6}$alkyl-C(=O)—NH—$C_{1-6}$alkyl-, $Ar^5$—C(=O)—NH—$C_{1-6}$alkyl-, $Het^5$-C(=O)—NH—$C_{1-6}$alkyl-, $C_{1-6}$alkyl-S(=O)$_2$—NH—$C_{1-6}$alkyl-, $C_{1-6}$alkyl-O—C(=O)—NH—$C_{1-6}$alkyl or $C_{1-6}$alkyl-O—$C_{1-6}$alkyl-; in particular Z is hydrogen, halo, $C_{1-6}$alkyl, $Het^1$, HO—$C_{1-6}$alkyl-, cyano-$C_{1-6}$alkyl-, amino-C(=O)—$C_{1-6}$alkyl-, formylamino-$C_{1-6}$alkyl-, $C_{1-6}$alkyl-C(=O)—NH—$C_{1-6}$alkyl-, mono- or di($C_{1-6}$alkyl)amino-C(=O)—$C_{1-6}$alkyl-, phenyl-$C_{1-6}$alkyl-, or $Het^4$-$C_{1-6}$alkyl-; more in particular Z is halo, $Het^1$, HO—$C_{1-6}$alkyl-, cyano-$C_{1-6}$alkyl-, amino-C(=O)—$C_{1-6}$alkyl-, formylamino-$C_{1-6}$alkyl-, $C_{1-6}$alkyl-C(=O)—NH—$C_{1-6}$alkyl-, mono- or di($C_{1-6}$alkyl)amino-C(=O)—$C_{1-6}$alkyl-, phenyl-$C_{1-6}$alkyl-, or $Het^4$-$C_{1-6}$alkyl-;
(ii) Q is phenyl; pyridyl; benzofuranyl; 2,3-dihydro-benzofuranyl; pyrazolyl; benzimidazolyl; isoxazolyl or indazolyl wherein each of said ring systems is optionally being substituted with up to three substituents each independently selected from halo, cyano, $C_{1-6}$alkyl, $C_{1-6}$alkyl-O—, $C_{1-6}$alkylthio, $C_{1-6}$alkyl-O—C(=O)—, Ar or polyhalo$C_{1-6}$alkyl; in particular Q is phenyl; pyridyl; benzofuranyl; 2,3-dihydro-benzofuranyl; pyrazolyl; isoxazolyl or indazolyl wherein each of said ring systems is optionally being substituted with up to three substituents each independently selected from halo, cyano, $C_{1-6}$alkyl, $C_{1-6}$alkyl-O—, $C_{1-6}$alkylthio, Ar or polyhalo$C_{1-6}$alkyl;
(iii) L represents $C_{1-6}$alkyl, $C_{1-6}$alkyl-O—$C_{1-6}$alkyl or $C_{3-6}$cycloalkyl, wherein said $C_{1-6}$alkyl, $C_{1-6}$alkyl-O—$C_{1-6}$alkyl or $C_{3-6}$cycloalkyl is optionally substituted with one or where possible two or more halo substituents; or L is phenyl, pyridyl, piperidinyl, pyrimidinyl, 1,4-benzodioxanyl, pyrimidazolyl, 8-Azapyrimidazolyl, pyridazinyl, imidazothiazolyl or furanyl wherein each of said ring systems may optionally be substituted with one or two or more substituents, each substituent independently being selected from halo, hydroxy, amino, cyano, $C_{1-6}$alkyl, phenyl-$C_{1-6}$alkyl-O—C(=O)— or $C_{1-6}$alkyl-O—; in particular L is phenyl, pyridyl, pyrimidazolyl, 8-Azapyrimidazolyl, pyridazinyl, imidazothiazolyl or furanyl wherein each of said ring systems may optionally be substituted with one or two or more substituents, each substituent independently being selected from halo, hydroxy, amino, cyano, $C_{1-6}$alkyl or $C_{1-6}$alkyl-O—;
(iv) $Het^1$ represents morpholinyl; pyrazolyl or imidazolyl;
(v) $Het^2$ represents isoxazyl or pyridyl wherein each of said ring systems may optionally be substituted with up to 3 $C_{1-6}$alkyl substituents;
(vi) $Het^4$ represents morpholinyl, pyrazolyl or imidazolyl;
(vii) $Het^5$ represents isoxazyl or pyridyl wherein each of said ring systems may optionally be substituted with up to 3 $C_{1-6}$alkyl substituents;
(viii) Ar represents phenyl optionally substituted with halo, $C_{1-6}$alkyl, $C_{1-6}$alkyl-O— or polyhalo$C_{1-6}$alkyl;
(ix) $Ar^1$ represents phenyl optionally substituted with one or where possible two, three or more halo substituents;
(x) $Ar^4$ represents phenyl;
(xi) $R^u$ and $R^v$ each independently represent hydrogen, $C_{1-6}$alkyl, phenyl or pyridyl wherein said phenyl or pyridyl or optionally substituted with one or where possible two, three or more substituents selected from halo or $C_{1-6}$alkyloxy-;
(xii) $R^x$ and $R^y$ each independently represent hydrogen, $C_{1-6}$alkyl-O—$C_{1-6}$alkyl, $C_{1-6}$alkyl, or $R^x$ and $R^y$ taken together with the N atom to which are attached form pyrrolidinyl An even further interesting embodiment of the present invention concerns those compounds of formula (I) wherein one or more of the following restrictions apply:
(i) Z is hydrogen, halo, $C_{1-6}$alkyl-O—C—(=O)—, HO—$C_{1-6}$alkyl-, cyano-$C_{1-6}$alkyl-, pyridylaminocarbonyl-, aminocarbonyl-$C_{1-6}$alkyl-, $Het^4$-$C_{1-6}$alkyl-, $C_{1-6}$alkyl-C(=O)—NH—$C_{1-6}$alkyl-; in particular embodiment Z represents hydrogen, $CH_3$—C(=O)—NH—$CH_2$—, ethoxycarbonyl, aminocarbonylmethyl-, pyridylaminocarbonyl-, morpholinomethyl-, hydroxymethyl, cyanomethyl, bromo, chloro or fluoro; in a more particular embodiment Z is halo, $C_{1-6}$alkyl-O—C—(=O)—, HO—$C_{1-6}$alkyl-, cyano-$C_{1-6}$alkyl-, aminocarbonyl-$C_{1-6}$alkyl-, $Het^4$-$C_{1-6}$alkyl-, $C_{1-6}$alkyl-C(=O)—NH—$C_{1-6}$alkyl-; in an even more particular embodiment Z represents $CH_3$—C(=O)—NH—$CH_2$—, ethoxycarbonyl, pyridylaminocarbonyl-, aminocarbonylmethyl-, morpholinomethyl-, hydroxymethyl, cyanomethyl, chloro, bromo or fluoro; in an even further embodiment Z represents hydrogen, halo, $C_{1-6}$alkyl-O—C—(=O)—, HO—$C_{1-6}$alkyl-, cyano-$C_{1-6}$alkyl-, pyridylaminocarbonyl- or aminocarbonyl-$C_{1-6}$alkyl-; also of interest are those compounds of formula (I) wherein Z represents hydrogen, methyl, hydroxymethyl, ethoxycarbonyl, methoxycarbonyl or pyridylaminocarbonyl; more in particular those compounds of formula (I) wherein Z represents hydrogen;
(ii) Q is phenyl, 2,3-dihydro-benzofuranyl, pyridyl or benzofuranyl each of said rings optionally being substituted with up to three substituents each independently selected from halo; $C_{1-6}$alkyl-; $C_{1-6}$alkyl-O— or polyhalo $C_{1-6}$alkyl; in particular Q represents benzofuranyl, 2,3-dihydro-benzofuranyl or phenyl substituted with one or two substituents selected from halo, $C_{1-6}$alkyl-O— or polyhalo$C_{1-6}$alkyl; even more particular Q represents benzofuranyl, 2,3-dihydro-benzofuranyl, pyridyl or phenyl wherein said pyridyl or phenyl are optionally substituted with one or two substituents selected from methyl, trifluoromethyl, fluoro, chloro or methoxy; in an even further embodiment Q represents phenyl or pyridyl wherein said pyridyl or phenyl are optionally substituted with one or two substituents selected from methyl, trifluoromethyl, fluoro, chloro or methoxy; in another particular embodiment Q represents phenyl or pyridyl wherein said phenyl is optionally substituted with one or two substituents selected from methyl, trifluoromethyl, fluoro, chloro or methoxy;

(iii) L is phenyl, pyridyl, piperidinyl, 8-Azapyrimidazolyl, 1,4-benzodioxanyl or pyrimidazolyl each of said rings optionally being substituted with up to three substituents each independently being selected from halo; hydroxy or $C_{1-6}$alkyl; in particular L is pyridyl; pyridyl substituted with halo, hydroxy or $C_{1-6}$alkyl; phenyl; phenyl substituted with halo, hydroxy or $C_{1-6}$alkyl-O—, in particular chloro, methoxy or hydroxy substituents; piperidinyl substituted with phenylmethoxycarbonyl; 1,4-benzodioxanyl or L is pyrimidazolyl;

(iv) $Het^4$ represents pyrrolidinyl, piperidynyl, thiomorpholinyl or morpholinyl; in particular $Het^4$ represents pyrrolidinyl, piperidynyl, thiomorpholinyl or morpholinyl wherein said pyrrolidinyl, piperidynyl, thiomorpholinyl or morpholinyl are attached to the remainder of the molecule via the N-atom.

Another particular embodiment of the present invention concerns those compounds of formula (I') wherein one of the following restrictions apply:

n is 0, 1, 2, 3 or 4; in particular n is 0, 1 or 2;

m is 0, 1, 2, 3 or 4; in particular m is 0, 1, 2, or 3;

$R^1$ each independently represents halo; hydroxy; cyano; $C_{1-6}$alkyl; $C_{1-6}$alkyl-O—; $C_{1-6}$alkylthio; $C_{1-6}$alkyl-O—C(=O)— or polyhalo$C_{1-6}$alkyl; in particular $R^1$ represents halo, $C_{1-6}$alkyl or $C_{1-6}$alkyl-O—;

$R^2$ each independently represents halo; hydroxy; amino; cyano; mono- or di($C_{1-6}$alkyl)amino; $C_{1-6}$alkyl; HO—$C_{1-6}$alkyl-; amino-$C_{1-6}$alkyl-; HO—C(=O)—$C_{1-6}$alkyl-; polyhalo$C_{1-6}$alkyl; $C_{1-6}$alkyloxy; $C_{1-6}$alkylthio; $C_{1-6}$alkyl-O—C(=O)—; aminocarbonyl; or $C_{1-6}$alkyl-C(=O)—NH—; in particular $R^2$ represents halo; hydroxy; polyhalo$C_{1-6}$alkyl or $C_{1-6}$alkyloxy;

Z is $Het^1$; HO—$C_{1-4}$alkyl-; $C_{1-6}$alkyl-C(=O)—NH—$C_{1-4}$alkyl-; cyano-$C_{1-4}$alkyl-; $C_{1-6}$alkyl-O—C(=O)—; halo; $R^uR^vN$—C(=O)—; $C_{1-6}$alkyl-O—$C_{1-6}$alkyl-; formylamino-$C_{1-4}$alkyl-; $Het^4$-$C_{1-4}$alkyl-; $R^xR^yN$—C(=O)—$C_{1-4}$alkyl-; phenyl-; or Z represents $C_{1-6}$alkyloxy-C(=O)—$C_{2-4}$alkyl-, provided however that Z is other than ethoxycarbonyl; in particular Z is $Het^1$; HO—$C_{1-4}$alkyl-; $C_{1-6}$alkyl-C(=O)—NH—$C_{1-4}$alkyl-; cyano-$C_{1-4}$alkyl-; formylamino-$C_{1-4}$alkyl-; $Het^4$-$C_{1-4}$alkyl-; $R^xR^yN$—C(=O)—$C_{1-4}$alkyl-; phenyl-; or Z represents $C_{1-6}$alkyloxy-C(=O)—$C_{2-4}$alkyl-; in an even further embodiment Z represents HO—$C_{1-4}$alkyl-; halo; pyridylaminocarbonyl; $C_{1-6}$alkyl-O—$C_{1-6}$alkyl or Z represents $C_{1-6}$alkyloxy-C(=O)—$C_{2-4}$alkyl-;

$Het^1$ represents morpholinyl, imidazolyl or pyrazolyl;

$Het^4$ represents morpholinyl, imidazolyl or pyrazolyl; in particular $Het^4$ represents morpholinyl;

$Het^6$ represents pyridyl $R^x$ and $R^y$ each independently represent hydrogen, $C_{1-6}$alkyl or $R^x$ and $R^y$ taken together with the N atom to which they are attached form a 5 or 6 membered heterocycle selected from pyrrolidinyl, thiomorpholinyl, piperidinyl or morpholinyl; in particular $R^x$ and $R^y$ each independently represent hydrogen, $C_{1-6}$alkyl or $R^x$ and $R^y$ taken together with the N atom to which they are attached form pyrrolidinyl;

$R^u$ and $R^v$ each independently represent hydrogen, $C_{1-6}$alkyl, $Het^6$ or $R^x$ and $R^y$ taken together with the N atom to which they are attached form a 5 or 6 membered heterocycle selected from pyrrolidinyl, thiomorpholinyl, piperidinyl or morpholinyl.

Also an interesting embodiment of the present invention concerns those compounds of formula (I") wherein one or more of the following restrictions apply;

n is 0, 1, 2, 3 or 4; in particular N is 0 or 1;

m is 0, 1, 2, 3 or 4; in particular m is 0, 1, 2 or 3;

$R^1$ each independently represents halo; hydroxy; $C_{1-6}$alkyl; $C_{1-6}$alkyl-O—; $C_{1-6}$alkylthio; $C_{1-6}$alkyl-O—C(=O)— or polyhalo$C_{1-6}$alkyl; in particular $R^1$ represents halo; $C_{1-6}$alkyl; $C_{1-6}$alkyl-O— or polyhalo$C_{1-6}$alkyl;

$R^2$ each independently represents halo; hydroxy; amino; cyano; mono- or di($C_{1-6}$alkyl)amino; $C_{1-6}$alkyl; HO—$C_{1-6}$alkyl-; amino-$C_{1-6}$alkyl-; carboxyl-$C_{1-6}$alkyl-; polyhalo$C_{1-6}$alkyl; $C_{1-6}$alkyl-O—; $C_{1-6}$alkylthio; $C_{1-6}$alkyl-O—C(=O)—; aminocarbonyl; or $C_{1-6}$alkyl-C(=O)—NH—; in particular $R^2$ represents halo; amino, $C_{1-6}$alkyl-O— or $C_{1-6}$alkyl;

Z is halo; $C_{1-6}$alkyl; halo$C_{1-6}$alkyl; $C_{1-6}$alkyl-O—$C_{1-6}$alkyl; $Het^1$; HO—$C_{1-4}$alkyl-; $C_{1-6}$alkyl-C(=O)—NH—$C_{1-4}$alkyl-; cyano-$C_{1-4}$alkyl-; $C_{1-6}$alkyloxy-C(=O)—NH—$C_{1-6}$alkyl; $C_{1-6}$alkyl-S(=O)$_2$—NH—$C_{1-6}$alkyl; formylamino-$C_{1-4}$alkyl-; mono- or di($C_{1-6}$alkyl)amino-$C_{1-6}$alkyl-; $Het^4$-$C_{1-4}$alkyl-; $R^xR^yN$—C(=O)—$C_{1-4}$alkyl-; phenyl-; $Het^5$-C(=O)—NH—$C_{1-6}$alkyl; $Ar^5$—C(=O)—NH—$C_{1-6}$alkyl or $C_{1-6}$alkyloxy-C(=O)—$C_{2-4}$alkyl-; in particular Z is $Het^1$; HO—$C_{1-4}$alkyl-; $C_{1-6}$alkyl-C(=O)—NH—$C_{1-4}$alkyl-; cyano-$C_{1-4}$alkyl-; formylamino-$C_{1-4}$alkyl-; $Het^4$-$C_{1-4}$alkyl-; $R^xR^yN$—C(=O)—$C_{1-4}$alkyl-; phenyl-; or Z represents $C_{1-6}$alkyloxy-C(=O)—$C_{2-4}$alkyl-; in a further embodiment Z represents halo, $C_{1-6}$alkyl; halo$C_{1-6}$alkyl; $C_{1-6}$alkyl-O—$C_{1-6}$alkyl; HO—$C_{1-4}$alkyl-; $C_{1-6}$alkyl-C(=O)—NH—$C_{1-4}$alkyl-; cyano-$C_{1-4}$alkyl-; $C_{1-6}$alkyloxy-C(=O)—NH—$C_{1-6}$alkyl; $C_{1-6}$alkyl-S(=O)$_2$—NH—$C_{1-6}$alkyl; mono- or di($C_{1-6}$alkyl)amino-$C_{1-6}$alkyl-; $Het^4$-$C_{1-4}$alkyl-; $R^xR^yN$—C(=O)—$C_{1-4}$alkyl-; $Het^5$-C(=O)—NH—$C_{1-6}$alkyl or $Ar^5$—C(=O)—NH—$C_{1-6}$alkyl;

$Het^1$ represents morpholinyl, imidazolyl, pyrrolidinyl or pyrazolyl; in particular $Het^1$ represents morpholinyl, imidazolyl or pyrazolyl;

$Het^4$ represents morpholinyl, imidazolyl, pyrrolidinyl or pyrazolyl; in particular $Het^4$ represents morpholinyl, imidazolyl or pyrazolyl; in particular $Het^4$ represents morpholinyl or pyrrolidinyl;

$Het^5$ represents isoxazolyl or pyridyl wherein each of said ring systems may optionally be substituted with up to three $C_{1-6}$alkyl substituents;

$Ar^5$ represents phenyl optionally substituted with hydroxy, halo or polyhalo$C_{1-6}$alkyl; in particular $Ar^5$ represents phenyl;

$R^x$ and $R^y$ each independently represent hydrogen, $C_{1-6}$alkyl, $C_{1-6}$alkyl-O—$C_{1-6}$alkyl or $R^x$ and $R^y$ taken together with the N atom to which they are attached form a 5 or 6 membered heterocycle selected from pyrrolidinyl, thiomorpholinyl, piperidinyl or morpholinyl; in particular $R^x$ and $R^y$ each independently represent hydrogen, $C_{1-6}$alkyl or $R^x$ and $R^y$ taken together with the N atom to which they are attached form a 5 or 6 membered heterocycle selected from pyrrolidinyl, thiomorpholinyl, piperidinyl or morpholinyl;

provided that Z is other than hydroxyl-$C_{1-2}$alkyl, halo, methyl, ethoxycarbonyl-, methoxycarbonyl-, dimethylaminomethyl-, dimethylaminoethyl-, ethylaminomethyl- or morpholinyl-$C_{1-2}$alkyl; when in the compound of formula (I″) the pyridyl ring is attached at positions 3 or 4 to the thiazole ring.

Another interesting embodiment of the present invention concerns those compounds of formula (I), (I′), (I″) or (I‴) wherein Z is bromo, hydroxymethyl, methyl-C(=O)—NH-methyl-, morpholino-methyl-, cyanomethyl-, aminocarbonyl-methyl-, methylaminocarbonyl-methyl-, dimethylaminocarbonyl-methyl-, benzyl, imidazolyl, pyrazolyl or pyrrolidinyl-carbonyl-methyl-.

In a further embodiment the present invention provides the compounds of formula (I′) wherein one or more of the following restrictions apply;
- (i) m is 1, 2 or 3
- (ii) n is 0, 1, 2 or 3; in particular n is 0 or 2
- (iii) Z is hydrogen, halo, $C_{1-6}$alkyl-O—C(=O)—, $R^uR^vN$—C(=O)—, HO—$C_{1-6}$alkyl-, cyano-$C_{1-6}$alkyl-, $R^xR^yN$—C(=O)—$C_{1-6}$alkyl-, $Het^4$-$C_{1-6}$alkyl-, $C_{1-6}$alkyl-C(=O)—NH—$C_{1-6}$alkyl-, $Het^5$-C(=O)—NH—$C_{1-6}$alkyl; in particular Z is bromo, fluoro, hydroxymethyl, methyl-C(=O)—NH-methyl, morpholino-methyl-, cyanomethyl-, ethoxycarbonyl-, aminocarbonyl-methyl-, methylaminocarbonyl-methyl-, dimethylaminocarbonyl-methyl-, methylaminocarbonyl-, benzyl, imidazolyl, pyrazolyl or pyrrolidinyl-carbonyl-methyl-; more in particular Z is bromo, hydroxymethyl, methyl-C(=O)—NH-methyl, morpholino-methyl-, cyanomethyl-, aminocarbonyl-methyl-, methylaminocarbonyl-methyl-, dimethylaminocarbonyl-methyl-, benzyl, imidazolyl, pyrazolyl or pyrrolidinyl-carbonyl-methyl-;
- (iv) $R^1$ each independently represents halo, $C_{1-6}$alkyl, $C_{1-6}$alkyl-O— or polyhalo$C_{1-6}$alkyl; in particular $R^1$ each independently represents fluoro, chloro, methyl, methoxy or trifluoromethyl;
- (v) $R^2$ each independently represents halo, $C_{1-6}$alkyl, $C_{1-6}$alkyl-O— or polyhalo$C_{1-6}$alkyl; in particular $R^2$ each independently represents fluoro, chloro, methyl, methoxy or trifluoromethyl; even more particular $R^2$ each independently represents fluoro, chloro, or methoxy.
- (vi) $Het^4$ represents morpholinyl
- (vii) $Het^5$ represents pyridyl or isoxazolyl wherein said isoxazolyl is optionally substituted with $C_{1-6}$alkyl; in particular $Het^5$ represents pyridyl or isoxazolyl wherein said isoxazolyl is substituted with $C_{1-6}$alkyl, in particular methyl
- (viii) $R^u$ and $R^v$ each independently represents hydrogen or $C_{1-6}$alkyl
- (ix) $R^x$ and $R^y$ each independently represent hydrogen, $C_{1-6}$alkyl or $C_{1-6}$alkyl-O—$C_{1-6}$alkyl.

In a further embodiment the present invention provides the compounds of formula (I′) wherein one or more of the following restrictions apply;
- (i) m is 1, 2 or 3
- (ii) n is 0 or 1
- (iii) Z is hydrogen, halo, $C_{1-6}$alkyl-O—C(=O)—, $R^uR^vN$—C(=O)—, HO—$C_{1-6}$alkyl-, cyano-$C_{1-6}$alkyl-, $R^xR^yN$—C(=O)—$C_{1-6}$alkyl-, $Het^4$-$C_{1-6}$alkyl-, $C_{1-6}$alkyl-C(=O)—NH—$C_{1-6}$alkyl-, $Het^5$-C(=O)—NH—$C_{1-6}$alkyl; in particular Z is bromo, fluoro, hydroxymethyl, methyl-C(=O)—NH-methyl-, pyridyl-C(=O)—NH-methyl-, morpholino-methyl-, cyanomethyl-, aminocarbonyl-methyl-, methoxyethyl-, aminocarbonyl-methyl-, isopropyl-aminocarbonyl-methyl-, methylaminocarbonyl-methyl-, dimethylaminocarbonyl-methyl-, benzyl, imidazolyl, pyrazolyl or pyrrolidinyl-carbonyl-methyl-; more in particular Z is bromo, hydroxymethyl, methyl-C(=O)—NH-methyl-, morpholino-methyl-, cyanomethyl-, aminocarbonyl-methyl-, pyrrolidinyl-carbonyl-methyl-methylaminocarbonyl-methyl-, dimethylaminocarbonyl-methyl-, benzyl, imidazolyl, pyrazolyl or isoxazolyl-C(=O)—NH-methyl-wherein said isoxazolyl is substituted with methyl;
- (iv) $R^1$ each independently represents halo, $C_{1-6}$alkyl, $C_{1-6}$alkyl-O— or polyhalo$C_{1-6}$alkyl; in particular $R^1$ each independently represents fluoro, chloro, methyl, methoxy or trifluoromethyl;
- (v) $R^2$ each independently represents halo or $C_{1-6}$alkyl; in particular $R^2$ each independently represents fluoro, chloro or methyl; even more particular $R^2$ each independently represents chloro, or methyl;
- (x) $Het^4$ represents morpholinyl
- (xi) $Het^5$ represents pyridyl or isoxazolyl wherein said isoxazolyl is optionally substituted with $C_{1-6}$alkyl; in particular $Het^5$ represents pyridyl or isoxazolyl wherein said isoxazolyl is substituted with $C_{1-6}$alkyl, in particular methyl
- (xii) $R^u$ and $R^v$ each independently represents hydrogen or $C_{1-6}$alkyl
- (xiii) $R^x$ and $R^y$ each independently represent hydrogen, $C_{1-6}$alkyl or $C_{1-6}$alkyl-O—$C_{1-6}$alkyl.

In a further embodiment the present invention provides the compounds of formula (I) wherein one or more of the following restrictions apply;
- (i) Z is hydrogen, halo, $C_{1-6}$alkyl-O—C(=O)—, $R^uR^vN$—C(=O)—, HO—$C_{1-6}$alkyl-, cyano-$C_{1-6}$alkyl-, $R^xR^yN$—C(=O)—$C_{1-6}$alkyl-, $Het^4$-$C_{1-6}$alkyl-, $C_{1-6}$alkyl-C(=O)—NH—$C_{1-6}$alkyl-, $Het^5$-C(=O)—NH—$C_{1-6}$alkyl;
- (ii) Q is phenyl or 2,3-dihydro-benzofuranyl, each of said rings optionally being substituted with up to three substituents selected from halo, $C_{1-6}$alkyl-O— or polyhalo$C_{1-6}$alkyl;
- (iii) L is phenyl, pyridyl, pyrimidazolyl or 1,4-benzodioxanyl, each of said rings optionally being substituted with up to three substituents selected from halo, hydroxy or $C_{1-6}$alkyl;
- (iv) $Het^4$ represents morpholinyl
- (v) $Het^5$ represents pyridyl or isoxazolyl wherein said isoxazolyl is optionally substituted with $C_{1-6}$alkyl; in particular $Het^5$ represents pyridyl or isoxazolyl wherein said isoxazolyl is substituted with $C_{1-6}$alkyl, in particular methyl
- (vi) $R^u$ and $R^v$ each independently represents hydrogen or $C_{1-6}$alkyl
- (vii) $R^x$ and $R^y$ each independently represent hydrogen, $C_{1-6}$alkyl or $C_{1-6}$alkyl-O—$C_{1-6}$alkyl.

In a further interesting embodiment of the present invention the compounds are selected from;

N-[4-Pyridin-3-yl-2-(3-trifluoromethyl-phenylamino)-thiazol-5-ylmethyl]-acetamide
2-(2,4-Dichloro-phenylamino)-4-phenyl-thiazole-5-carboxylic acid ethyl ester
2-[4-Phenyl-2-(3-trifluoromethyl-phenylamino)-thiazol-5-yl]-acetamide
2-[4-(2,4-Dichloro-phenyl)-2-(3-trifluoromethyl-phenylamino)-thiazol-5-yl]-acetamide (4-Fluoro-3-trifluoromethyl-phenyl)-(5-morpholin-4-ylmethyl-4-pyridin-3-yl-thiazol-2-yl)-amine
[2-(4-Fluoro-3-trifluoromethyl-phenylamino)-4-pyridin-4-yl-thiazol-5-yl]-methanol
[4-(2,4-Dichloro-phenyl)-2-(3-trifluoromethyl-phenylamino)-thiazol-5-yl]-acetonitrile
[4-(2,4-Dichloro-phenyl)-2-(3-trifluoromethyl-phenylamino)-thiazol-5-yl]-methanol
4-[2-(2,5-Dichloro-phenylamino)-thiazol-4-yl]-benzene-1,2-diol
(2,3-Dihydro-benzofuran-5-yl)-(4-imidazo[1,2-a]pyridin-3-yl-thiazol-2-yl)-amine
(2,4-Dimethoxy-phenyl)-(4-imidazo[1,2-a]pyridin-3-yl-thiazol-2-yl)-amine
[2-(4-Fluoro-3-trifluoromethyl-phenylamino)-4-pyridin-3-yl-thiazol-5-yl]-methanol
(4-Imidazo[1,2-a]pyridin-3-yl-thiazol-2-yl)-(4-methoxy-phenyl)-amine
(5-Fluoro-4-pyridin-3-yl-thiazol-2-yl)-(3-trifluoromethyl-phenyl)-amine
[4-Phenyl-2-(3-trifluoromethyl-phenylamino)-thiazol-5-yl]-acetonitrile
[4-(6-Methyl-pyridin-3-yl)-thiazol-2-yl]-(3-trifluoromethyl-phenyl)-amine
N-[[4-(3-pyridinyl)-2-[[3-(trifluoromethyl)phenyl]amino]-5-thiazolyl]methyl]-4-pyridinecarboxamide
2-[(4-methoxyphenyl)amino]-4-(4-pyridinyl)-5-thiazolemethanol
2-[(2,5-dichlorophenyl)amino]-4-(4-pyridinyl)-5-thiazoleacetamide
5-methyl-N-[[4-(3-pyridinyl)-2-[[3-(trifluoromethyl)phenyl]amino]-5-thiazolyl]methyl]-3-isoxazolecarboxamide
4-(2,3-dihydro-1,4-benzodioxin-6-yl)-2-[(2,4-dimethoxyphenyl)amino]-5-thiazolemethanol
2-[(5-chloro-2,4-dimethoxyphenyl)amino]-4-(2,3-dihydro-1,4-benzodioxin-6-yl)-5-thiazolemethanol
2-[(5-chloro-2,4-dimethoxyphenyl)amino]-4-(2,3-dihydro-1,4-benzodioxin-6-yl)-5-thiazoleacetamide
2-[(5-chloro-2,4-dimethoxyphenyl)amino]-4-(3,4-difluorophenyl)-N-methyl-5-thiazolecarboxamide
2-[(5-chloro-2,4-dimethoxyphenyl)amino]-4-(2,3-dihydro-1,4-benzodioxin-6-yl)-N-methyl-5-thiazoleacetamide
2-[(2,5-dichlorophenyl)amino]-N-(2-methoxyethyl)-4-(4-pyridinyl)-5-thiazoleacetamide
2-[(2,5-dichlorophenyl)amino]-N-(1-methylethyl)-4-(4-pyridinyl)-5-thiazoleacetamide or a N-oxide, a pharmaceutically acceptable addition salt, a quaternary amine and a stereochemically isomeric form thereof.

The compounds of this invention can be prepared by any of several standard synthetic processes commonly used by those skilled in the art of organic chemistry and described for instance in the following references; "Heterocyclic Compounds"—Vol. 24 (part 4) p 261-304 Fused pyrimidines, Wiley—Interscience; Chem. Pharm. Bull., Vol 41(2) 362-368 (1993); J. Chem. Soc., Perkin Trans. 1, 2001, 130-137. In particular the synthesis of compounds of formula (I) wherein Z is halo, substituted $C_{1-6}$alkyl, $C_{1-6}$alkyloxycarbonyl or $C_{1-6}$alkylcarbonyl, or wherein Z is $C_{1-6}$alkyl or cyano, is described in WO 03/015773.

Compounds of formula (I) wherein Z is hydrogen and $Ar^i$ represents an aromatic residue, including an optionally substituted phenyl or an optionally substituted pyridyl, hereinafter referred to as the compounds of formula (I-a), are generally prepared by heating an excess of a compound of formula (II) with a substituted thiourea of formula (III) in a protic solvent such as ethanol or a higher alkanol or a aprotic solvent such as DMF. Excess compound of formula (II) is scavenged by a nucleophile that is immobilized on a solid support such as polystyrene. A suitable nucleophile comprises a reactive amine such as TRIS. Optionally, the acid that is generated during the reaction can be quenched with an immobilized inorganic base, such as bicarbonate on polystyrene. The quenching step can be carried out in the same solvent as the thiazole ring formation and can be performed at room temperature or at elevated temperature (50° C.) for several hours, in particular 15 hours. The purification typically involves removing the polymer supported reagents and products by filtration, washing with a suitable solvent such as DMF or an alcohol and concentrating the filtrates by applying vacuum. In some cases further purification using chromatographic techniques might be appropriate, in particular reversed phase HPLC and further work-up known by people skilled in the art.

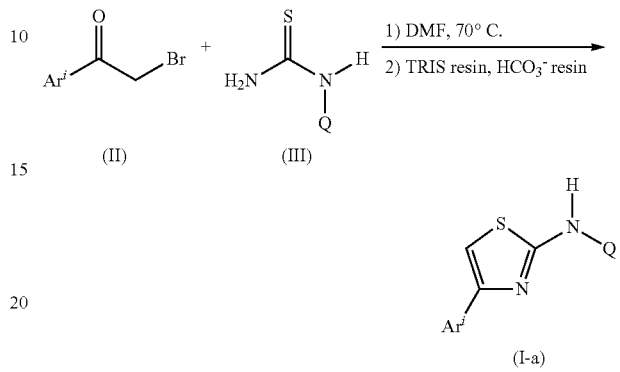

wherein Q is defined as for the compounds of formula (I) hereinbefore.

In addition to the compounds of formula (I) wherein Z represents substituted $C_{1-6}$alkyl as described in WO 03/015773, those compounds of formula (I) wherein Z represents $C_{1-6}$alkyl substituted with hydroxy, cyano or aminocarbonyl, hereinafter referred to as the compounds of formula (I-$b_{1-3}$), are generally prepared by heating the compounds of formula (I-a) as the free base or a salt such as the hydrochloride or hydrobromide with formaldehyde (IV) in a water miscible organic co-solvent such as THF, in the presence of a base, such as for example triethylamine

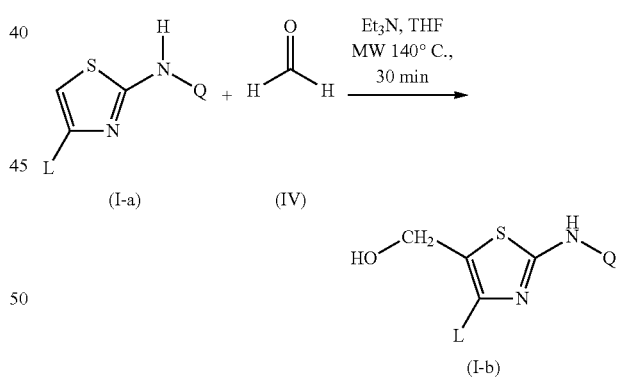

The subsequent transformation of the primary alcohol (I-$b_1$) into the cyanomethyl (I-$b_2$) consists of a two step reaction with in the first step a conversion of the alcohol into a suitable leaving group, in particular a halide (X in scheme hereinafter) using art known reaction conditions, i.e. using strongly acidic conditions, such as for example 30% HBr in acetic acid or HCl in 1,4-dioxane, followed by the nucleophilic displacement of the halide with an inorganic cyanide, such as for example sodium cyanide, in an aprotic solvent such as DMF. The reaction is most preferably carried out by suspending the cyanide in DMF, to which the halide is added in the solid state.

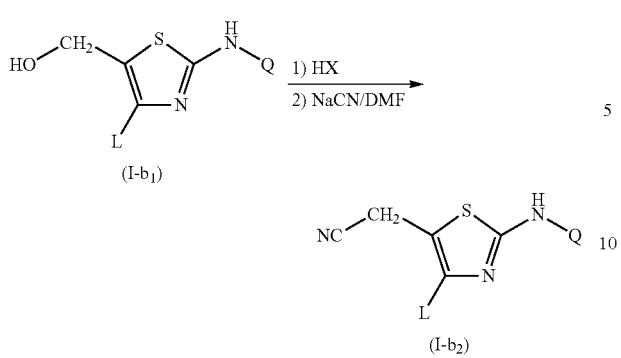

Hydrolysis of the cyano substituted $C_{1-6}$alkyl (I-b$_2$) yields the aminocarbonyl substituted compounds of formula (I-b$_3$). This reaction is typically performed by reaction in a mixture of $H_2SO_4/H_2O$. Alternatively this reaction is performed using urea-hydroperoxide in a two solvent system consisting of water and a water miscible organic co-solvent such as acetone in the presence of an inorganic base, such as for example $K_2CO_3$.

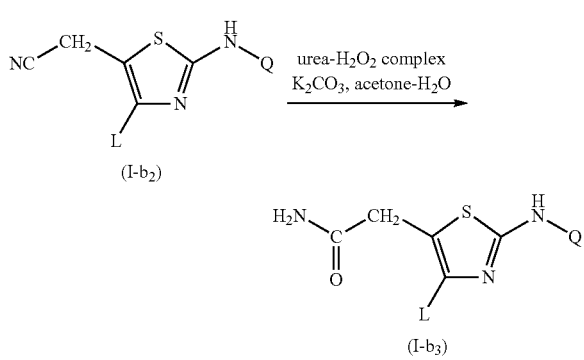

Alternatively, those compounds of formula (I-b$_1$) can be prepared by reduction of the appropriate ethylester (V) with a hydride reductant, in particular using lithium borohydride in an aprotic solvent such as THF at an elevated temperature, such as 60° C.

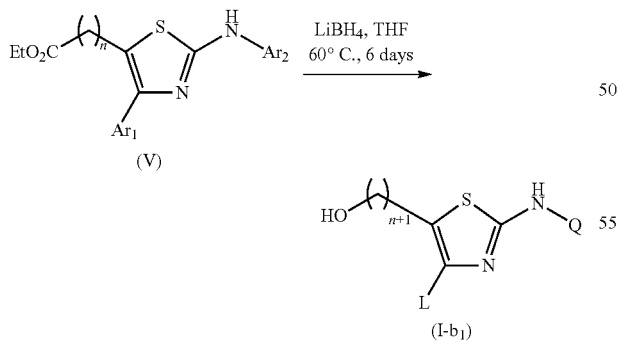

Conversion into the cyano-alkyl and reduction into the aminocarbonyl as described for the cyanomethyl hereinbefore, provides those compounds of formula (I) wherein Z represents $C_{1-6}$alkyl substituted with cyano or aminocarbonyl.

Compounds of formula (I) wherein Z is $C_{1-6}$alkyl substituted with amino, mono- or di($C_{1-6}$alkyl)amino, piperidinyl, piperazinyl, morpholinyl, thiomorpholinyl, said Z being represented by $Z_c$—$C_{1-6}$alkyl, and said compounds being represented by formula (I-c), can be prepared by reacting an intermediate of formula (VI) wherein $W_3$ represents a suitable leaving group, such as for example halo, e.g. chloro, with an intermediate of formula (VII) in the presence of a suitable base, such as for example $NaHCO_3$, and a suitable solvent, such as for example acetonitrile.

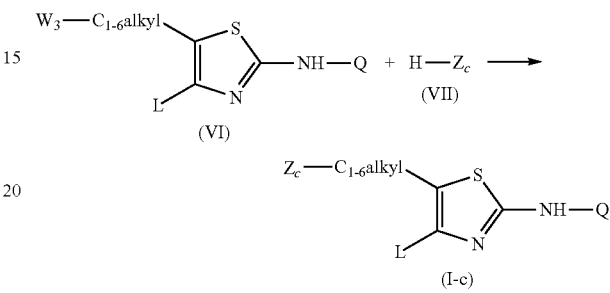

Further $C_{1-6}$alkyl-carbonyl substituted aminoalkyl derivatives are prepared departing from the known cyanide (I-d). Reduction of said cyanide using art known conditions, such as for example using hydrogen in the presence of a suitable catalyst such as Raney nickel in a solvent system like methanol-ammonia and THF, provides the amine of formula (I-c$_1$).

Acylation of the amine of formula (I-c$_1$) with an acylating agent, such as for example an acylhalide including acetylchloride, arylcarbonylhalide or heteroarylcarbonylhalide; in the presence of an amine base, such as triethyl amine in a suitable solvent, such as for instance THF, provides the acylamines of formula (I-e)

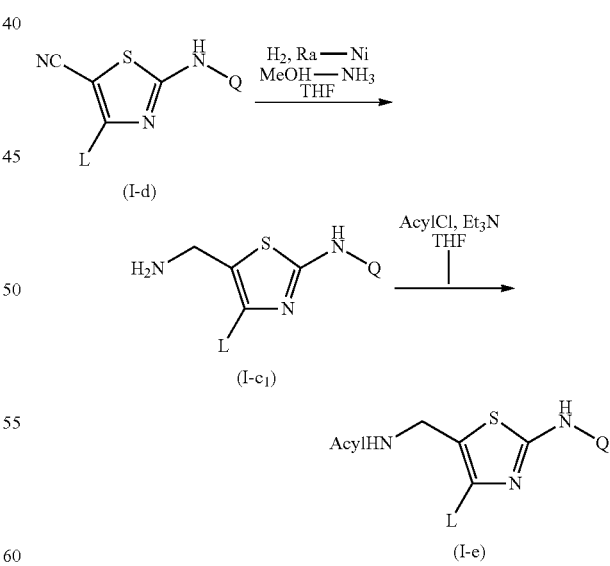

Sulfonylation of the amine of formula (I-c$_1$) with an sulfonylating agent, such as for example methanesulfonyl chloride when R represents methyl; in the presence of an amine base, such as triethyl amine in a suitable solvent, such as for instance THF, provides the sulfonamides of formula (I-e$_1$)

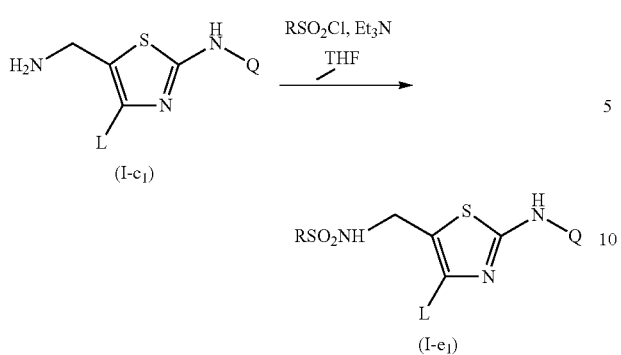

For those compounds of formula (I) wherein Z represents Het³ are generally prepared using art known metal-catalyzed coupling reactions such as Buchwald/Hartwig, Suzuki, and Stille coupling reactions. Briefly, for those compounds of formula (I) wherein the Het³ is linked through a carbon atom with the thiazole ring, hereinafter referred to as the compounds of formula (I-f₁), said compounds can be obtained by reacting a 5-halo aminothiazole of formula (XI), such as for example a 5-bromo aminothiazole, with a metallated heterocycle Het³. M as used herein, can be a boronic acid (M=BOH₂) or the corresponding ester, such as a pinacolo borane. Alternatively, M can be an organostannane, such as Sn(n-Bu)₃. The reaction is best performed in an aprotic organic solvent such as toluene, 1,4-dioxane, DMF and the like, at an elevated temperature, typically in the range of 80 to 150° C. The reaction is advantageously carried out in the presence of a metal catalyst, such as palladium, and a ligand, such as triphenyl phosphine and also typically requires a base such as potassium phosphate, cesium carbonate and the like, or an amine base, such as triethyl amine

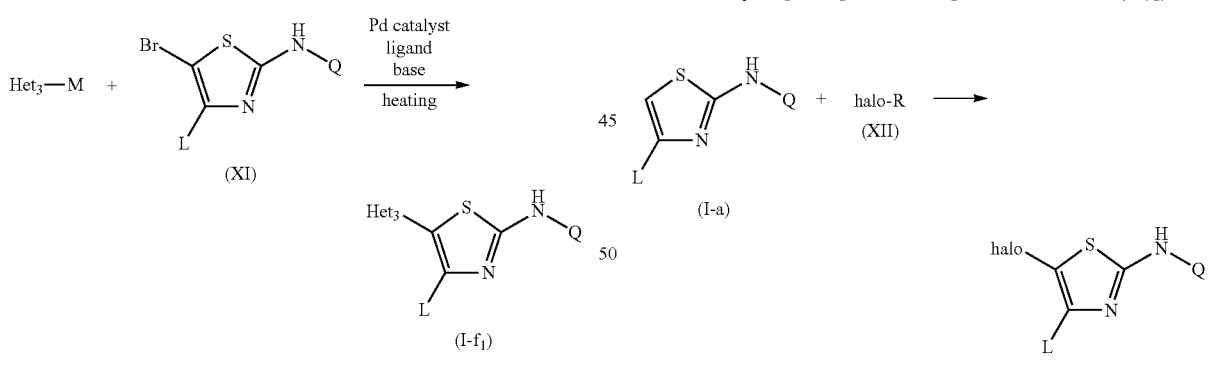

For those compounds of formula (I) wherein the Het³ is linked through a nitrogen atom with the thiazole ring, hereinafter referred to as the compounds of formula (I-f₂), said compounds can be obtained by reacting a 5-halo aminothiazole, such as for example a 5-bromo aminothiazole, with an aromatic or saturated Het³ having a free NH. The reaction can be performed in the presence of a copper catalyst, such as Cu(I) iodide in the presence of a ligand such as ethylene diamine and the like and may require an inorganic base such as cesium carbonate and the like. This transformation typically requires a high-boiling aprotic solvent such as dimethyl acetamide or N-methyl pyrrolidinone and the like and can best be performed at elevated temperatures, typically between 80 to 150° C. Alternatively, the copper catalyst can be replaced by a palladium catalyst. In this case the reaction requires a ligand such as BINAP, and a strong inorganic base, such as sodium tert-butoxide and the like. A suitable solvent is an aprotic solvent such as toluene, 1,4-dioxane, DMF and the like and the reaction is performed at an elevated temperature in the range of 80 to 150° C.

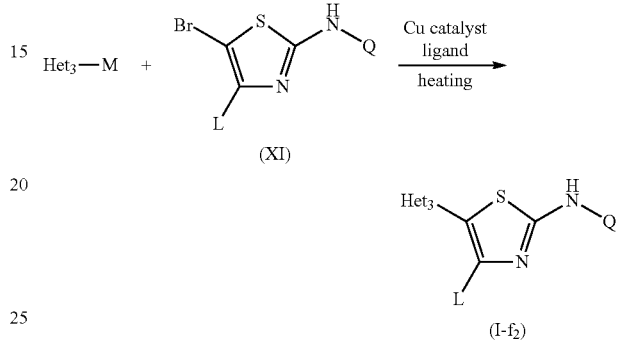

As already mentioned hereinbefore, the synthesis of the 5-halo aminothiazole (XI) has been described in PCT publication WO 03/015773. Briefly, said compounds can be prepared by reacting a compound of formula (I-a) with an halo-introducing agent of formula (XII) wherein R represents the remainder of the halo-introducing agent, in the presence of a suitable solvent, such as for example N,N-dimethylformamide, optionally in the presence of a suitable base, such as for example 2,6-lutidine. Suitable halo-introducing agents are for example 1-chloro-pyrrolidinedione, 1-bromo-pyrrolidinedione or Selectfluor® (1-(chloromethyl)-4-fluoro-1,4-diazoniabicyclo[2.2.2]octane, bis[tetrafluoroborate(1-)]).

The thioureas of formula (III') as used hereinbefore, and in particular the thioureas wherein Q represents an optionally substituted phenyl group, are generally prepared by reaction in a first step an appropriate aniline derivative of formula (VIII) with benzoyl isothiocyanate in the presence of an amine base, such as for example triethyl amine in a suitable solvent such as THF; followed by a base catalysed hydrolysis with a suitable base, such as for instance sodium hydroxide, in the presence of a suitable solvent, such as for example an alcohol, e.g. ethanol at reflux temperature.

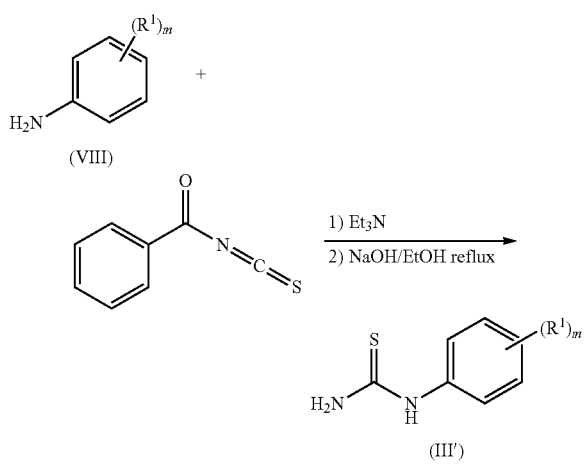

wherein $R^1$ and m are defined as for the compounds of formula (I') hereinbefore.

Synthesis of the arylcarbonyl derivatives of formula (II) is described in WO 03/015773, briefly, an intermediate of formula (IX) is halogenated with a bromine transferring agent under art known conditions, for example with N,N,N-trimethylbenzenaminium tribromide in the presence of a suitable solvent, such as for example tetrahydrofuran and an alcohol, e.g. methanol.

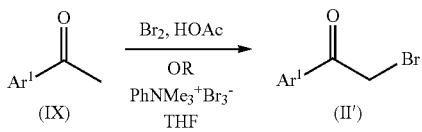

For those compounds of formula (I) wherein L represents an amino substituted pyridyl, the intermediates of formula (IX) are prepared departing from the appropriate acetyl-nicotinic acid by a Curtius rearrangement involving the heating of said carboxylic acid in an alcohol, e.g. tert-butyl alcohol in the presence of DPPA and an amine base, such as triethyl amine, yielding the Boc-protected amine derivative of formula (X). Deprotection under acidic conditions, such as heating said intermediate of formula (X) in aqueous hydrochloric acid and a suitable solvent such as ethanol, yields the amino substituted intermediate of formula (IX-a).

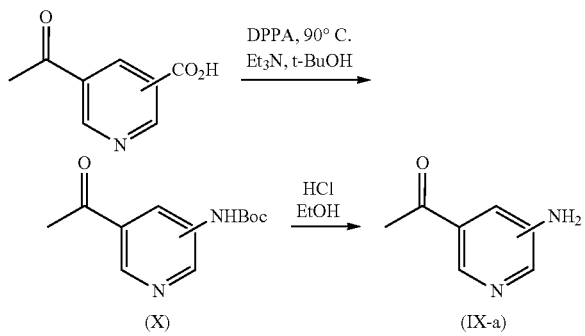

For those compounds of formula (I) wherein L represents a fluoro substituted pyridyl, the intermediates of formula (IX) are prepared departing from the appropriate fluoro-nicotinoyl chloride by methylation using a methyl anion equivalent, in particular dimethyl malonate and subsequent decarboxylation. The addition of dimethyl malonate can be performed in the presence of a Lewis acid, such as magnesium chloride and an amine base such as triethyl amine in a suitable solvent, e.g. toluene. The decarboxylation leading to the intermediate of formula (IX-b) can be carried out under aqueous conditions in the presence of a high boiling organic co-solvent, such as DMSO, at an elevated temperature, such as 160° C.

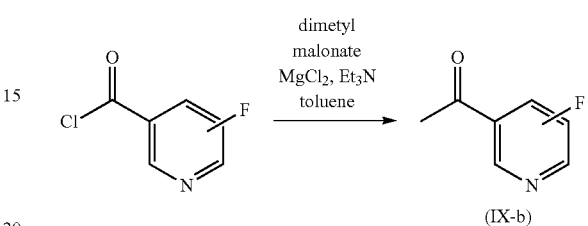

As shown hereinbefore, the 4-substituted 2-amino-thiazoles are generally prepared by heating an excess of an appropriate ketone (II) with a substituted thiourea (III) in a protic solvent such as ethanol or a higher alcohol or a protic solvent such as DMF. The 5-substituents of the thiazoles of the present invention subsequently being introduced. In an alternative method, the 5-substituted 4-aryl substituted 2-amino-thiazoles are obtained through a similar reaction from the alternative ketones of general formula (XIII).

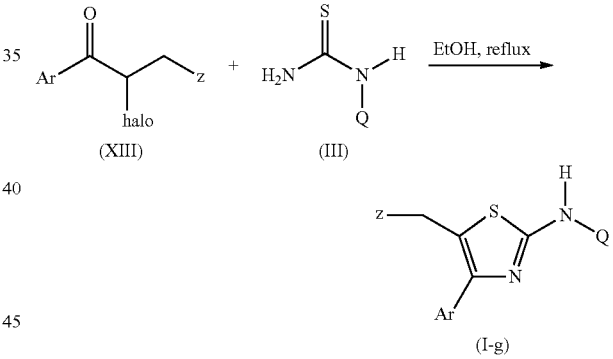

wherein z represents a cyano, cyano-$C_{1-4}$alkyl; the different amides as defined for the compounds of formula (I) hereinbefore; $C_{1-6}$alkyl-O—C(=O)— or $C_{1-6}$alkyl-S(=O)$_2$—.

Those compounds of formula (I-g) wherein z represents cyano or cyano-$C_{1-4}$alkyl can be converted in compounds of formula (I-g) wherein z represents amino-$C_{2-5}$alkyl by reaction with a suitable reducing agent, such as for example $H_2$, in the presence of a suitable catalyst, such as for example Raney Nickel, and as suitable solvent, such as for example tetrahydrofuran, or an alcohol, e.g. EtOH, preferentially in the presence of $NH_3$.

Those compounds of formula (I-g) wherein z represents cyano-$C_{1-4}$alkyl can also be converted in;
  those compounds of formula (I-g) wherein z represents aminocarbonyl-$C_{1-4}$alkyl by reaction in a mixture of $H_2SO_4/H_2O$.
  those compounds of formula (I-g) wherein z represents carboxyl-$C_{1-4}$alkyl by reaction with a suitable acid, such as concentrated hydrochloric acid, in the presence of a suitable solvent, e.g. water, optionally in the presence of a water miscible co-solvent such as for example 1,4-dioxane, THF or the like.

In the presence of a suitable reducing agent, such as for example LiBH$_4$ or LiAlH$_4$, and a suitable solvent, such as for example tetrahydrofuran or diethyl ether, those compounds of formula (I-g) wherein z represents C$_{1-6}$alkyl-O—C(=O)—C$_{1-4}$alkyl can be converted in those compounds of formula (I-g) wherein z represents HO—C$_{2-5}$alkyl. The ester function can also be converted in either the free carboxylic acid through hydrolysis of the ester, i.e. at an elevated temperature (40-100° C.) under either aqueous acid or saponification reaction conditions, or into an amide under art known conditions, i.e. at room temperature or slightly above (30-60° C.) by the use of a coupling agent such as for example O-Benzotriazole-N,N,N',N'-tetramethyl-uronium-hexafluoro-phosphate; N,N'-carbonyldiimidazole; dicyclohexylcarbodiimide; POCl$_3$; TiCl$_4$; sulfuryl chloride fluoride or chlorosulfonyl isocyanate, in a solvent such as dichloromethane, DMF or the like.

Said alternative ketones are the result of a nucleophilic acylation reaction of activated double bounds followed by a subsequent halogenation reaction.

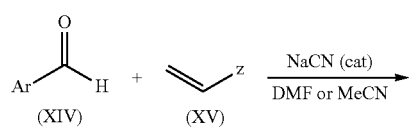

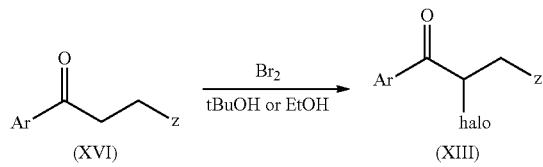

The nucleophilic acylation reaction of the α,β-unsaturated compound (XV), also known as the Stetter Reaction, is done under art known conditions, comprising the use of an umpoling reagent such as a cyanide ion or a heterazolium carbene, to change the normal carbonyl charge affinity (Stetter H. and Kuhlmann H. in *Organic Reactions*; Paquette L. A., Ed.; Wiley: New York, 1991; Vol 40, p. 407-496).

The subsequent halogenation reaction is done using standard conditions including, in the presence of a halogenating agent such as Br$_2$, SO$_2$Cl$_2$ or another halogenating reagent such as N-chlorosuccinimide (NCS).

As provided in more detail in the examples hereinafter, this alternative synthesis approach has been useful to;

directly introduce an ester or amide linked via an alkyl linker at C5 of the aminothiazoles of the present invention. Alternatively, this can be achieved using a keto-ester of general formula (XXIII) below.

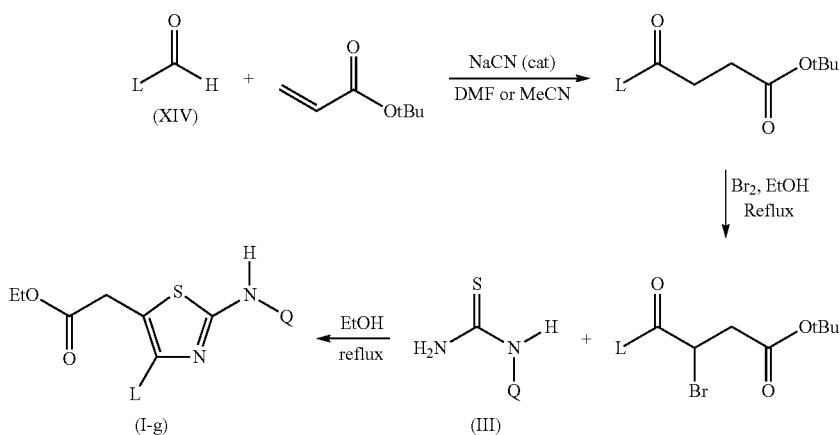

As already outlined hereinbefore, the ester can be converted in either the free carboxylic acid or into an amide under art known conditions.

directly introduce a nitrile via an alkyl linker at C5 of the aminothiazoles of the present invention.

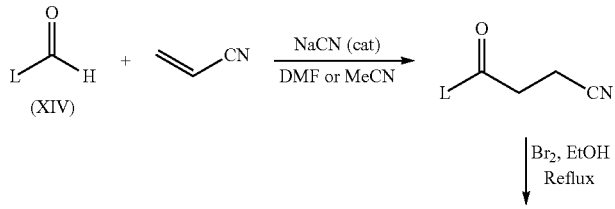

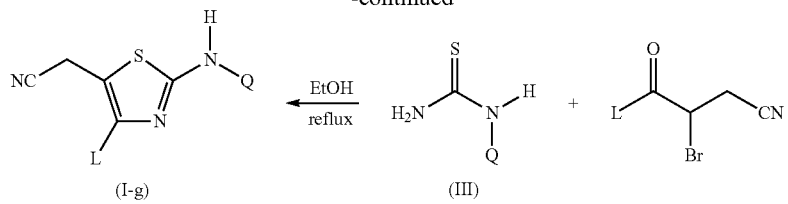

As already outlined hereinbefore, this nitrile can be converted into other functional groups, including free carboxylic acids, amines and amides following art-known procedures.

For a direct introduction of an ester or amide at C5 of the aminothiazoles of the present invention one would have to depart from a β-keto ester of the general formula (XX). The subsequent halogenation reaction, and thiazole formation is done using the general procedures described hereinbefore.

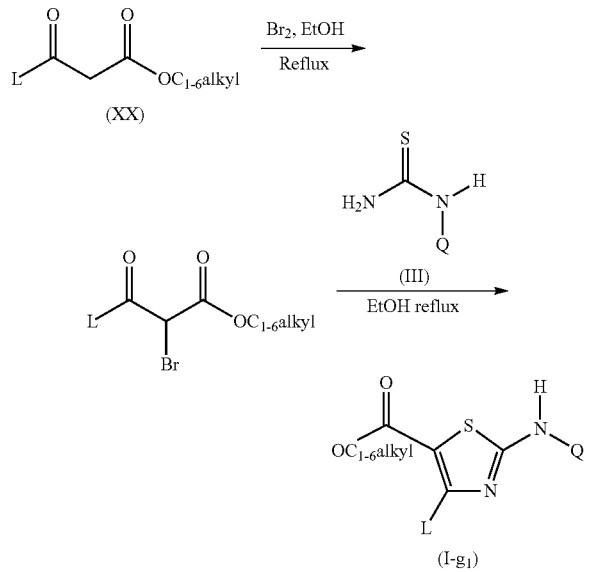

The preparation of the beta keto ester of the formula XX involves a 2 steps process. The carboxylic acid function in XVII is first converted into a suitable leaving group. When said leaving group is alkoxy, said transformation can be achieved by treating XVII with a protic acid, such as HCl, in an alcoholic solvent, such as ethanol and the like at a temperature range of 0° C.-80° C., typically at room temperature. When said leaving group is chloro, said transformation can be achieved by treating XVII with thionyl chloride as a solvent or oxalyl chloride in methylene chloride as the solvent or the like. A catalytic amount of dimethyl formamide accelarates said transformation significantly. A typical temperature range to effect said transformation is between 0° C.-50° C. When said leaving group is imidazole, said transformation can be achieved by treating XVII with carbonyl diimidazole in a polar aprotic solvent like acetonitrile or the like. Said transformation can be effected at a temperature range 0° C.-80° C., typically at room temperature. In a second step the carboxylic acid derivative XVIIa is treated with a malonic acid derivative, such as XVIII, in a polar aprotic solvent, such as acetonitrile or the like. Said transformation can be effected at a temperature range 0° C.-80° C., typically at room temperature.

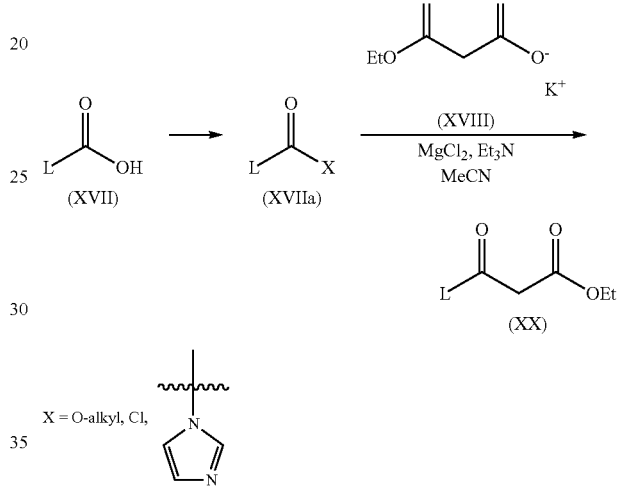

Alternatively to the above, an alkyl linked ester or amide can be introduced at C5 of the aminothiazoles of the present invention when departing from a keto ester of the general formula (XXIII). The subsequent halogenation reaction, and thiazole formation is done using the general procedures described hereinbefore.

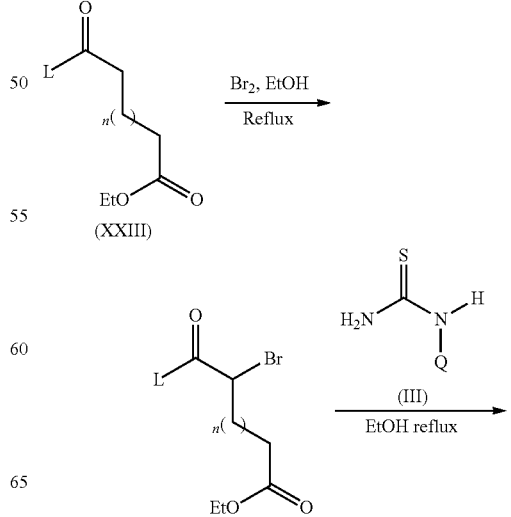

-continued

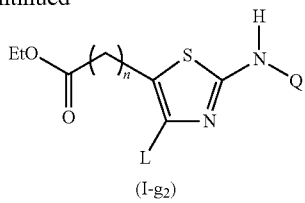

(I-g2)

n is 1 to 3

A keto ester of the general formula XXIII can be prepared in 3 steps starting from a beta keto ester of the general formula XX. The first step involves treating the keto ester with a halo carboxylic ester derivative XXI in an alcoholic solvent such as ethanol and the like, in the presence of the corresponding alcoholate base, such as NaOEt when the solvent is ethanol. Said transformation can be carried out at a temperature range of 20° C.-100° C., typically at 80° C. In the second step of this process, the di-ester XXII is treated with strong acid, such as concentrated hydrochloric acid at elevated temperature, typically at reflux temperature, resulting in hydrolysis of said diester and in situ decarboxylation. The intermediate mono carboxylic acid can optionally be converted into the corresponding carboxylic ester derivative of the general formula XXIII via an analogous process as described hereinbefore. It should be recognized by somebody skilled in the art, that other carboxylic acid derivatives, such as amides, can be prepared as well in an analogous fashion as described hereinbefore.

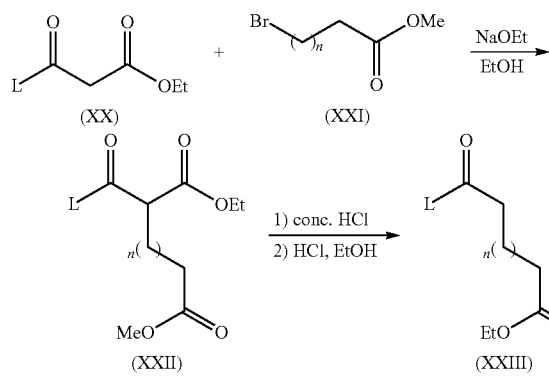

n = 1-3

More specific examples for the synthesis of compounds of formula (I) are provided in the examples hereinafter.

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer.

Compounds of formula (I), N-oxides, addition salts, quaternary amines and stereochemically isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which are desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$ alkyl or benzyl esters.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein L is substituted with amino may be converted into a compound of formula (I) wherein L is substituted with $C_{1-6}$alkylformylamino by reaction with a $C_{1-6}$alkylcarbonyl chloride in a suitable solvent, such as for example pyridine.

Compounds of formula (I) wherein Q is substituted with cyano may be converted into a compound of formula (I), wherein Q is substituted with carboxyl by reaction with a suitable acid, such as concentrated hydrochloric acid, in the presence of a suitable solvent, e.g. water.

Compounds of formula (I), wherein L is substituted with $C_{1-6}$alkyl-C(=O)—NH—, may be converted into a compound of formula (I), wherein L is substituted with amino, by reaction with a suitable acid, such as for example hydrobromic acid and the like, in the presence of a suitable solvent, such as water.

Compounds of formula (I) wherein Z is cyano may be converted into a compound of formula (I) wherein Z is aminocarbonyl by reaction in a mixture of $H_2SO_4/H_2O$.

Compounds of formula (I) wherein Z is cyano may also be converted into a compound of formula (I) wherein Z is —$CH_2$—$NH_2$ by reaction with a suitable reducing agent, such as for example $H_2$, in the presence of a suitable catalyst, such as for example Raney Nickel, and a suitable solvent, such as for example tetrahydrofuran, or an alcohol, e.g. $CH_3OH$, preferentially in the presence of $NH_3$ Compounds of formula (I) wherein Z is $C_{1-6}$alkyloxycarbonyl may be converted into a compound of formula (I)

wherein Z is —CH$_2$—OH in the presence of a suitable reducing agent, such as for example LiBH$_4$ or diisobutylalluminiumhydride (DIBAL), and a suitable solvent, such as for example tetrahydrofuran.

Compounds of formula (I) wherein Z is C$_{1-6}$alkylcarbonyl can be converted into a compound of formula (I) wherein Z is C$_{1-6}$alkyl-CHOH— in the presence of a suitable reducing agent, such as for example NaBH$_4$ or diisobutylalluminiumhydride (DIBAL), and a suitable solvent, such as for example tetrahydrofuran or diethyl ether.

Compounds of formula (I) wherein Z is C$_{1-6}$alkyl substituted with amino, can be converted into a compound of formula (I) wherein Z is C$_{1-6}$alkyl substituted with amino which is substituted with piperidinyl or C$_{1-4}$alkyl substituted piperidinyl, by reaction with piperidine or C$_{1-4}$alkyl substituted piperidine in the presence of H$_2$, a suitable catalyst, such as for example palladium on charcoal, a suitable catalyst poison, such as for example a thiophene solution, and a suitable solvent, such as for example an alcohol, e.g. methanol and the like.

Compounds of formula (I) wherein Z is C$_{1-6}$alkyl substituted with amino, can also be converted into a compound of formula (I) wherein Z is C$_{1-6}$alkyl substituted with dimethylamino, by reaction with paraform in the presence of H$_2$, a suitable catalyst, such as for example palladium on charcoal, a suitable catalyst poison, such as for example a thiophene solution, and a suitable solvent, such as for example an alcohol, e.g. methanol and the like.

The compounds of the present invention were found to be positive modulators of the α7 nicotinic receptor. The α7 nicotinic receptor (α7 nAChR) belongs to the superfamily of cys-loop, ionotropic ligand-gated ion channels which includes the 5-HT$_3$, GABA$_A$ and glycine receptor families. It is activated by acetylcholine and its breakdown product choline and a major feature of the α7 nAChR is its rapid desensitisation in the persistent presence of agonist. It is the second most abundant nicotinic receptor subtype in the brain and is an important regulator of release of many neurotransmitters. It has a discrete distribution in several brain structures with relevance to attentional and cognitive processes, such as the hippocampus and pre-frontal cortex and has been implicated in a variety of psychiatric and neurological disorders in humans.

Genetic evidence for its association with schizophrenia is seen in the form of strong linkage between a schizophrenia marker (sensory gating deficit) and the α7 locus on 15q13-14 (Freedman et al. 1997. PNAS 94, 587-592) and polymorphisms in core promoter region of the α7 gene (Leonard et al. 2002).

Pathological evidence points to a loss of α7 immunoreactivity and α-Btx-binding in the hippocampus, frontal and cingulate cortex of schizophrenic brains (Freedman et al. 1995; Guan et al. 1999; Marutle et al. 2001), in Parkinson's and Alzheimer's disease (Banerjee et al. 2000; Burghaus et al. 2000) and paraventricular nucleus and nucleus reuniens in autism (Ray et al. 2005).

Pharmacological evidence such as the marked smoking habits of schizophrenics compared to normals have been interpreted as an attempt by the patients to self-medicate to make up for a deficit in α7 nicotinergic transmission (Dalack et al. 1998). Transient normalization of defects in sensory gating (PPI) in both animal models and man upon nicotine administration (Adler et al. 1982; Bickford and Wear, 1995) and temporary restoration of normal sensory gating in schizophrenics when forebrain cholinergic activity low (e.g. stage 2 sleep) (Griffith et al. 1998) have both been interpreted to be the result of transient activation of the α7 nicotinic receptor followed by desensitisation.

Thus there is good reason to suppose that activating the α7 nAChR will have therapeutically beneficial effects for a number of CNS (psychiatric and neurological) disorders.

As already mentioned the α7 nAChR rapidly desensitises in the persistent presence of the natural transmitter acetylcholine as well as exogenous ligands such as nicotine. In the desensitised state the receptor remains ligand-bound but functionally inactive. This is not so much a problem for natural transmitters such as acetylcholine and choline since these are substrates for very powerful breakdown (acetylcholinesterase) and clearance (choline transporter) mechanisms. These transmitter breakdown/clearance mechanisms are likely to maintain the balance between activatible and desensitised α7 nAChRs in a physiologically useful range (Dani et al. 2000). However, synthetic agonists, which are not substrates for the natural breakdown and clearance mechanisms are perceived to have a potential liability both for over-stimulation and also to push the α7 nAChR population equilibrium towards a persistently desensitised state, which is undesirable in disorders in which deficiencies in α7 nAChR expression or function play a role. Agonists by their nature must target the ACh binding pocket which is highly conserved across the different nicotinic receptor subtypes leading to the potential for adverse reactions by non-specific activation of other nicotinic receptor subtypes. Therefore, to avoid these potential liabilities an alternative therapeutic strategy to α7 agonism is to enhance receptor responsiveness to the natural agonists with a positive allosteric modulator (PAM). A PAM is defined as an agent which binds to a site distinct from the agonist binding site, and therefore is not expected to have agonist or desensitisation properties, but enhances the responsiveness of the α7 nAChR to the natural transmitter. The value of this strategy is that for a given amount of transmitter the magnitude of α7 nAChR response is increased in the presence of the PAM relative to the level of transmission possible in its absence. So for disorders in which there is a deficit in α7 nAChR protein the PAM-induced increase in α7 nicotinergic transmission can be beneficial. As a PAM relies on the presence of the natural transmitter the potential for over-stimulation is limited by the breakdown/clearance mechanisms for the natural transmitter.

It is accordingly an object of the present invention to provide methods of treatment that include administering either a positive modulator as the only active substance, thus modulating the activity of endogenous nicotinic receptor agonists such as acetylcholine or choline, or administering a positive modulator together with a nicotinic receptor agonist. In a particular form of this aspect of the invention, the method of treatment comprises treatment with a positive modulator of the α7 nicotinic receptor as described herein and an α7 nicotinic receptor agonist or partial agonist. Examples of suitable compounds with α7 nicotinic receptor agonistic activity include 1,4-Diazabicyclo[3.2.2]nonane-4-carboxylic acid, 4-bromophenyl ester, monohydrochloride (a.k.a SSR180711A);

(−)-spiro[1-azabicyclo[2.2.2.]octane-3,5'-oxazolidine]-2'-one;

3-[(2,4-Dimethoxy)Benzylidene]-Anabaseine Dihydrochloride (a.k.a GTS-21);

[N-[(3R)-1-Azabicyclo[2.2.2]oct-3-yl]-4-chlorobenzamide Hydrochloride] a.k.a PNU-282987)

Positive nAChR modulators of the present invention are useful for treatment or prophylaxis of psychotic disorders, intellectual impairment disorders or diseases or conditions in which modulation of α7 nicotinic receptor activity is beneficial. A particular aspect of the method of the invention is a method of treatment for learning deficit, cognition deficit, attention deficit or memory loss, modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic function, including loss of cholinergic synapses, including jetlag, nicotine addiction, pain.

In view of the above described pharmacological properties, the compounds of formula (I), (I'), (I") or (I''') or any subgroup thereof, their N-oxides, pharmaceutically acceptable addition salts, quaternary amines and stereochemically isomeric forms, may be used as a medicine. In particular, the present compounds can be used for the manufacture of a medicament for treatment or prophylaxis of psychotic disorders, intellectual impairment disorders or diseases or conditions in which modulation of the α7 nicotinic receptor is beneficial.

In view of the utility of the compounds of formula (I), (I'), (I") or (I'''), there is provided a method of treating warm-blooded animals, including humans, suffering from or a method of preventing warm-blooded animals, including humans, to suffer from diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Mild Cognitive Impairment, Attention Deficit Hyperactivity Disorder, Parkinson's disease, Huntington's disease, Tourette's syndrome, brain trauma, jetlag, nicotine addiction and pain. More especially the compounds are suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; anxiety disorders; mental retardation; pervasive developmental disorders; attention deficit disorders, disruptive behaviour disorders; tic disorders; substance dependence; substance abuse; substance withdrawal. Even more in particular for the treatment of diseases in which modulation of the α7 nicotinic receptor is beneficial, including Mild Cognitive Impairment and related syndromes, vascular dementia, post-encephalitic dementia, Mild Cognitive Impairment, Attention deficit Hyperactivity, anxiety, schizophrenia, mania, manic depression, jetlag, bipolar mood disorder and schizoaffective disorder. In an even further embodiment for the treatment of diseases in which modulation of the α7 nicotinic receptor is beneficial, including Mild Cognitive Impairment and related syndromes, vascular dementia, post-encephalitic dementia, Attention deficit Hyperactivity, anxiety, schizophrenia, mania, manic depression, jetlag, bipolar mood disorder and schizoaffective disorder.

Said methods comprise the administration, i.e. the systemic or topical administration, preferably oral administration, of an effective amount of a compound of formula (I), (I'), (I") or (I'''), a N-oxide form, a pharmaceutically acceptable addition salt, a quaternary amine or a possible stereoisomeric form thereof, to warm-blooded animals, including humans.

One skilled in the art will recognize that a therapeutically effective amount of the PAM's of the present invention is the amount sufficient to modulate the activity of the α7 nicotinic receptor and that this amount varies inter alia, depending on the type of disease, the concentration of the compound in the therapeutic formulation, and the condition of the patient. Generally, an amount of PAM to be administered as a therapeutic agent for treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Mild Cognitive Impairment, Attention Deficit Hyperactivity Disorder, Parkinson's disease, Huntington's disease, Tourette's syndrome, brain trauma, jetlag, nicotine addiction and pain will be determined on a case by case by an attending physician.

Generally, a suitable dose is one that results in a concentration of the PAM at the treatment site in the range of 0.5 nM to 200 µM, and more usually 5 nM to 20 µM. To obtain these treatment concentrations, a patient in need of treatment likely will be administered between 0.01 mg/kg to 250 mg/kg body weight, in particular from 0.1 mg/kg to 50 mg/kg body weight. The amount of a compound according to the present invention, also referred to here as the active ingredient, which is required to achieve a therapeutically effect will be, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Mild Cognitive Impairment, Attention Deficit Hyperactivity Disorder, Parkinson's disease, Huntington's disease, Tourette's syndrome, brain trauma, jetlag, nicotine addiction and pain. Said compositions comprising a therapeutically effective amount of a compound of formula (I), (I'), (I") or (I''') and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof. The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of formula (I), (I'), (I") or (I'") used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be coadministered, either in concomitant therapy or in a fixed combination.

In one embodiment, the compounds of formula (I), (I'), (I") or (I'") may also be used in combination with other conventional α7 nicotinic receptor agonists, such as for example 1,4-Diazabicyclo[3.2.2]nonane-4-carboxylic acid, 4-bromophenyl ester, monohydrochloride (a.k.a SSR180711A); (−)-spiro[1-azabicyclo[2.2.2.]octane-3,5'-oxazolidine]-2'- one; 3-[(2,4-Dimethoxy)Benzylidene]-Anabaseine Dihydrochloride (a.k.a GTS-21); or [N-[(3R)-1-Azabicyclo[2.2.2]oct-3-yl]-4-chlorobenzamide Hydrochloride] a.k.a PNU-282987). Thus, the present invention also relates to the combination of a compound of formula (I), (I'), (I") or (I''') and a α7 nicotinic receptor agonist. Said combination may be used as a medicine. The present invention also relates to a product containing (a) a compound of formula (I), (I'), (I") or (I'''), and (b) a α7 nicotinic receptor agonist, as a combined preparation for simultaneous, separate or sequential use in the treatment of diseases wherein modulation of the α7 nicotinic receptor is beneficial, in particular in for the treatment of a range of disorders involving reduced cholinergic function such as learning deficit, cognition deficit, attention deficit or memory loss. The different drugs may be combined in a single preparation together with pharmaceutically acceptable carriers.

In a second embodiment, the compounds of formula (I), (I'), (I") or (I''') may also be used in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, Zolpidem, and salts thereof, and combinations thereof, and the like, or the subject compound may be administered in conjunction with the use of physical methods such as with light therapy or electrical stimulation.

In a third embodiment, the compounds of formula (I), (I'), (I") or (I''') may also be used in combination with anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, [alpha]-adrenoreceptor antagonists, neurokinin-1 receptor antagonists, atypical anti-depressants, benzodiazepines, 5-HTiA agonists or antagonists, especially 5-HTiA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

REFERENCES

Adler et al. 1982. Biol Pysch 44, 98-106
Banerjee et al. 2000, Neurobiol of Disease, 10, 666-672
Bickford and Wear, 1995. Brain Res 705, 235-240
Burghaus et al. 2000, Mol Brain Res, 76, 385-388
Dalack et al. 1998. Am J Psych 11, 1490-1501
Dani et al. 2002, Eur. J. Pharmacology, 393 31-38
Freedman et al. 1995, Biol Psychiatry, 38, 22-33
Freedman et al. 1997, PNAS, 94, 587-592
Hamill et al. 1981, Pfugers Archs 391, 85-100
Guan et al. 1999, Neuroreport, 10, 1779-1782
Griffith et al. 1998. Biol Pysch 44, 98-106
Leonard et al. 2002, Arch Gen Psychiatry, 59, 1085-1095
Marutle et al. 2001, J Chemical Neuroanatomy, 22, 115-126
Ray et al. 2005, Neurobiol of Disease, 19, 366-377
Ridley et al. 2001, Br J Pharmacol, 133, 1286-1295
Virginio et al. 2002, Eur J Pharmacol 445, 153-161

EXPERIMENTAL PART

Hereinafter, the term 'MP' stands for melting point, the term 'c.p.' stands for chemically pure, the term 'p.a.' stands for pro analyse, 'q.s.' means sufficient quantity, 'THF' means tetrahydrofuran, 'CH$_2$Cl$_2$' means dichloromethane, 'MgSO$_4$' means magnesium sulphate, 'Et$_3$N' means triethylamine, 'EtOAc' means ethyl acetate, 'DMF' means N,N-dimethylformamide, 'DIPE' means diisopropyl ether, 'CH$_3$CN' means acetonitrile, 'DMSO' means dimethylsulfoxide, 'LiBH$_4$' means lithium tetrahydroborate, 'DPPA' means phosphorazidic acid diphenyl ester, 'EtOH' means ethanol, 'NaHCO$_3$' means carbonic acid monosodium salt, 'Na$_2$SO$_4$' means sulfuric acid disodium salt, 'NaCl' means sodium chloride, 'HOAc' means acetic acid, 'Et$_2$O' means diethyl ether, 'K$_2$CO$_3$' means potassium carbonate, 'HBTU' means 1-[bis(dimethylamino)methylene]-1H-Benzotriazoliumhexafluorophosphate(1-)3-oxide, 'NaCN' means sodium cyanide, 'HCl' means hydrochloric acid. 'MeOH' means methanol.

A. Preparation of the Intermediates

Example A1 a) Preparation of Intermediate 1

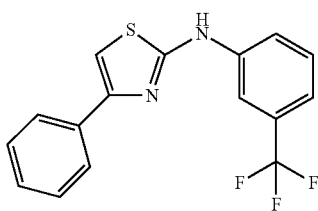 [SMILES: FC(F)(F)c1cccc(Nc2nc(-c3ccccc3)cs2)c1]

A mixture of 2-bromo-1-phenylethanone (0.0402 mol) and [3-(trifluoromethyl)phenyl]-thiourea (0.0402 mol) in EtOH (q.s.) was stirred 4 hours at 70° C. The solvent was evaporated. The residue was triturated under EtOH, filtered off, treated with diluted ammonium hydroxide, then extracted twice with CH$_2$Cl$_2$. The separated organic layer was dried (MgSO$_4$), filtered and the solvent evaporated, yielding 6.75 g (52%) of intermediate 1.

b) Preparation of Intermediate 2

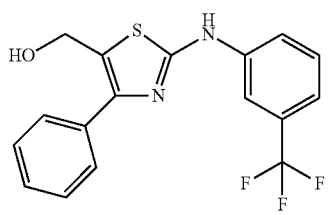 [SMILES: OCc1sc(Nc2cccc(C(F)(F)F)c2)nc1-c1ccccc1]

A mixture of intermediate 1 (0.0062 mol), a 40% aqueous formaldehyde solution (20 ml) and Et$_3$N (5 ml) in THF (20 ml) was reacted for 30 minutes at 140° C. in a microwave oven, then cooled. Diluted ammonia was added and extracted with EtOAc (2×) and dried. The residue was triturated from a small amount of CH$_2$Cl$_2$, filtered off and dried, yielding 1.36 g of intermediate 2 (analytically pure material).

c) Preparation of Intermediate 3

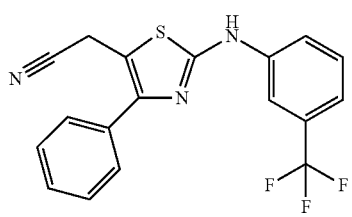 [SMILES: N#CCc1sc(Nc2cccc(C(F)(F)F)c2)nc1-c1ccccc1]

Intermediate 2 (0.00143 mol) was stirred in a 30% HBr/HOAc solution (20 ml) for 25 minutes. Toluene (±100 ml) was added to the reaction mixture and the solvent was evaporated. Toluene (100 ml) was added and azeotroped on the rotary evaporator. A solution of NaCN (0.00285 mol) in DMF (15 ml; previously stirred for 10 minutes) was added to the residue and rinsed with DMF (5 ml). The reaction mixture was stirred for 10 minutes at room temperature. The reaction was quenched by addition of a saturated aqueous Na$_2$CO$_3$ solution (±75 ml). This mixture was extracted with Et$_2$O/DIPE, then DIPE. The combined organic layers were washed with water, dried (MgSO$_4$), filtered and the solvent was evaporated. The residue was purified by flash column chromatography over a Biotage 25 cartridge (eluent: 20%, 30% EtOAc/hexane). The pure product fractions were collected and the solvent was evaporated. The residue (amber oil) crystallised upon standing. The solid was stirred in cyclohexane, filtered off and dried, yielding 0.128 g of intermediate 3 (MP: 121-122° C.).

Example A2 a) Preparation of Intermediate 4

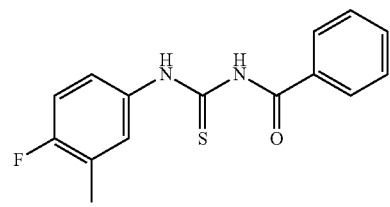 [SMILES: Cc1cc(NC(=S)NC(=O)c2ccccc2)ccc1F]

A solution of benzoyl isothiocyanate (0.068 mol) in THF (50 ml) was added dropwise to a solution of 4-fluoro-3-methylbenzenamine (0.068 mol) in THF (150 ml). The reaction mixture was stirred overnight at room temperature. The solvent was evaporated. The residue was suspended in DIPE, filtered off, washed and dried (vacuum) yielding intermediate 4.

b) Preparation of Intermediate 5

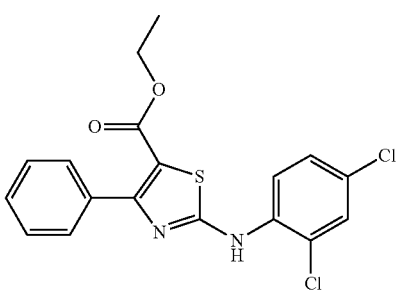 [SMILES: CCOC(=O)c1sc(Nc2ccc(Cl)cc2Cl)nc1-c1ccccc1]

A mixture of intermediate 4 (0.055 mol) and a 1M NaOH solution (0.06 mol) in EtOH (500 ml) was stirred and refluxed for 1 hour. The reaction mixture was cooled and the solvent was evaporated. The residue was suspended in H$_2$O, filtered off, washed and dried (vacuum), yielding 9.8 g (97%) of intermediate 5.

Example A3 a) Preparation of Intermediate 6

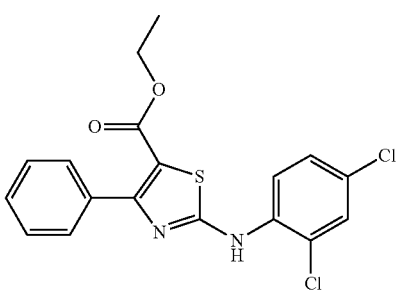 [SMILES: CCOC(=O)c1sc(Nc2ccc(Cl)cc2Cl)nc1-c1ccccc1]

N,N,N-trimethylbenzenaminium tribromide (0.01 mol) was added to a solution of β-oxo-benzenepropanoic acid ethyl ester (0.01 mol) in THF (50 ml), then the mixture was stirred for 4 hours at room temperature, filtered and the filtrate was evaporated. The obtained residue was dissolved in EtOH (50 ml) and (2,4-dichlorophenyl)-thiourea (0.01 mol) was added. The reaction mixture was warmed and then was stirred and refluxed overnight. The solvent was evaporated and the residue was purified by column chromatography (eluent: CH$_2$Cl$_2$). The purest product fractions were collected and the solvent was evaporated. The residue was crystallised from DIPE, then the resulting precipitate was filtered off and dried, yielding 0.050 g (1%) of intermediate 6 (MP: 150° C.).

Example A4 a) Preparation of Intermediate 7

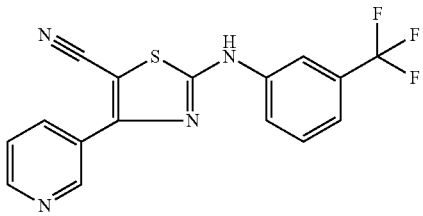 [SMILES: N#Cc1sc(Nc2cccc(C(F)(F)F)c2)nc1-c1cccnc1]

A mixture of α-bromo-β-oxo-3-pyridinepropanenitrile (0.0045 mol) and [3-(trifluoromethyl)phenyl]-thiourea (0.0045 mol) in EtOH (40 ml) was stirred and refluxed for 4 hours; then stirred overnight. The solvent was evaporated. The residue was dissolved in 2-propanone. The solvent was evaporated. The residue was taken up in CH$_2$Cl$_2$ and alkalized with a concentrated ammonium hydroxide solution. The separated organic layer was dried, filtered and the solvent was evaporated. This fraction (0.8 g) was dissolved in 2-propanol and acidified with HCl/2-propanol. The precipitate was filtered off and dried. This fraction (0.2 g, 11%) was crystallised from 2-propanol/EtOH. The precipitate was filtered off and dried, yielding 0.15 g of intermediate 7 as a hydrochloride salt (.HCl).

b) Preparation of Intermediate 8

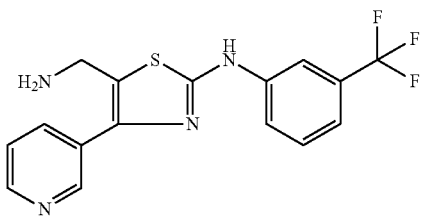 [SMILES: NCc1sc(Nc2cccc(C(F)(F)F)c2)nc1-c1cccnc1]

A mixture of intermediate 7 (0.0137 mol), NH$_3$/MeOH (7N) (100 ml) and THF (p.a.) (50 ml) was hydrogenated at 14° C. with Raney Nickel (1 g) as a catalyst. After uptake of H$_2$ (2 equiv.), the catalyst was filtered off and the filtrate was evaporated. The residue was stirred in CH$_3$CN (25 ml), filtered off, washed with CH$_3$CN and with DIPE, then dried at 50° C. (vac.), yielding 1.86 g (38.7%) of intermediate 8.

Example A5 a) Preparation of Intermediate 9

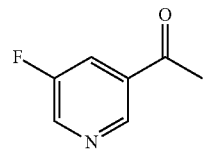

Et$_3$N (0.22 mol) and dimethyl malonate (14 g) were added to a slurry of magnesium chloride (0.06 mol) in toluene (90 ml) (exothermic). The reaction mixture was stirred at room temperature for 2 hours. Then, a solution of 5-fluoro-3-pyridinecarbonyl chloride (0.09 mol) in a small amount of toluene was added within 30 minutes. The reaction mixture was stirred at room temperature overnight. The solution was acidified with 1N HCl and this mixture was extracted with DIPE. The organic layer was separated, dried (MgSO$_4$), filtered and the solvent was evaporated. The residue was taken up into DMSO/H$_2$O 200/10 and this mixture was stirred at 160° C. for 2 hours. The reaction mixture was cooled, stirred overnight at room temperature, then diluted with water. This mixture was extracted with EtOAc. The separated organic layer was dried (MgSO$_4$), filtered and the solvent evaporated. The residue was taken up into DIPE and then acidified with HBr/HOAc. A small amount of 2-propanone was added. The solvent was evaporated. The residue was suspended in CH$_3$CN. A solid was formed, then filtered off (direct decomposition into oil), and the filtrate was evaporated, yielding intermediate 9 as a hydrobromide salt (.HBr).

b) Preparation of Intermediate 10

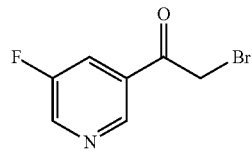 [SMILES: O=C(CBr)c1cncc(F)c1]

Intermediate 9 (0.016 mol) was dissolved in a 48% HBr solution (40 ml), giving Solution (I). Bromine (0.016 mol) was dissolved in a small amount of a 48% HBr solution, giving solution (II). Solution (II) was added dropwise to solution (I) at room temperature. The reaction mixture was stirred for 2 hours at 70° C., then stirred at room temperature overnight. The solvent was evaporated, yielding intermediate 10 as a hydrobromide salt (.HBr).

Example A6 a) Preparation of Intermediates 11 and 12

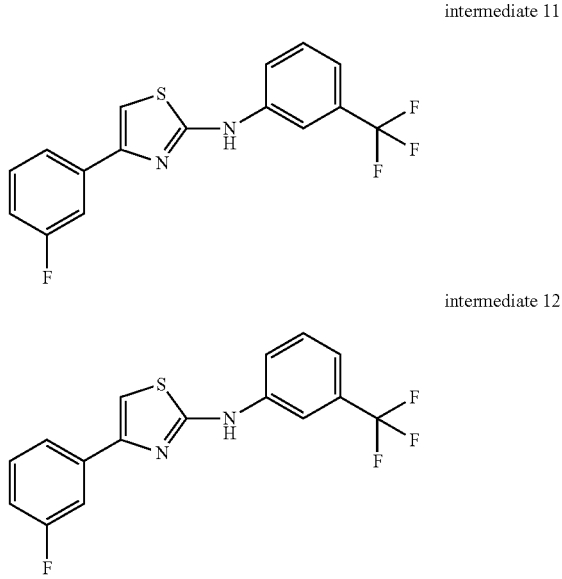

intermediate 11 intermediate 12

A mixture of 2-bromo-1-(3-fluorophenyl)ethanone (0.004 mol) and [3-(trifluoromethyl)phenyl]-thiourea (0.004 mol) in EtOH (40 ml) was stirred and refluxed for 16 hours. The solvent was evaporated and the mixture was dissolved in $CH_2Cl_2$ and an aqueous $Na_2CO_3$-solution. The aqueous layer was extracted with $CH_2Cl_2$. The combined separated organic layers were dried ($MgSO_4$) and the solvent was evaporated. The residue was purified by column chromatography on a biotage system (eluent: $CH_2Cl_2$/hexane 30/70). The product fractions were collected and the solvent was evaporated. The obtained intermediate 11 was dissolved in $CH_3CN$ and a mixture of 2-propanol/HCl was added until pH 1. This mixture was stirred for 20 minutes and then filtered, washed with DIPE and dried (60° C., 72 hours, vacuum), yielding 0.57 g (38%; white powder) of intermediate 12 as a hydrochloride salt (.HCl).

Example A7 a) Preparation of Intermediate 13

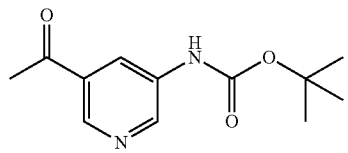 [SMILES: CC(=O)c1cncc(NC(=O)OC(C)(C)C)c1]

A mixture of 5-acetyl-3-pyridinecarboxylic acid (0.02 mol) in 2-butyl-2-propanol (100 ml) was stirred and heated to 60° C. $Et_3N$ (0.06 mol) was added dropwise and the reaction mixture was further heated until 90° C. Then DPPA (0.02 mol) was slowly added dropwise at 90° C. The reaction mixture was stirred at 90° C. overnight. The reaction mixture was then cooled and the solvent was evaporated. The residue was taken up in $H_2O$ and extracted with $CH_2Cl_2$. The separated organic layer was dried ($MgSO_4$), filtered and the solvent was evaporated. The residue was purified over silica gel on a glass filter (eluent: $CH_2Cl_2$/MeOH 98/2). The product fractions were collected and the solvent was evaporated, yielding 1.8 g of intermediate 13.

b) Preparation of Intermediate 14

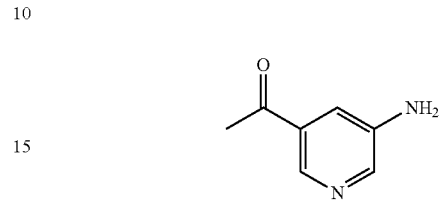

To a mixture of intermediate 13 (0.006 mol) in EtOH (40 ml), a 36% HCl solution (c.p.) (1.6 ml) was added dropwise. The reaction mixture was stirred and refluxed for 4 hours and then stirred at room temperature overnight. The mixture was diluted with $H_2O$ and made alkaline with $Na_2CO_3$. The aqueous layer was extracted with $CH_2Cl_2$ and the separated organic layer was dried ($MgSO_4$), filtered and the solvent was evaporated. The residue was taken up in 2-propanone/HBr and HOAc. The formed solid was filtered off, washed and dried (vacuum), yielding 0.35 g of intermediate 14.

c) Preparation of Intermediate 15

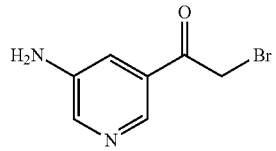 [SMILES: Nc1cncc(C(=O)CBr)c1]

A mixture of intermediate 14 (0.0016 mol) in a 48% HBr solution (20 ml) was stirred and heated to 60° C. Then a solution of bromine (0.0016 mol) in a little bit of a 48% HBr solution was added dropwise. The reaction mixture was stirred at room temperature overnight. The solvent was evaporated, yielding intermediate 15 as a hydrobromide salt (.2HBr).

Example A8 a) Preparation of Intermediate 16

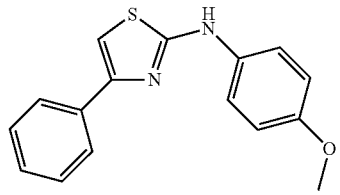 [SMILES: COc1ccc(Nc2nc(-c3ccccc3)cs2)cc1]

A mixture of (4-methoxyphenyl)-thiourea (0.0615 mol) and 2-bromo-1-phenylethanone (0.0615 mol) in EtOH (615 ml) was stirred and refluxed for one hour. The resulting precipitate was filtered off and dried, yielding 15.3 g (68%) of intermediate 16 as a hydrobromide salt (.HBr).

Example A9 a) Preparation of Intermediate 17

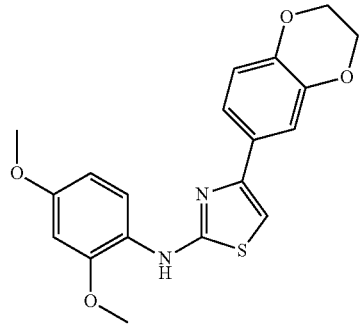 [SMILES: COc1ccc(Nc2nc(-c3ccc4c(c3)OCCO4)cs2)c(OC)c1]

2-Bromo-1-(2,3-dihydro-1,4-benzodioxin-6-yl)-ethanone (0.0169 mol) and (2,4-dimethoxyphenyl)-thiourea (0.0169 mol) were dissolved in EtOH (80 ml). The resultant reaction solution was stirred and refluxed for 4 hours, then cooled to room temperature. The resulting precipitate was filtered off, washed with EtOH (40 ml) and with EtOAc (80 ml), then stirred in a saturated aqueous $NaHCO_3$ solution (100 ml) for 30 minutes. The mixture was filtered. The filter residue was washed with water (100 ml), with EtOAc (40 ml), then dried, yielding 3.25 g (51%) of intermediate 17.

Example A10 a) Preparation of Intermediate 18

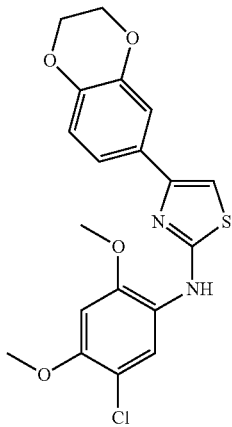 [SMILES: COc1cc(OC)c(Nc2nc(-c3ccc4c(c3)OCCO4)cs2)cc1Cl]

2-Bromo-1-(2,3-dihydro-1,4-benzodioxin-6-yl)-ethanone (0.0337 mol) and (5-chloro-2,4-dimethoxyphenyl)-thiourea (0.0337 mol) were dissolved in EtOH (160 ml). The resultant reaction solution was stirred and refluxed for 4 hours, then cooled to room temperature. The resulting precipitate was filtered off, washed with EtOH (100 ml) and with EtOAc (200 ml), then stirred in a saturated aqueous $NaHCO_3$ solution (200 ml) for 30 minutes. The mixture was filtered. The filter residue was washed with water (200 ml), with EtOAc (100 ml), then dried, yielding 13.0 g (96%) of intermediate 18.

b) Preparation of Intermediate 19

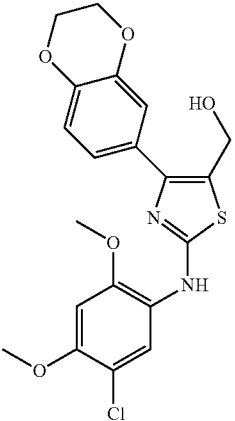 [SMILES: COc1cc(OC)c(Nc2nc(-c3ccc4c(c3)OCCO4)c(CO)s2)cc1Cl]

Intermediate 18 (0.00124 mol), $Et_3N$ (1.2 ml), formaldehyde (6 ml, 40%) and THF (6 ml) were transferred into a microwave tube. The reaction mixture was heated for 3 minutes at 120° C. in a microwave oven. The reaction was quenched by adding aqueous ammonia. The layers were separated. The aqueous phase was extracted with EtOAc. The organic layer was separated, washed with brine, dried ($Na_2SO_4$), filtered and the solvent was evaporated under reduced pressure. The residue was purified by column chromatography over silica gel. The product fractions were collected and the solvent was evaporated, yielding 4 g (75%) of intermediate 19.

c) Preparation of Intermediate 20

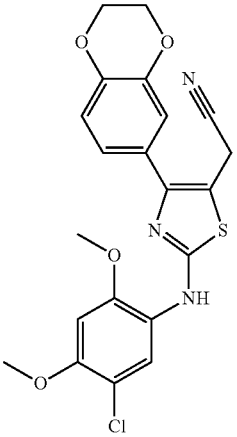 [SMILES: COc1cc(OC)c(Nc2nc(-c3ccc4c(c3)OCCO4)c(CC#N)s2)cc1Cl]

Intermediate 19 (0.001 mol) was co-evaporated with dry THF (10 ml) in vacuo. The residue was dissolved in dry $CH_2Cl_2$ (10 ml). The mixture was cooled on a dry-ice/2-propanone bath. Trimethylsilanecarbonitrile (0.012 mol) was added. $BF_3.Et_2O$ (0.0032 mol) was added dropwise over 15 minutes. The reaction mixture was stirred for 30 minutes on the dry ice/2-propanone bath, then warmed to room temperature and stirred for another 2 hours at room temperature. A saturated aqueous $NaHCO_3$ solution (20 ml) was added. $CH_2Cl_2$ (30 ml) was added and shaken. The organic layer was separated, washed with a saturated aqueous NaCl solution (20 ml), dried (anh. $Na_2SO_4$), filtered and the solvent was evaporated in vacuo. The residue was purified by column chromatography over silica gel (eluent: dilution system of $CH_2Cl_2$). The product fractions were collected and the solvent was evaporated, yielding 0.09 g (20%) of intermediate 20.

Example A11 a) Preparation of Intermediate 21

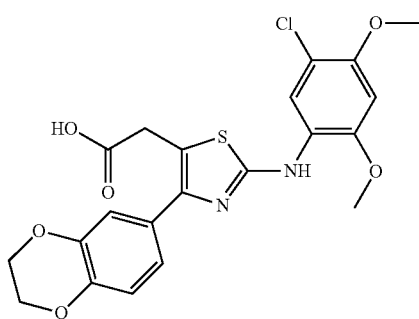 [SMILES: COc1cc(OC)c(Nc2nc(-c3ccc4c(c3)OCCO4)c(CC(=O)O)s2)cc1Cl]

Intermediate 20 (0.0014 mol) was dissolved in a mixture of HOAc (30 ml), $H_2O$ (15 ml) and concentrated HCl (15 ml). The resultant reaction mixture was stirred and refluxed for 1 hour. The solvent was evaporated in vacuo, yielding intermediate 21 (used in next reaction step, without further purification).

Example A12 a) Preparation of Intermediate 22

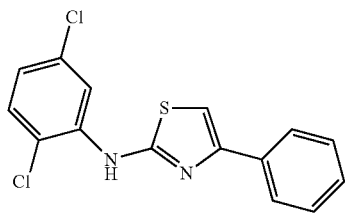 [SMILES: Clc1ccc(Cl)c(Nc2nc(-c3ccccc3)cs2)c1]

A mixture of (2,5-dichlorophenyl)-thiourea and 2-bromo-1-phenylethanone (0.023 mol) in EtOH was stirred and refluxed for 2 hours. The reaction mixture was allowed to cool, then the precipitate was filtered off and dried, yielding 6.43 g (87%, MP: 221.4° C. to 225.3° C.) of intermediate 22 as a hydrobromide salt (.HBr).

b) Preparation of Intermediate 23

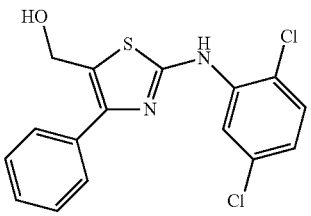 [SMILES: OCc1sc(Nc2cc(Cl)ccc2Cl)nc1-c1ccccc1]

A mixture of intermediate 22 (0.0156 mol) in a 40% aqueous formaldehyde solution (20 ml), $Et_3N$ (5 ml) and THF (20 ml) was heated in a microwave to 100° C. and stirred for 1 hour. Then the solvent was evaporated. The residue was taken up with $H_2O$ and extracted with $CH_2Cl_2$. The separated organic layer was dried, filtered and the solvent was evaporated. The residue was purified over silica gel by glass filter (eluent: $CH_2Cl_2$/MeOH 99/1, 98/2, 96/4 and 94/6). The product fractions were collected and the solvent was evaporated. The residue was taken up in EtOH. The precipitate was filtered off and dried, yielding 1.79 g (33%; MP: from 172.8° C. to 175.0° C.) of intermediate 23.

Example A13 a) Preparation of Intermediate 24

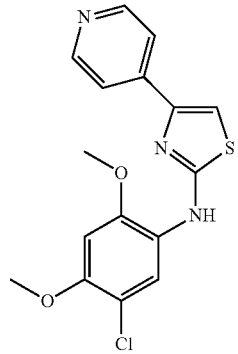 [SMILES: COc1cc(OC)c(Nc2nc(-c3ccncc3)cs2)cc1Cl]

A mixture of 2-bromo-1-(4-pyridinyl)-ethanone, hydrobromide (0.02 mol) and (5-chloro-2,4-dimethoxyphenyl)-thiourea (0.02 mol) in EtOH (200 ml) was stirred and refluxed for 4 hours, then cooled to room temperature. The resulting precipitate was filtered off, washed with EtOH and dried, yielding 6.0 g (60%) of intermediate 24 as a hydrobromide salt (.HBr).

b) Preparation of Intermediate 25

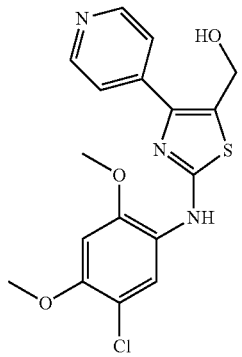 [SMILES: COc1cc(OC)c(Nc2nc(-c3ccncc3)c(CO)s2)cc1Cl]

A mixture of intermediate 24 (0.00098 mol), $Et_3N$ (1.2 ml), formaldehyde (6 ml) and THF (6 ml) was introduced into a 40-ml microwave-tube. The reaction mixture was heated for 30 minutes at 130° C. in a microwave oven. The reaction mixtures were combined, then quenched by adding aqueous ammonia (20 ml), then stirred. The layers were separated. The aqueous phase was extracted with EtOAc (2×20 ml). The organic layers were combined, washed with brine (2×10 ml), dried (MgSO$_4$), filtered and the solvent was evaporated in vacuo. The residue was purified by column chromatography over silica gel (eluent: CH$_2$Cl$_2$/MeOH 30/1). The product fractions were collected and the solvent was evaporated, yielding 2.45 g (65%) of intermediate 25.

Example A14 a) Preparation of Intermediate 26

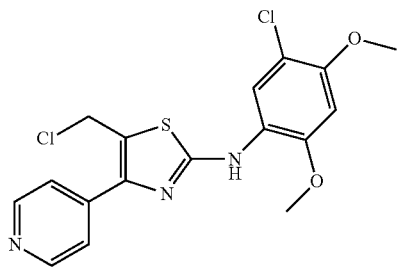 [SMILES: COc1cc(OC)c(Nc2nc(-c3ccncc3)c(CCl)s2)cc1Cl]

Intermediate 25 (0.00053 mol) was suspended in 4N HCl/dioxane (20 ml). The suspension was stirred overnight. The solvent was evaporated in vacuo, yielding intermediate 26.

Example A15 a) Preparation of Intermediate 27

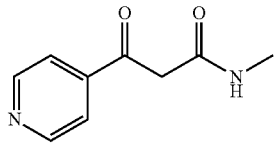

A mixture of β-oxo-4-pyridinepropanoic acid, ethyl ester (0.006 mol) and methanamine (q.s.) was stirred and refluxed (100° C.) for 30 minutes in a microwave oven. This mixture was cooled, then extracted with CH$_2$Cl$_2$. The organic layer was separated, dried (Na$_2$SO$_4$), filtered and the solvent was evaporated in vacuo, yielding (crude, used in next reaction step, without further purification) intermediate 27.

Example A16 a) Preparation of Intermediate 28

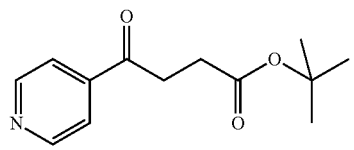 [SMILES: CC(C)(C)OC(=O)CCC(=O)c1ccncc1]

4-Pyridinecarboxaldehyde (0.44 mol) in DMF (150 ml) was added drop wise in 5 minutes to a mixture of NaCN (0.106 mol) in DMF (200 ml). The reaction mixture was stirred for 5 minutes. Then 1,1-dimethylethyl ester 2-propenoic acid (0.423 mol) in DMF (350 ml) was added drop wise in 10 minutes. The reaction mixture was refluxed for 4 hours. Then H$_2$O was added. The mixture was extracted with Et$_2$O. The separated organic layer was washed with saturated NaHCO$_3$ aqueous solution. The separated organic layer was dried, filtered and the solvent was evaporated. The residue was purified by column chromatography over silica gel (eluent: CH$_2$Cl$_2$/MeOH 99/1, 98.5/1.5 and 98/2). The product fractions were collected and the solvent was evaporated, yielding 69 g (70%) of intermediate 28.

b) Preparation of Intermediate 29

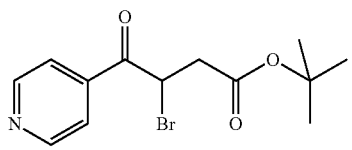 [SMILES: CC(C)(C)OC(=O)CC(Br)C(=O)c1ccncc1]

A mixture of intermediate 28 (0.0213 mol) and bromine (4 eq) in EtOH (100 ml) was stirred for 2 hours at room temperature and for 5 hours at reflux. The solvent was evaporated, yielding 5 g (75%) of intermediate 29.

c) Preparation of Intermediate 30

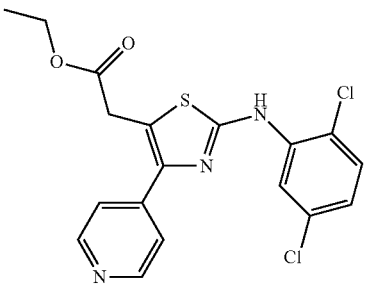 [SMILES: CCOC(=O)Cc1sc(Nc2cc(Cl)ccc2Cl)nc1-c1ccncc1]

A mixture of intermediate 29 (0.003 mol) and (2,5-dichlorophenyl)-thiourea (0.003 mol) in EtOH (100 ml) was stirred at reflux for 2 hours. The precipitate (4.75 g) was filtered off and dried. The mother liquor was left to stand and resulted in new product crystallization. This precipitate was filtered off and dried, yielding 2.22 g (80%; MP: 156.8° C.-163.5° C.) of intermediate 30.

d) Preparation of Intermediate 31

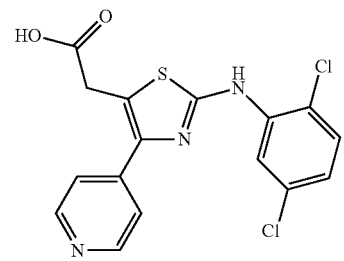 [SMILES: O=C(O)Cc1sc(Nc2cc(Cl)ccc2Cl)nc1-c1ccncc1]

A mixture of intermediate 30 (0.0025 mol) in HCl/Dioxane (25 ml) and H$_2$O (25 ml) was stirred overnight at 50° C. The solvent was evaporated. The residue was dried, yielding 1 g (100%) of intermediate 31 as a hydrochloride salt (.HCl).

Example A17 a) Preparation of Intermediate 32

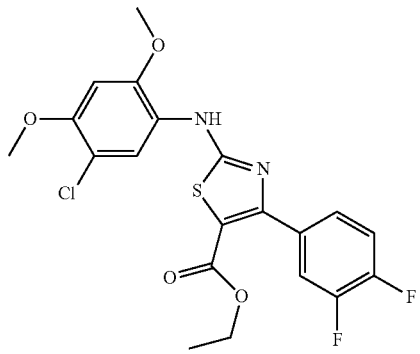 [SMILES: CCOC(=O)c1sc(Nc2cc(Cl)c(OC)cc2OC)nc1-c1ccc(F)c(F)c1]

Sulfuryl chloride (0.0007 mol) was added to 3,4-difluoro-β-oxo-benzenepropanoic acid, ethyl ester (0.00066 mol) in $CH_2Cl_2$ (5 ml). The mixture was stirred for 2 hours at room temperature. The solvent was evaporated in vacuo. (5-Chloro-2,4-dimethoxyphenyl)-thiourea (0.0006 mol) was added to the residue, followed by addition of EtOH (5 ml). The resultant reaction mixture was stirred and refluxed for 2 hours, then cooled to room temperature. The resulting precipitate was filtered off, washed with EtOH, and dried, yielding 0.200 g of intermediate 32.

Example A18 a) Preparation of Intermediate 33

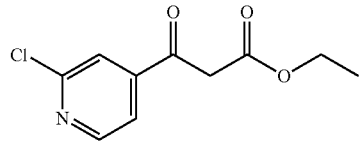

2-Chloro-4-pyridinecarboxylic acid (0.0635 mol) was dissolved in THF (25 ml) and $CH_3CN$ (25 ml). 1,1'-Carbonylbis-1H-Imidazole (0.0698 mol) was added to the solution and stirred for 2.5 hours at room temperature to result in reaction mixture (A). Magnesium chloride (0.095 mol) and $Et_3N$ (0.1905 mol) were added to a solution of monoethyl ester propanedioic acid, potassium salt (0.0667 mol) in $CH_3CN$ (50 ml) while ice-cooling. The reaction mixture was stirred for 5 hours at room temperature. Then reaction mixture (A) was added to the reaction mixture and stirred for 15 hours at room temperature. The mixture was poured in ice-water. This mixture was acidified with HCl (concentrated) to pH=5 to pH=6. This mixture was extracted with EtOAc. The separated organic layer was dried ($Na_2SO_4$), filtered and the solvent was evaporated. The residue was purified by column chromatography. The product fractions were collected and the solvent was evaporated, yielding 10 g (69%) of intermediate 33.

b) Preparation of Intermediate 34

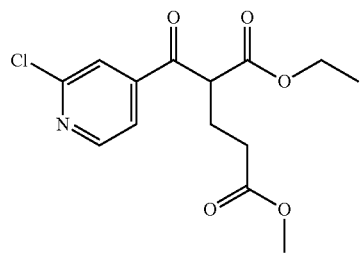 [SMILES: CCOC(=O)C(CCC(=O)OC)C(=O)c1ccnc(Cl)c1]

A mixture of intermediate 33 (0.04393 mol) and EtOH, sodium salt (0.08786 mol) in EtOH (100 ml) was heated for 3 hours at 80° C. The reaction mixture was cooled. 3-Bromopropanoic acid methyl ester (0.04393 mol) was added drop wise to the reaction mixture and stirred overnight at 50° C. The residue was purified by column chromatography. The product fractions were collected and the solvent was evaporated, yielding 9.6 g (72%) of intermediate 34.

c) Preparation of Intermediate 35

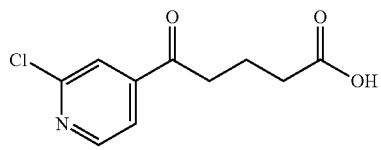 [SMILES: O=C(O)CCCC(=O)c1ccnc(Cl)c1]

A mixture of intermediate 34 (0.02913 mol) in concentrated HCl (50 ml) was heated at reflux for 3 hours. The solvent was evaporated (vacuo) and the residue was dried, yielding 5.5 g (71%) of intermediate 35 as a hydrochloride salt (.HCl).

d) Preparation of Intermediate 36

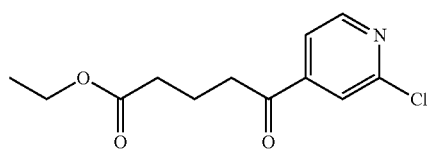 [SMILES: CCOC(=O)CCCC(=O)c1ccnc(Cl)c1]

A mixture of intermediate (0.02083 mol) in HCl/EtOH (100 ml) was stirred overnight. The solvent was evaporated (vacuo), yielding 6 g (98%) of intermediate 36 as s hydrochloride salt (.HCl).

e) Preparation of Intermediate 37

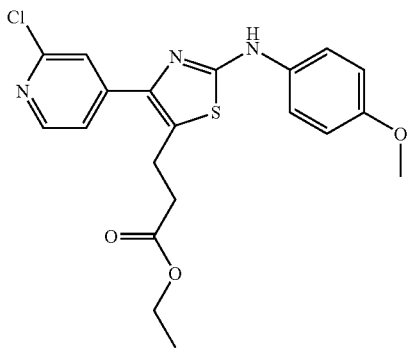 [SMILES: CCOC(=O)CCc1sc(Nc2ccc(OC)cc2)nc1-c1ccnc(Cl)c1]

A mixture of intermediate 36 (0.00018 mol) and N,N,N-tributyl-1-butanaminium (tribromide) (0.00078 mol) in THF (20 ml) was refluxed for 2 hours. The solvent was evaporated. (4-Methoxyphenyl)-thiourea (0.00117 mol) and EtOH (20 ml) were added to the residue and then refluxed for 2 hours. The solvent was evaporated. The residue was partitioned between NaHCO$_3$ saturated aqueous solution and EtOAc. The separated organic layer's solvent was evaporated. The residue was purified by TLC (eluens: petroleum ether/EtOAc 2:1), yielding 0.080 g (24%) of intermediate 37.

B. Preparation of the Compounds

Example B1

Preparation of Compound 1

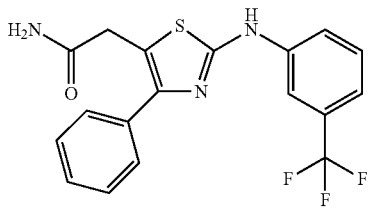 [SMILES: NC(=O)Cc1sc(Nc2cccc(C(F)(F)F)c2)nc1-c1ccccc1]

Intermediate 3 (0.00017 mol) was dissolved in 2-propanone (2 ml). H$_2$O (2 ml) was added, followed by addition of urea-hydrogen peroxide (CAS no.: [124-43-6]) (0.00068 mol), then K$_2$CO$_3$ (0.00009 mol). The reaction mixture was stirred overnight at room temperature. Then, more K$_2$CO$_3$ (0.006 g) was added and the reaction mixture was stirred overnight at room temperature. The reaction was quenched with EtOAc. The organic layer was filtered through an Extrelut cartridge, then purified over a Biotage 12 cartridge (eluent: CH$_2$Cl$_2$/MeOH 98/2). The product fractions were collected and the solvent was evaporated. The residue was crystallised from CH$_2$Cl$_2$. The precipitate was filtered off and dried. The crystallization filtrate was purified by flash column chromatography over a Biotage 12 cartridge (eluent: CH$_2$Cl$_2$/MeOH 98/2). The product fractions were collected and the solvent was evaporated. The residue (0.035 g, 57%, off-white solid) was triturated under DIPE, filtered off and dried, yielding 0.023 g of compound 1 (MP: 186-187° C.).

Table F-1 lists the compounds that were prepared according to Examples A1a, A1b, A1c or B1 described earlier. The following abbreviations were used in the table: '.HBr' stands for the hydrobromide salt, '.HCl' stands for hydrochloride salt, 'MP' stands for melting point.

TABLE F-1

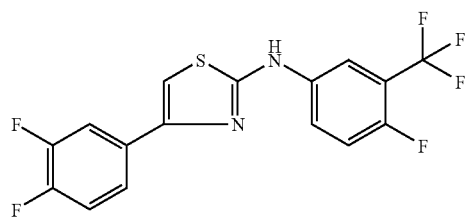

·HBr; Co. No. 11; according to A1a;
MP: 194° C.

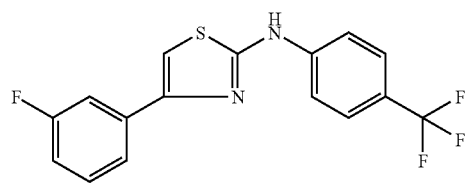

Co. No. 13; according to A1a

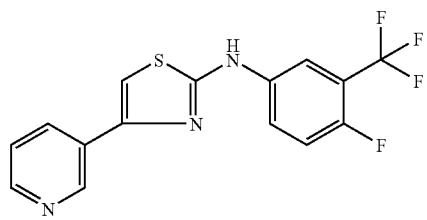

·HBr; Co. No. 14; according to A1a

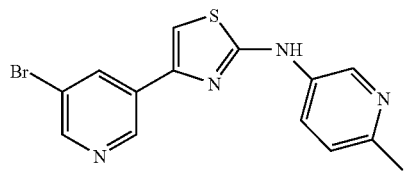

Co. No. 15; according to A1a

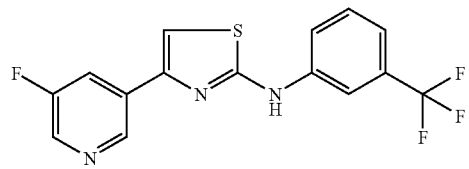

·2HBr; Co. No. 16; according to A1a

TABLE F-1-continued
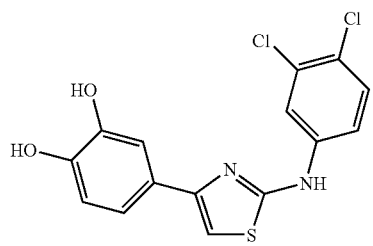
·HCl; Co. No. 17; according to A1a
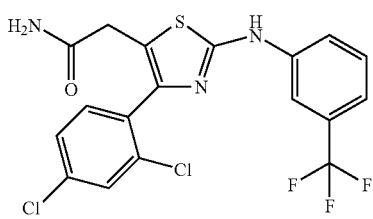
Co. No. 18; according to B1;
MP: 209-211° C.
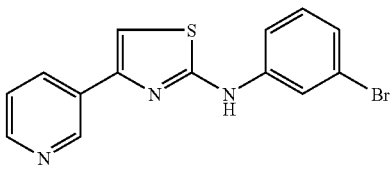
·HBr; Co. No. 19; according to A1a
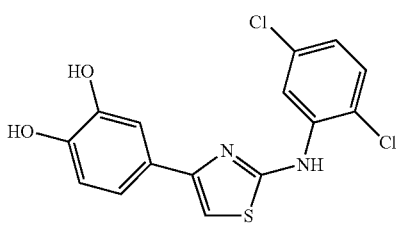
·HCl; Co. No. 21; according to A1a
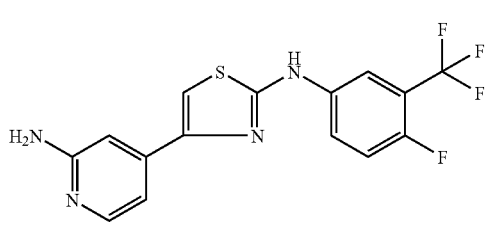
·HBr; Co. No. 22; according to A1a
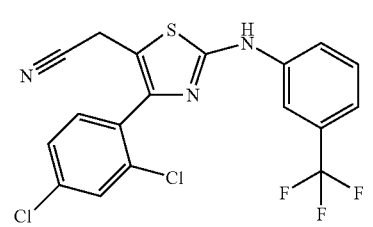
Co. No. 23; according to A1c;
MP: 167-168° C.
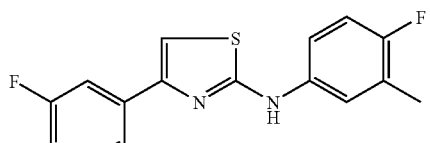
·2HBr; Co. No. 24; according to A1a
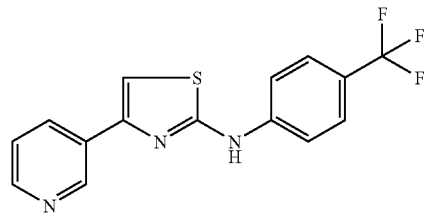
·HBr; Co. No. 25; according to A1a
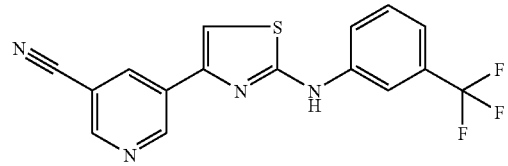
Co. No. 26; according to A1a
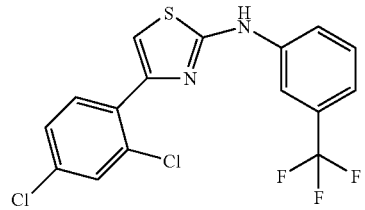
Co. No. 28; according to A1a
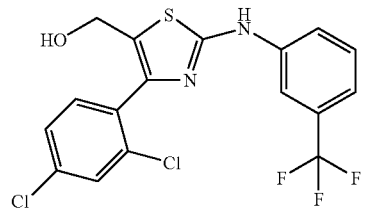
Co. No. 31; according to A1b
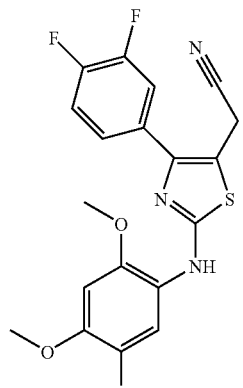
·HBr; Co. No. 112; according to A1c TABLE F-1-continued

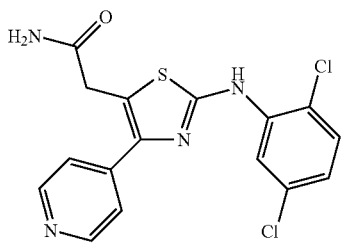

Co. No. 113; according to B1

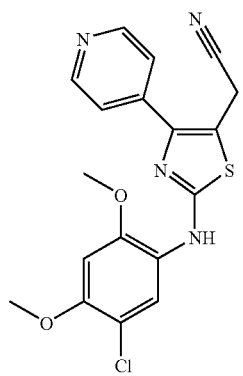

Co. No. 114; according to A1c

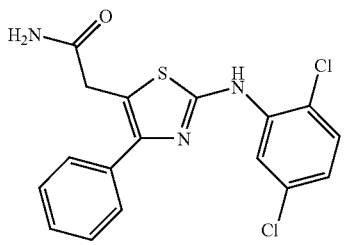

Co. No. 115; according to B1; MP: 189.5-192.7° C.

Example B2

Preparation of Compound 2

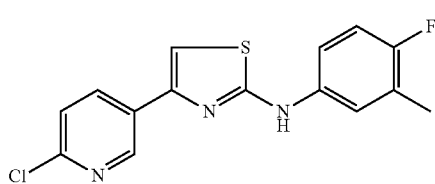 [SMILES: Cc1cc(Nc2nc(-c3ccc(Cl)nc3)cs2)ccc1F]

1-(6-Chloro-3-pyridinyl)ethanone (0.005 mol) in THF (p.a.) (100 ml) was stirred at room temperature. N,N,N-trimethylbenzenaminium tribromide (0.005 mol) was added portionwise over 1 hour. The mixture was stirred for 1 hour at room temperature. The precipitate was filtered off and washed with THF (p.a.) (50 ml). Intermediate 5 (0.005 mol) was added portionwise to the filtrate. The reaction mixture was stirred overnight at room temperature. The solvent was evaporated. The residue was stirred in 2-propanone (p.a.). The precipitate was filtered off and dried. The residue (0.96 g) was taken up in $H_2O$, alkalized and extracted with $CH_2Cl_2$. The separated organic layer was dried, filtered and the solvent was evaporated. The crude product was purified by column chromatography over silica gel (eluent: $CH_2Cl_2/(MeOH/NH_3)$ 98/2), then purified by column chromatography over silica gel (eluent: $CH_2Cl_2/(MeOH/NH_3)$ 99/1) and finally recrystallised from $CH_3CN$, yielding 0.35 g (22%) of compound 2 (MP: 175° C.).

Table F-2 lists the compounds that were prepared according to Example B2 described above. The following abbreviations were used in the table: '.HCl' stands for hydrochloride salt, '.HBr' stands for hydrobromide salt, 'MP' stands for melting point.

TABLE F-2

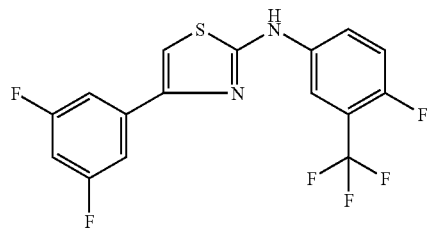

•HCl; Co. No. 29; MP: 154° C.

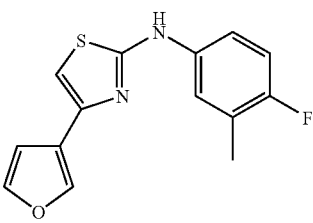

•HCl; Co. No. 30; MP: 162° C.

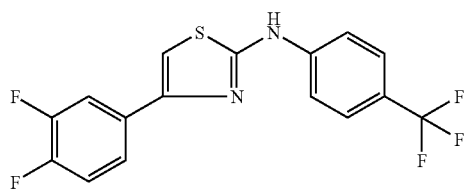

•HBr; Co. No. 20

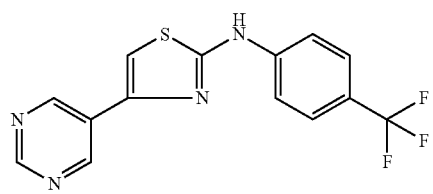

•HBr; Co. No. 27; MP: >260° C.

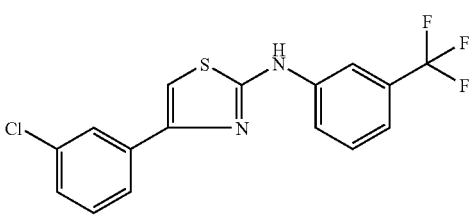

•HBr; Co. No. 12

Example B3

Preparation of Compound 3

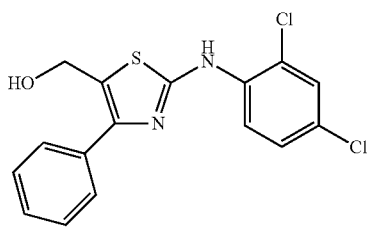 [SMILES: OCc1sc(Nc2ccc(Cl)cc2Cl)nc1-c1ccccc1]

LiBH$_4$, 2M in THF (5 equiv, 0.00331 mol) was added to intermediate 6 (0.000661 mol) in dry THF (15 ml), stirred at room temperature under N$_2$ atmosphere. The reaction mixture was stirred for 6 days at 60° C. The reaction was quenched with 1N NaOH and the mixture was stirred for 2 days. This mixture was extracted with EtOAc (2×). The separated organic layer was dried (MgSO$_4$), filtered and the solvent evaporated. The residue was purified by flash column chromatography over a Biotage 25M cartridge (eluent: EtOAc/hexane 3/7). The product fractions were collected and the solvent was evaporated, yielding 0.059 g (25%) of compound 3.

Table F-3 lists the compounds that were prepared according to Example B3 described above.

TABLE F-3

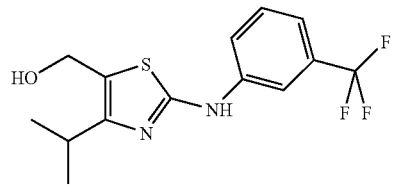

Co. No. 161;

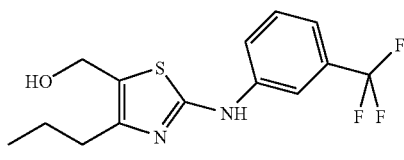

Co. No. 117;

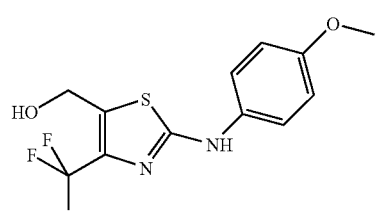

Co. No. 118;

TABLE F-3-continued

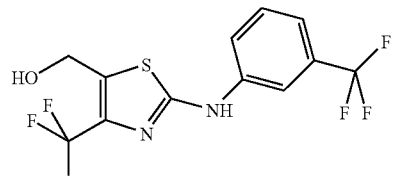

Co. No. 119;

Example B4

Preparation of Compound 4

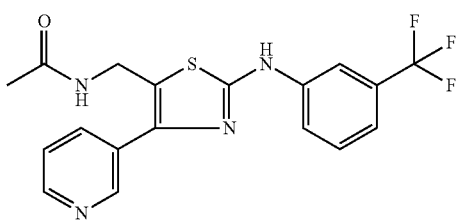 [SMILES: CC(=O)NCc1sc(Nc2cccc(C(F)(F)F)c2)nc1-c1cccnc1]

A mixture of intermediate 8 (0.000856 mol), Et$_3$N (0.0011 mol) and THF (p.a., dried on molecular sieves) (7.5 ml) was stirred on an ice-bath under N$_2$ and a solution of acetyl chloride (0.0011 mol) in THF (p.a., dried on molecular sieves) (2.5 ml) was added dropwise. After addition, the reaction mixture was stirred on an ice-bath for 1.5 hour, poured out into water (30 ml) and then stirred for 15 minutes. The formed solids were filtered off, washed with water and with DIPE. These solids were recrystallised from CH$_3$CN, washed with CH$_3$CN and with DIPE, then dried at 50° C. (vacuum), yielding 0.136 g (40.5%) of compound 4.

Table F-4 lists the compound that was prepared according to Example B4 described above.

TABLE F-4

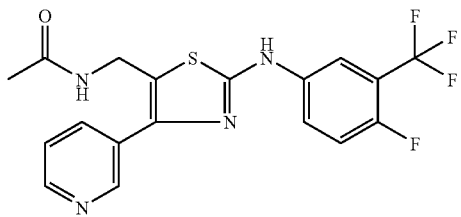

Co. No. 32

Example B5

Preparation of Compound 5

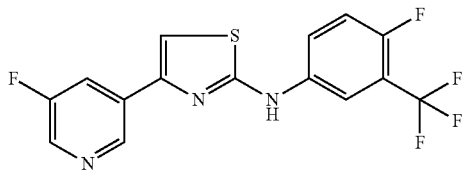 [SMILES: Fc1cncc(-c2csc(Nc3ccc(F)c(C(F)(F)F)c3)n2)c1]

A mixture of intermediate 10 (0.005 mol) and [4-fluoro-3-(trifluoromethyl)phenyl]-thiourea (0.005 mol) in EtOH (50 ml) was stirred and refluxed for 3 hours, then stirred at room temperature overnight. The solvent was evaporated. The residue was suspended in 2-propanone. The precipitate was filtered off, washed and dried in vacuo, yielding 0.8 g of compound 5.

Example B6

Preparation of Compound 6

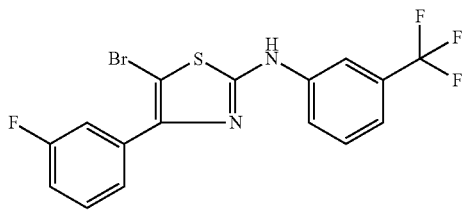 [SMILES: Fc1cccc(-c2nc(Nc3cccc(C(F)(F)F)c3)sc2Br)c1]

A mixture of intermediate 11 (0.005 mol) in N,N-dimethylformamide (15 ml) was stirred at 0° C. and 1-bromo-2,5-pyrrolidinedione (0.005 mol) was added. The reaction mixture was stirred for 3 hours at room temperature and the solvent was evaporated. The residue was stirred in a $Na_2CO_3$ solution and the mixture was extracted with $CH_2Cl_2$. The solvent was evaporated and the residue was purified by column chromatography over silica gel (eluent: $CH_2Cl_2$). The product fractions were collected and the solvent was evaporated. The residue (free base) was then converted into the hydrochloric acid salt (1:1), the resulting precipitate was filtered off and dried, yielding 0.7 g of compound 6 as a hydrochloride salt (.HCl).

Example B7

Preparation of Compound 7

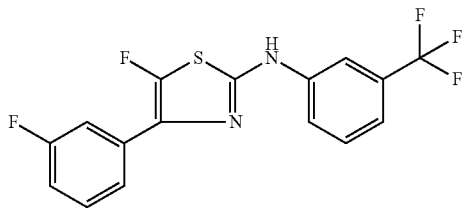 [SMILES: Fc1cccc(-c2nc(Nc3cccc(C(F)(F)F)c3)sc2F)c1]

A mixture of intermediate 11 (0.01 mol) and 2,6-dimethylpyridine (0.01 mol) in N,N-dimethylformamide (50 ml) was stirred at 0° C. and Selectfluor® (0.02 mol) was added portionwise in 1 hour. The reaction mixture was stirred overnight and the solvent was evaporated. The residue was dissolved in $H_2O$ and the mixture was extracted with $CH_2Cl_2$. The organic layer was separated, dried ($MgSO_4$) and the solvent was evaporated. The residue was purified by column chromatography over silica gel. The product fractions were collected and the solvent was evaporated. The residue converted into the hydrochloric acid salt (1:1) with HCl/2-propanol. The resulting precipitate was filtered off and dried, yielding 1.2 g of compound 7 as a hydrochloride salt (.HCl).

Table F-5 lists the compound that was prepared according to Example B7 described above.

TABLE F-5

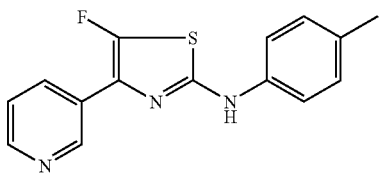

Co. No. 120;

Example B8

Preparation of Compound 8

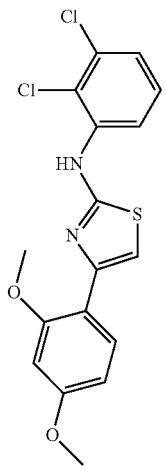 [SMILES: COc1ccc(-c2csc(Nc3cccc(Cl)c3Cl)n2)c(OC)c1]

A mixture of (2,3-dichlorophenyl)-thiourea (0.000067 mol) and 2-bromo-1-(2,4-dimethoxyphenyl)ethanone (0.000080 mol) in DMF (6 ml) was placed in a shaker overnight at 70° C. Unreacted reagents were scavenged with TRIS resin (0.084 g, 0.00027 mol) and bicarbonate resin (0.073 g, 0.00027 mol) over the weekend. The resins were removed by filtration and the filtrates concentrated in vacuo. Impure compounds (LC/MS purity <90%) were purified by reversed phase high-performance liquid chromatography using an ammonium bicarbonate buffer. The product fractions were collected and the organic solvent was evaporated. The aqueous concentrate was extracted. The extract was dried, filtered and the solvent evaporated, yielding 0.012 g (47.0%) of compound 8.

Table F-6 lists the compounds that were prepared according to Example B8 described above.

TABLE F-6

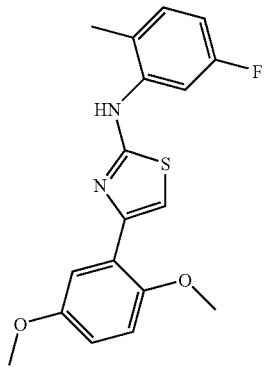

Co. No. 33

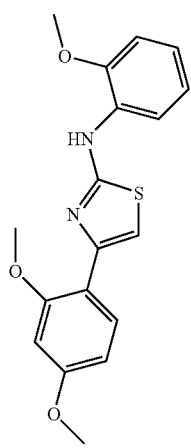

Co. No. 34

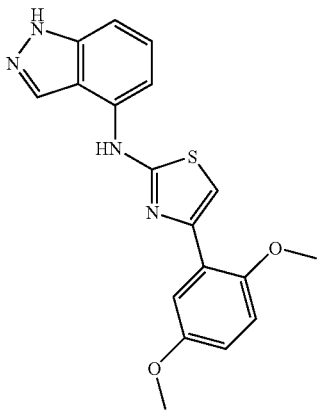

Co. No. 35

TABLE F-6-continued

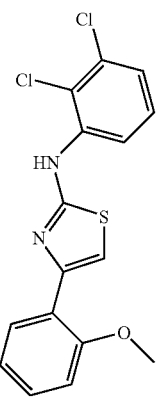

Co. No. 36

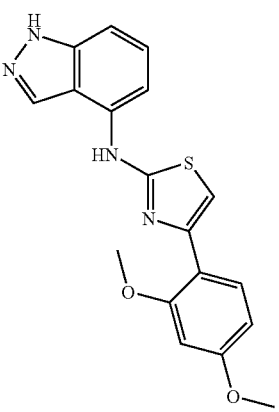

Co. No. 37

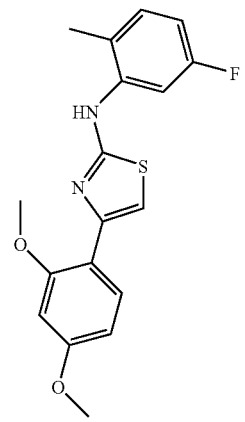

Co. No. 38

TABLE F-6-continued

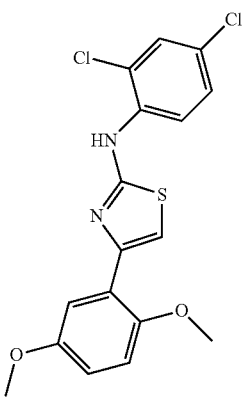

Co. No. 39

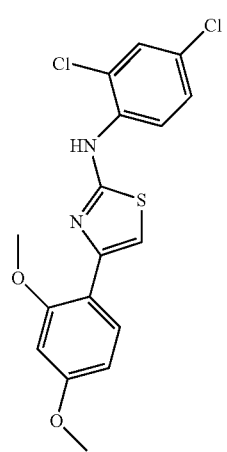

Co. No. 40

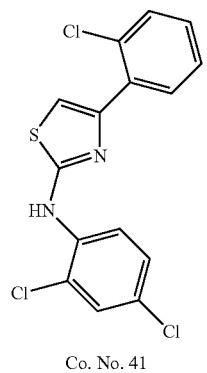 [SMILES: Clc1ccc(Nc2nc(-c3ccccc3Cl)cs2)c(Cl)c1]

Co. No. 41

TABLE F-6-continued

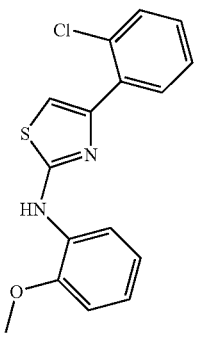

Co. No. 42

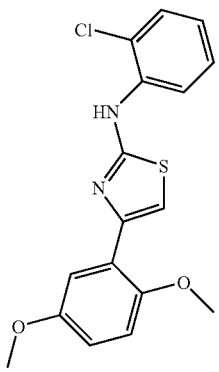

Co. No. 43

Example B9

Preparation of Compound 9

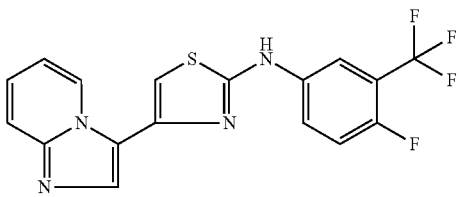 [SMILES: Fc1ccc(Nc2nc(-c3cnc4ccccn34)cs2)cc1C(F)(F)F]

A mixture of 2-chloro-1-imidazo[1,2-a]pyridin-3-yl-ethanone monohydrochloride (0.017 mol) and [4-fluoro-3-(trifluoromethyl)phenyl]-thiourea (0.017 mol) in EtOH (150 ml) was stirred and refluxed for 6 hours; then stirred overnight at room temperature. The precipitate was filtered off. The residue was taken up in EtOH. This mixture was stirred overnight. The precipitate was filtered off, washed and dried (vacuum), yielding compound 9 as a hydrochloride salt (.HCl; MP: 248° C.).

Table F-7 lists the compounds that were prepared according to Example B9 described above. The following abbreviations were used in the table: '.HCl' stands for hydrochloride salt.

TABLE F-7

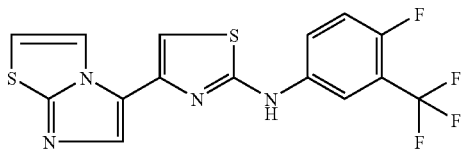

•HCl; Co. No. 44

TABLE F-8

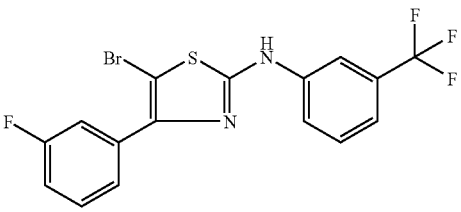

CO. No. 121; •HCl

Example B10

Preparation of Compound 10

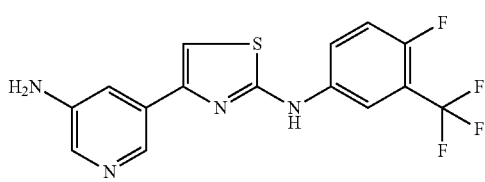 [SMILES: Nc1cncc(-c2csc(Nc3ccc(F)c(C(F)(F)F)c3)n2)c1]

A mixture of intermediate 15 (0.003 mol) and [4-fluoro-3-(trifluoromethyl)phenyl]-thiourea (0.003 mol) in EtOH (30 ml) was stirred and refluxed for 3 hours, then stirred at room temperature for 2 hours. The solvent was evaporated. The residue was taken up into water/EtOH, then alkalized with $Na_2CO_3$, and extracted with $CH_2Cl_2$. The separated organic layer was dried ($MgSO_4$), filtered, and the solvent was evaporated, yielding 1 0.8 g of residue. Part (0.2 g) of this residue was suspended in DIPE, filtered off, washed and dried in vacuo, yielding 0.2 g of compound 10.

Example B11

Preparation of Compound 93

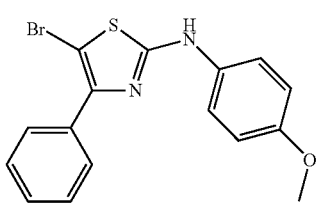 [SMILES: COc1ccc(Nc2nc(-c3ccccc3)c(Br)s2)cc1]

A mixture of intermediate 16 (0.0083 mol) and 1-bromo-2,5-pyrrolidinedione (0.0083 mol) in DMF (30 ml) was stirred for one hour at room temperature. Ice was added. The supernatant was decanted off. The solid residue was stirred in EtOH, filtered off and dried, yielding 1.61 g (54%) of compound 93.

Table F-8 lists the compounds that were prepared according to Example B11 described above. The following abbreviation was used in the table: '.HCl' stands for hydrochloride salt.

Example B12

Preparation of Compound 94

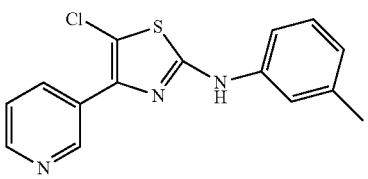 [SMILES: Cc1cccc(Nc2nc(-c3cccnc3)c(Cl)s2)c1]

N-(3-methylphenyl)-4-(3-pyridinyl)-2-thiazolamine (0.00232 mol) was dissolved in DMF (p.a.) (12 ml) and the mixture was cooled with ice-bath. After 30 minutes, 1-chloro-2,5-pyrrolidinedione (0.00233 mol) was added and the reaction mixture was stirred for 1 hour at 0° C. The mixture was allowed to warm to room temperature and was stirred overnight and then concentrated. The residue was triturated under NaOH (1M; 10 ml) and was stirred vigorously for 3 hours and filtered. The precipitate was crystallized from EtOH and was then purified by column chromatography over Hyperprep C18 HS BDS (eluent: (0.5% $NH_4Ac$ in $H_2O/CH_3CN$ 90/10)/MeOH/$CH_3CN$ 75/25/0; 0/50/50; 0/0/100). The product fractions were collected and the solvent was evaporated. The residue was stirred in DIPE. The precipitate was filtered off and dried, yielding 0.042 g of compound 94.

Example B13

Preparation of Compound 95

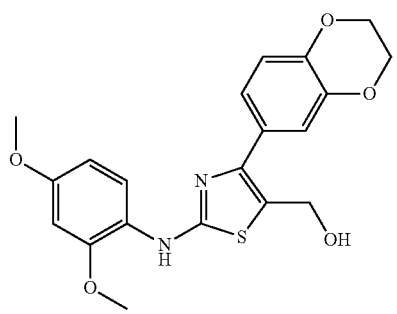 [SMILES: COc1ccc(Nc2nc(-c3ccc4c(c3)OCCO4)c(CO)s2)c(OC)c1]

A mixture of intermediate 17 (0.000676 mol) in a 40% formaldehyde solution (3 ml), THF (3 ml) and $Et_3N$ (1 ml)

was stirred for 6 minutes at 100° C. in a microwave oven. The reaction was quenched by adding aqueous ammonia (20 ml), then stirred for 30 minutes. The mixture was extracted with EtOAc. The organic layer was separated, dried (Na$_2$SO$_4$), filtered and the solvent was evaporated in vacuo. The residue was purified by flash column chromatography over silica gel. The product fractions were collected and the solvent was evaporated, yielding compound 95.

Table F-9 lists the compounds that were prepared according to Example B13 described above. The following abbreviation was used in the table: 'MP' stands for melting point.

TABLE F-9

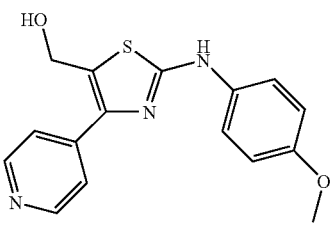

Co. No. 122; MP: 126.2-126.8° C.

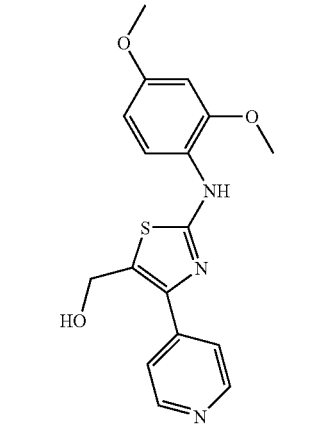

Co. No. 123;

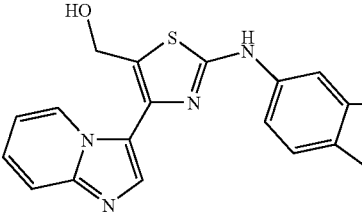

Co. No. 124;

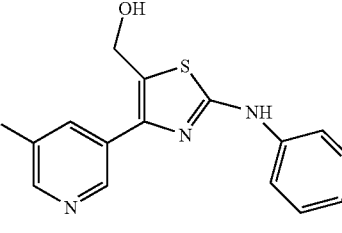

Co. No. 125;

TABLE F-9-continued

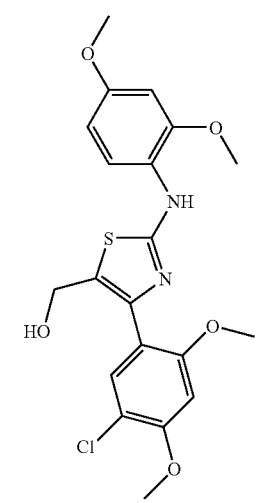

Co. No. 126;

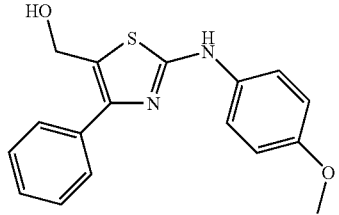

Co. No. 127;

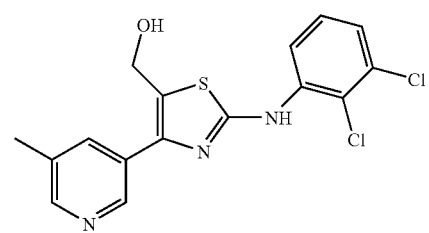

Co. No. 128;

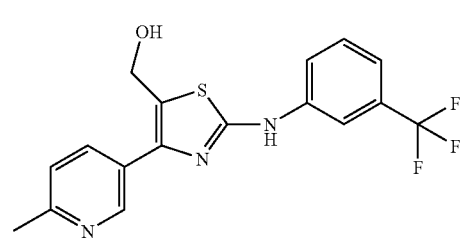

Co. No. 129;

Example B14

Preparation of Compound 96

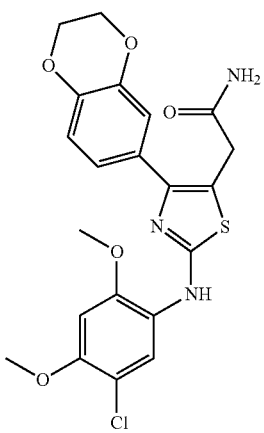 [SMILES: COc1cc(OC)c(Nc2nc(-c3ccc4c(c3)OCCO4)c(CC(N)=O)s2)cc1Cl]

Hydrogen peroxide (2 ml) was added to a mixture of intermediate 20 (0.000341 mol) and NaOH (0.0025 mol) in DMSO (4 ml). The reaction mixture was stirred for 30 minutes at room temperature. The precipitate was filtered off and the filter residue was purified by high-performance liquid chromatography. The product fractions were collected and the solvent was evaporated, yielding 0.100 g of compound 96.

Table F-10 lists the compound that was prepared according to Example B14 described above.

TABLE F-10

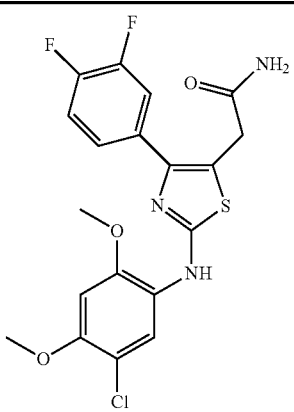

Co. No. 130;

Example B15

Preparation of Compound 97

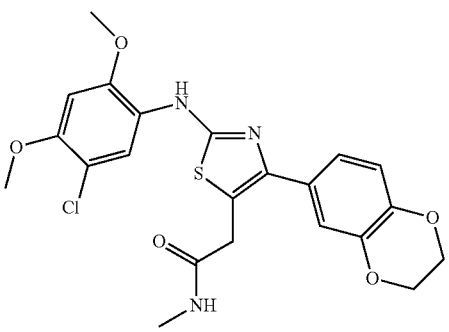 [SMILES: CNC(=O)Cc1sc(Nc2cc(Cl)c(OC)cc2OC)nc1-c1ccc2c(c1)OCCO2]

A mixture of intermediate 21 (0.000433 mol), methanamine, hydrochloride (0.0024 mol), N'-(ethylcarbonimidoyl)-N,N-dimethyl-1,3-propanediamine, monohydrochloride (0.000645 mol), 1-hydroxy-1H-benzotriazole (0.000433 mol) and $K_2CO_3$ (0.0020 mol) in $CH_3CN$ (10 ml) was stirred and refluxed for 2 hours. The reaction mixture was cooled to room temperature. The precipitate was filtered off and the filtrate's solvent was evaporated in vacuo. The residue was purified by preparative high-performance liquid chromatography. The product fractions were collected and the solvent was evaporated, yielding compound 97.

Table F-11 lists the compounds that were prepared according to Example B15 described above. The following abbreviation was used in the table: 'MP' stands for melting point.

TABLE F-11

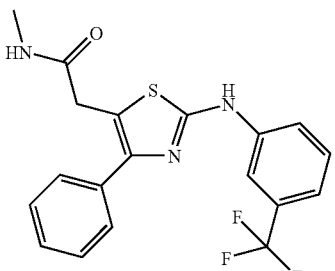

Co. No. 131;

TABLE F-11-continued

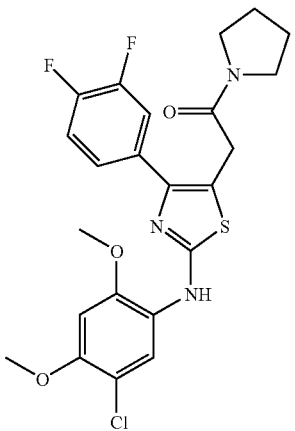

Co. No. 132;

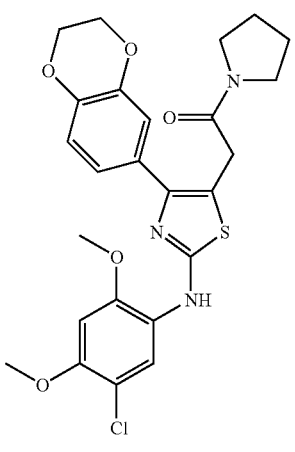

Co. No. 133;

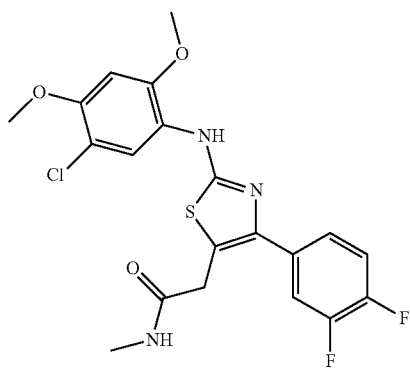

Co. No. 134;

TABLE F-11-continued

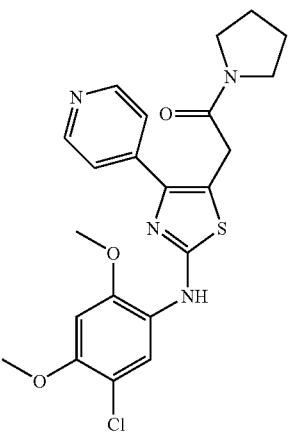

Co. No. 135;

Example B16

Preparation of Compound 98

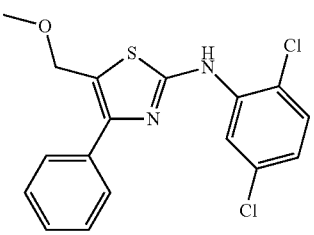 [SMILES: COCc1sc(Nc2cc(Cl)ccc2Cl)nc1-c1ccccc1]

A mixture of intermediate 23 (0.00057 mol), paraform (200 mg) and Pt/C$_5$% (10 mg) in thiophene solution (0.1 ml) and MeOH (50 ml) was hydrogenated at 50° C. Then the solvent was evaporated. The residue was purified by high-performance liquid chromatography (standard gradient elution with NH$_4$HCO$_3$). The product fractions were collected and the solvent was evaporated. Then the residue was dried, yielding 0.034 g (16%; MP: 105.1° C. to 105.5° C.) of compound 98.

Table F-12 lists the compound that was prepared according to Example B16 described above. The following abbreviation was used in the table: 'MP' stands for melting point.

TABLE F-12

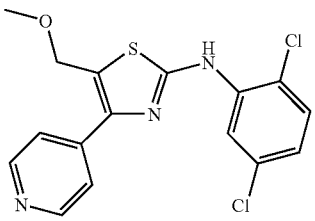

Co. No. 136; MP: 205.3-205.8° C.

Example B17

Preparation of Compound 99

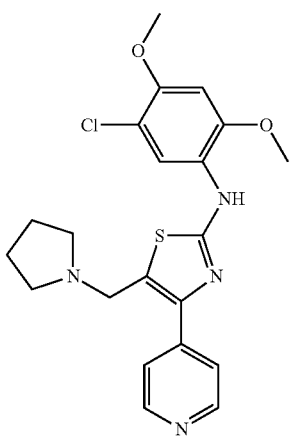 [SMILES: COc1cc(OC)c(Nc2nc(-c3ccncc3)c(CN3CCCC3)s2)cc1Cl]

Intermediate 25 (0.00053 mol) was suspended in 4N HI/Dioxane (20 ml). The suspension was stirred overnight. The solvent was evaporated in vacuo. Pyrrolidine (0.048 mol) was added. The reaction mixture was stirred for 4 hours. A 5% aqueous NaOH solution (10 ml) was added. This mixture was extracted with $CH_2Cl_2$ (2×10 ml). The organic layer was separated, washed with water (10 ml) and with brine (10 ml), dried ($Na_2SO_4$, anhydrous), filtered and the filter residue was washed with $CH_2Cl_2$ (5 ml). The filtrate's solvent was evaporated in vacuo. The residue was purified by high-performance liquid chromatography. The product fractions were collected and the solvent was evaporated, yielding 0.100 g (43.9%) of compound 99.

Example B18

Preparation of Compound 100

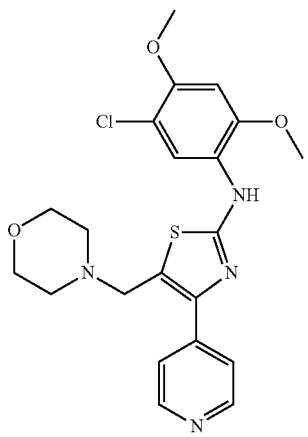 [SMILES: COc1cc(OC)c(Nc2nc(-c3ccncc3)c(CN3CCOCC3)s2)cc1Cl]

Morpholine (0.023 mol) was added to intermediate 25. The reaction mixture was stirred for 4 hours. A 5% aqueous NaOH solution (10 ml) was added. This mixture was extracted with $CH_2Cl_2$ (2×10 ml). The organic layer was separated, washed with water (10 ml) and with brine (10 ml), dried ($Na_2SO_4$, anhydrous), filtered and the filter residue was washed with $CH_2Cl_2$ (5 ml). The filtrate's solvent was evaporated in vacuo. The residue was purified by high-performance liquid chromatography. The product fractions were collected and the solvent was evaporated, yielding 0.060 g (26.8%) of compound 100.

Example B19

Preparation of Compound 101

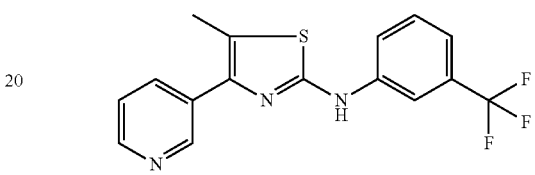

A mixture of 2-bromo-1-(3-pyridinyl)-1-propanone, hydrobromide (0.003 mol) and [3-(trifluoromethyl)phenyl]-thiourea (0.003 mol) in EtOH (150 ml) was stirred and refluxed overnight. The solvent was evaporated. The residue was stirred in 2-propanone and a small amount of EtOH. The precipitate was filtered off and dried in vacuo at 50° C., yielding 0.952 g of compound 101 as a hydrobromide salt (.2HBr).

Table F-13 lists the compounds that were prepared according to Example B19 described above.

TABLE F-13

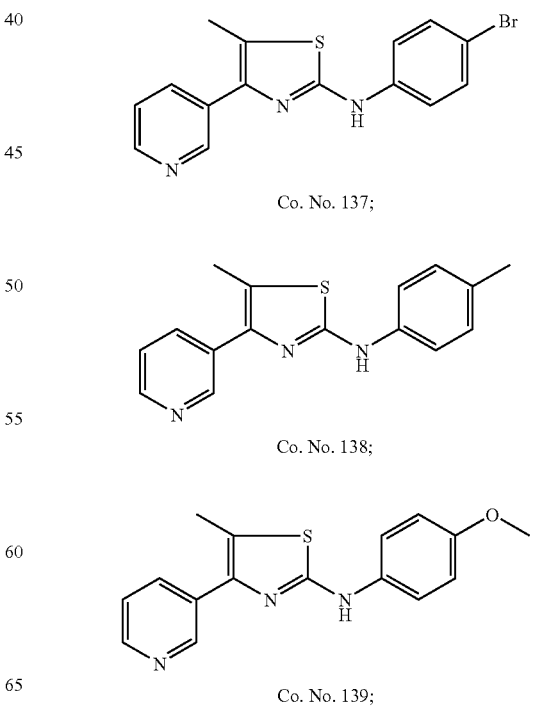

Co. No. 137;

Co. No. 138;

Co. No. 139;

TABLE F-13-continued

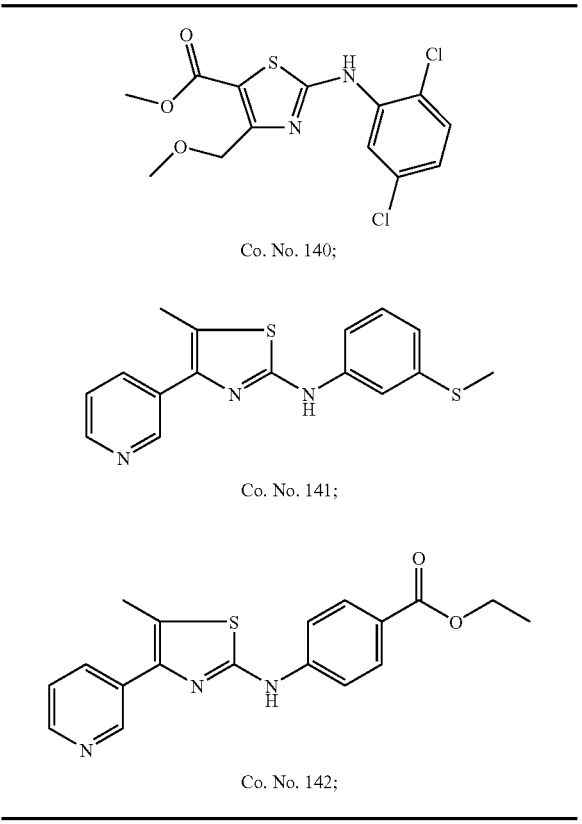

Co. No. 140;

Co. No. 141;

Co. No. 142;

Example B20

Preparation of Compound 102

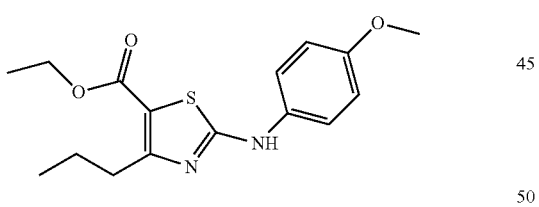

Sulfuryl chloride (0.0055 mol) was added dropwise to a solution of 3-oxo-hexanoic acid, ethyl ester (0.0055 mol) in CH$_2$Cl$_2$ (q.s.). The reaction mixture was stirred for 2 hours at room temperature. The solvent was evaporated. A solution of (4-methoxyphenyl)-thiourea (0.0055 mol) in EtOH (100 ml) was added to the residue. The resultant reaction mixture was stirred and refluxed for 4 hours. A saturated aqueous NaHCO$_3$ solution was added. This mixture was extracted with EtOAc. The separated organic layer was purified by column chromatography over silica gel. The product fractions were collected and the solvent was evaporated, yielding compound 102.

Table F-14 lists the compounds that were prepared according to Example B20 described above.

TABLE F-14

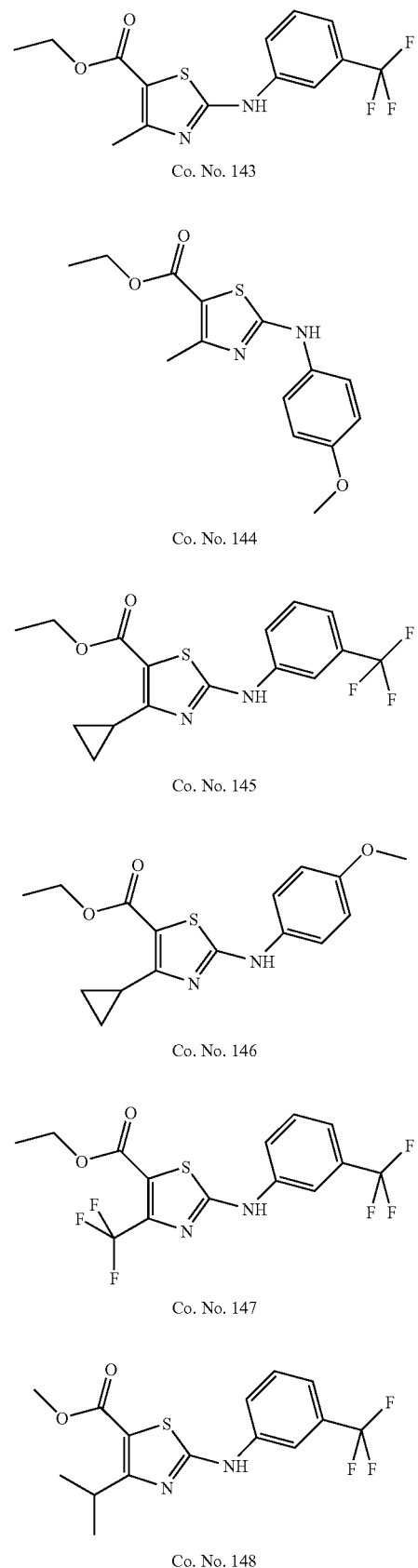

Co. No. 143

Co. No. 144

Co. No. 145

Co. No. 146

Co. No. 147

Co. No. 148

TABLE F-14-continued

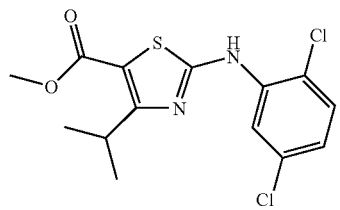

Co. No. 149

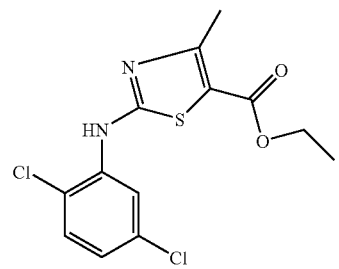

Co. No. 50

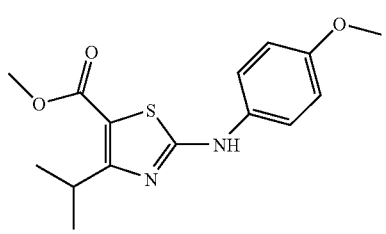

Co. No. 151

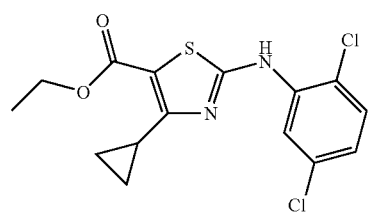

Co. No. 152

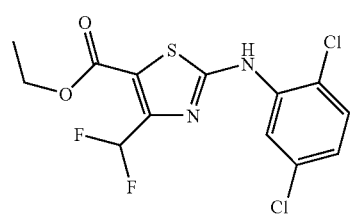

Co. No. 153

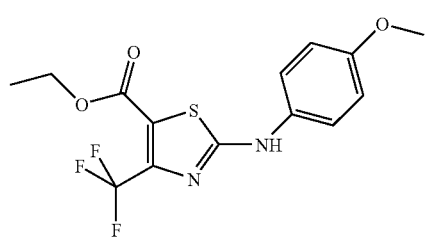

Co. No. 154

TABLE F-14-continued

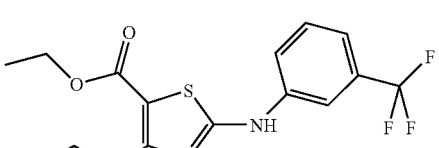

Co. No. 155

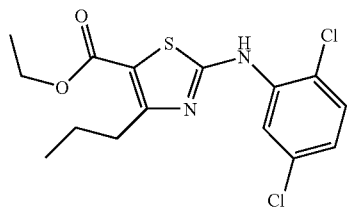

Co. No. 156

Example B21

Preparation of Compound 103

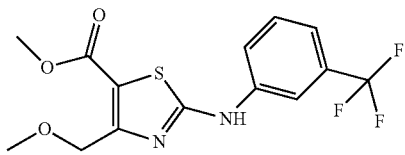 [SMILES: COCc1nc(Nc2cccc(C(F)(F)F)c2)sc1C(=O)OC]

A mixture of 2-chloro-4-methoxy-3-oxo-butanoic acid, methyl ester (0.0069 mol) and [3-(trifluoromethyl)phenyl]-thiourea (0.0069 mol) in EtOH (20 ml) was stirred and refluxed for 4 hours. The solvent was evaporated. The residue was stirred in a saturated aqueous NaHCO$_3$ solution, then extracted with EtOAc. The separated organic layer was purified by column chromatography. The product fractions were collected and the solvent was evaporated, yielding compound 103.

Table F-15 lists the compounds that were prepared according to Example B21 described above.

TABLE F-15

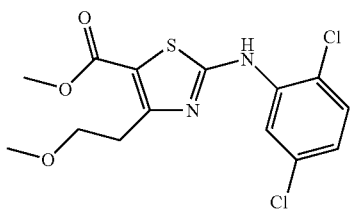

Co. No. 157

TABLE F-15-continued

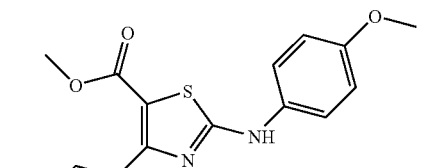

Co. No. 158

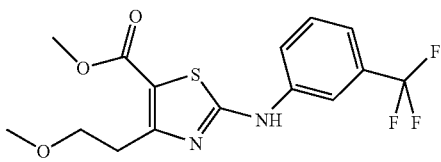

Co. No. 159

Example B22

Preparation of compound 104

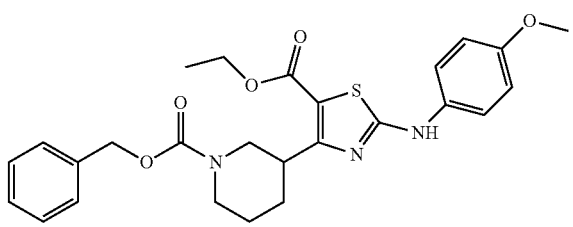 [SMILES: CCOC(=O)c1sc(Nc2ccc(OC)cc2)nc1C1CCCN(C(=O)OCc2ccccc2)C1]

β-Oxo-1-[(phenylmethoxy)carbonyl]-3-piperidinepropanoic acid, ethyl ester (0.0033 mol) and sulfuryl chloride (0.0036 mol) were dissolved in CH$_2$Cl$_2$ (10 ml). The reaction mixture was stirred for 2 hours. The solvent was evaporated in vacuo. This residue and (4-methoxyphenyl)-thiourea (0.0030 mol) were dissolved in EtOH (10 ml) and the resultant reaction mixture was stirred and refluxed for 4 hours, then cooled to room temperature. The mixture was filtered and the filter residue was washed with EtOH (10 ml), then stirred in a saturated aqueous NaHCO$_3$ solution, then filtered off and dried in vacuo, yielding 0.8 g (54%) of compound 104.

Table F-16 lists the compounds that were prepared according to Example B22 described above.

TABLE F-16

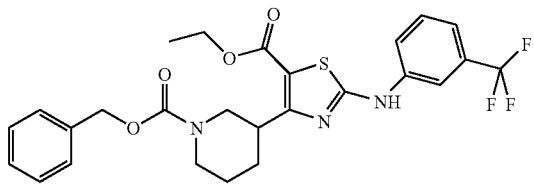

Co. No. 160

Example B23

Preparation of Compound 105

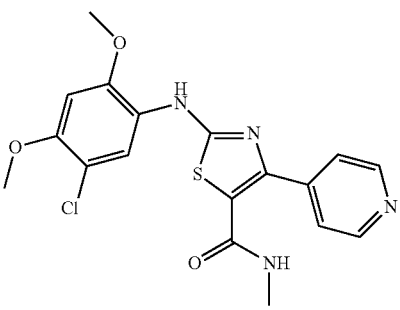 [SMILES: CNC(=O)c1sc(Nc2cc(Cl)c(OC)cc2OC)nc1-c1ccncc1]

Sulfuryl chloride (0.0017 mol) was added to a mixture of intermediate 27 (0.00168 mol) in CH$_2$Cl$_2$ (10 ml). The reaction mixture was stirred for 2 hours. The solvent was evaporated. (5-Chloro-2,4-dimethoxyphenyl)-thiourea (0.0015 mol) was added to the residue, followed by the addition of EtOH (10 ml). The reaction mixture was stirred and refluxed for 4 hours. NaHCO$_3$ (0.3 g) was added and the mixture was stirred for 30 minutes. The resulting precipitate was filtered off and the filtrate's solvent was evaporated. The residue was purified by preparative high-performance liquid chromatography. The product fractions were collected and the solvent was evaporated, yielding compound 105.

Example B24

Preparation of Compound 106

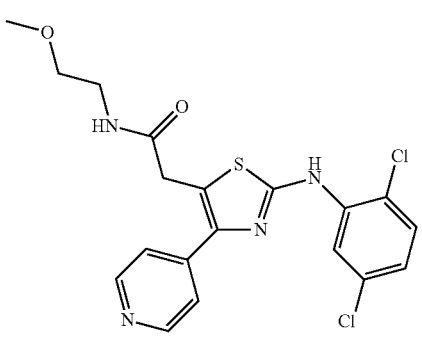 [SMILES: COCCNC(=O)Cc1sc(Nc2cc(Cl)ccc2Cl)nc1-c1ccncc1]

A mixture of intermediate 31 (0.00026 mol) and HBTU (0.00039 mol) in DMF (5 ml) was stirred for 1 hour. 2-Methoxyethanamine (0.00078 mol) was added to the reaction mixture and then stirred for 3 hours at room temperature. The solvent was evaporated. The residue was purified by high-performance liquid chromatography (standard gradient elution with NH$_4$HCO$_3$ buffer). The product fractions were collected and the solvent was evaporated. The residue was dried, yielding 0.045 g (40%; MP: 218.0° C. to 224.2° C.) of compound 106.

Table F-17 lists the compounds that were prepared according to Example B24 described above. The following abbreviation was used in the table: 'MP' stands for melting point.

TABLE F-17

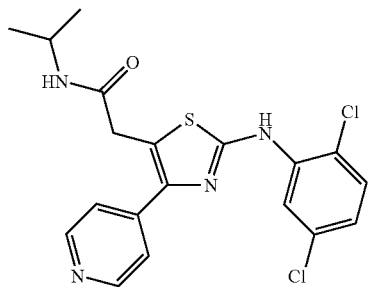

Co. No. 161; MP; 256.1-263.7° C.

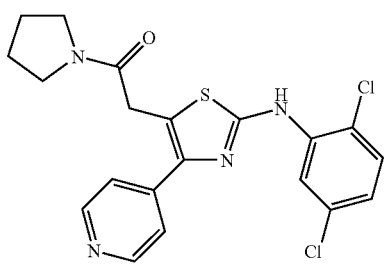

Co. No. 162; MP; 146.7-156.9° C.

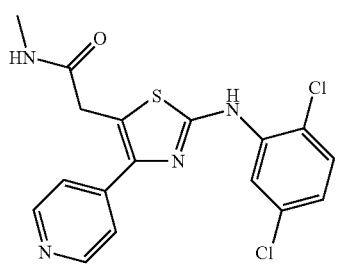

Co. No. 163; MP; 237.2-244.0° C.

Example B25

Preparation of Compound 107

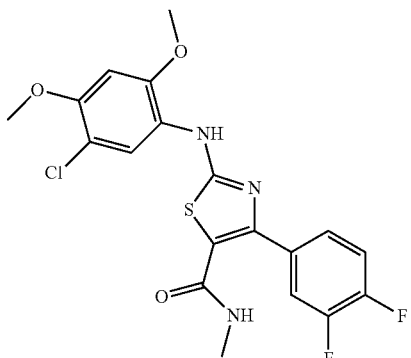

Reaction in microwave oven. A mixture of intermediate 32 (0.00066 mol) in CH$_3$NH$_2$/H$_2$O (20 ml) was heated for one hour at 100° C. The reaction mixture was cooled to room temperature. This mixture was extracted with CH$_2$Cl$_2$. The separated organic layer was dried (Na$_2$SO$_4$), filtered and the solvent evaporated. The residue was purified by high-performance liquid chromatography. The product fractions were collected and the solvent was evaporated, yielding compound 107.

Example B26

Preparation of Compound 108

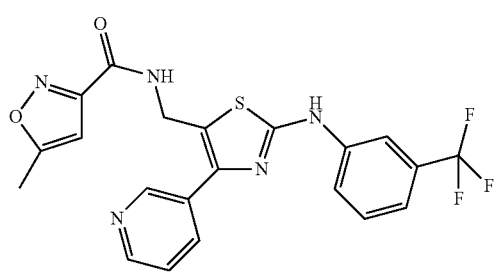 [SMILES: Cc1cc(C(=O)NCc2sc(Nc3cccc(C(F)(F)F)c3)nc2-c2cccnc2)no1]

A mixture of intermediate 8 (0.000285 mol) and 5-methyl-3-isoxazolecarbonyl chloride (0.000285 mol) in Et$_3$N (0.00057 mol) and CH$_2$Cl$_2$ (5 ml) was stirred at room temperature for 30 minutes. Then an aqueous solution of Na$_2$CO$_3$ (1 ml) was added to the reaction mixture and the reaction mixture was filtered through an extrelute filter. Then the filtrate's solvent was evaporated and the residue was purified by high-performance liquid chromatography (standard gradient elution with NH$_4$HCO$_3$). The product fractions were collected and the solvent was evaporated. The residue was dried, yielding 0.044 g (34%; MP: 222.5° C. to 223.4° C.) of compound 108.

Table F-18 lists the compounds that were prepared according to Example B26 described above.

TABLE F-18

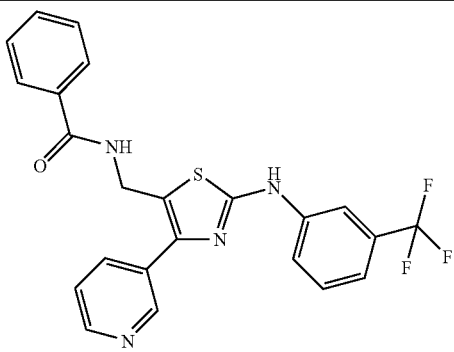

Co. No. 164

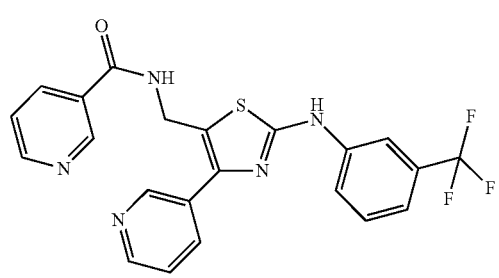

Co. No. 165

TABLE F-18-continued

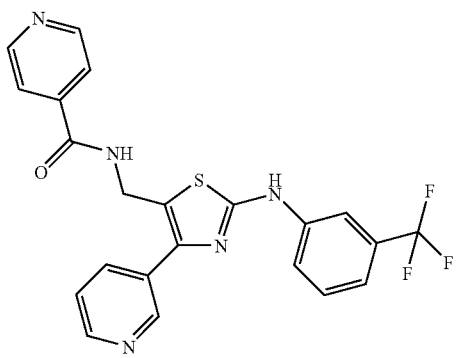

Co. No. 166

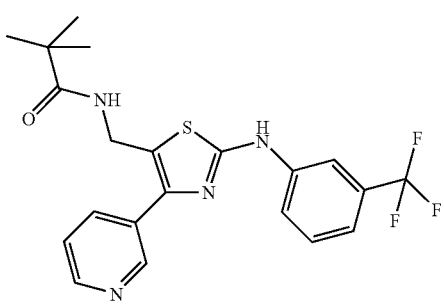

Co. No. 167

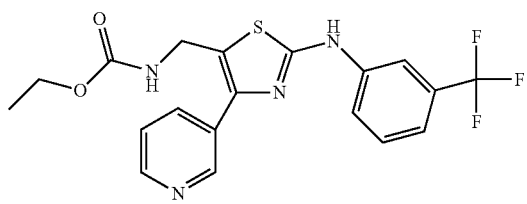

Co. No. 168

Example B27

Preparation of Compound 109

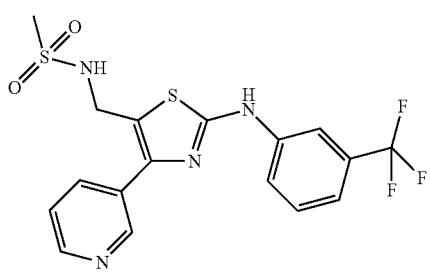 [SMILES: CS(=O)(=O)NCc1sc(Nc2cccc(C(F)(F)F)c2)nc1-c1cccnc1]

A mixture of intermediate 8 (0.000285 mol), methanesulfonyl chloride (0.000285 mol) and Et$_3$N (0.00057 mol) in CH$_2$Cl$_2$ (50 ml) was stirred for 30 minutes at room temperature. Upon reaction completion, the reaction mixture was washed with an aqueous Na$_2$CO$_3$ solution. The organic phase was dried, filtered and the solvent evaporated. The residue was purified by reversed-phase high-performance liquid chromatography (standard gradient elution with NH$_4$HCO$_3$ buffer). The product fractions were collected and the solvent was evaporated, yielding 0.013 g (11%) of compound 109.

Example B28

Preparation of Compound 110

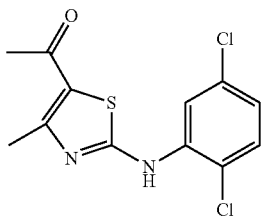 [SMILES: CC(=O)c1sc(Nc2cc(Cl)ccc2Cl)nc1C]

3-Chloro-2,4-pentanedione (0.0238 mol) and (2,5-dichlorophenyl)-thiourea (0.0238 mol) were treated with pyridine (2.1 ml). MeOH (38 ml) was added and the reaction mixture was refluxed. Extra MeOH (30 ml) was added and after 3 hours, the mixture was cooled to room temperature. The product was filtered off and washed 3 times with Et$_2$O, then dried in the vacuum oven, yielding 9.6 g of compound 110.

Example B29

Preparation of Compound 111

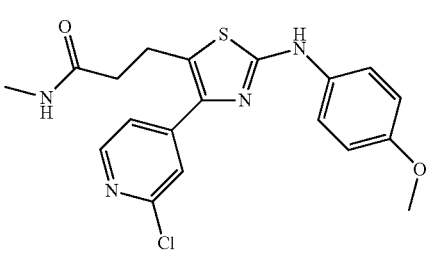 [SMILES: CNC(=O)CCc1sc(Nc2ccc(OC)cc2)nc1-c1ccnc(Cl)c1]

A mixture of intermediate 37 (0.00019 mol) in methanamine (10 ml; 27-32% CH$_3$NH$_2$ alcohol solution) was heated overnight at 85° C. in a sealed tube. The solvent was evaporated. The residue was purified by reversed phase high performance liquid chromatography. The desired fractions were collected and the solvent was evaporated, yielding 0.022 g (28.7%) of compound 111.

Table F-Ia lists the compounds that were prepared as described in Patent Publication No. WO 01/64674, according to Example B1 a) in said Patent Publication No., the Table No. is retrievable in said Patent Publication.

The following abbreviations were used in the table: '.HBr' stands for the hydrobromide acid salt, '.HCl' stands for hydrochloride acid salt, '.C$_2$H$_6$O' stands for ethanolate, 'MP' stands for melting point.

TABLE F-Ia

| Structure | Table No. |
|---|---|
| imidazo[1,2-a]pyridine-thiazole-NH-(6-bromopyridin-3-yl); •HCl; Co. No. 45 | Table No. 10 |
| imidazo[1,2-a]pyridine-thiazole-NH-(2,3-dihydrobenzofuran-5-yl); •HCl; Co. No. 46; MP; 271.0-274.1° C. | Table No. 10 |
| imidazo[1,2-a]pyridine-thiazole-NH-(5-(trifluoromethyl)pyridin-3-yl); •HCl; Co. No. 47; MP; >260° C. | Table No. 10 |
| imidazo[1,2-a]pyridine-thiazole-NH-(6-(trifluoromethyl)pyridin-3-yl); •HCl; Co. No. 48; MP; >260° C. | Table No. 10 |
| imidazo[1,2-a]pyridine-thiazole-NH-(6-(methylthio)pyridin-3-yl); •HCl; Co. No. 49; MP; 238° C. | Table No. 10 |
| imidazo[1,2-a]pyridine-thiazole-NH-(2,4-dimethoxyphenyl); •HCl; Co. No. 50; MP: 158° C. | Table No. 2 |

TABLE F-Ia-continued

| Structure | Table No. |
|---|---|
| imidazo[1,2-a]pyridine-thiazole-NH-(3-methylphenyl); •HCl; Co. No. 51; MP: 218-220° C. | Table No. 2 |
| imidazo[1,2-a]pyridine-thiazole-NH-(3-(methylthio)phenyl); •HCl; Co. No. 52; MP; 220° C. | Table No. 2 |
| imidazo[1,2-a]pyridine-thiazole-NH-(4-chlorophenyl); •HCl•$C_2H_6O$; Co. No. 53 | Table No. 2 |
| imidazo[1,2-a]pyridine-thiazole-NH-(4-chloro-3-(trifluoromethyl)phenyl); •HCl; Co. No. 54 | Table No. 2 |
| imidazo[1,2-a]pyridine-thiazole-NH-(3,4-dimethoxyphenyl); •HCl; Co. No. 55 | Table No. 2 |
| imidazo[1,2-a]pyridine-thiazole-NH-(3-(trifluoromethyl)phenyl); •HCl; Co. No. 56 | Table No. 2 |
| imidazo[1,2-a]pyridine-thiazole-NH-(4-(trifluoromethyl)phenyl); •HCl; Co. No. 57 | Table No. 2 |

TABLE F-Ia-continued (Structure) •HCl•C₂H₆O; Co. No. 58 — Table No. 2

(Structure) •HCl; Co. No. 59; MP: 170-172° C. — Table No. 9

(Structure) •HCl; Co. No. 60 — Table No. 9

(Structure) •HCl; Co. No. 61 — Table No. 9

(Structure) •HCl; Co. No. 62 — Table No. 9

(Structure) •HCl; Co. No. 63; MP: 242° C. — Table No. 9

Table F-Ib lists the compounds that were prepared as described in Patent Publication No. WO 01/64674, according to Example B1 b) in said Patent Publication No., the Table No. is retrievable in said Patent Publication.

The following abbreviations were used in the table: '.HBr' stands for the hydrobromide acid salt, '.HCl' stands for hydrochloride acid salt, 'MP' stands for melting point.

TABLE F-Ib (Structure) •HBr•H₂O; Co. No. 64 — Table No. 11

(Structure) •2HBr; Co. No. 65; MP: >250° C. — Table No. 11

(Structure) •2HBr; Co. No. 66 — Table No. 11

(Structure) •HBr; Co. No. 67 — Table No. 11

(Structure) •HBr; Co. No. 68 — Table No. 11

(Structure) •HCl; Int. 12 — Table No. 12

TABLE F-Ib-continued

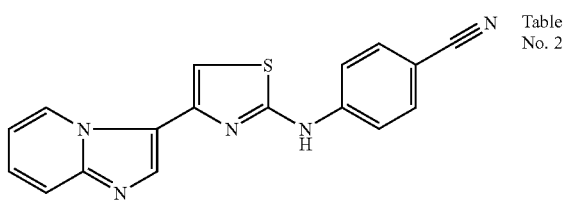

•HBr; Co. No. 69 — Table No. 2

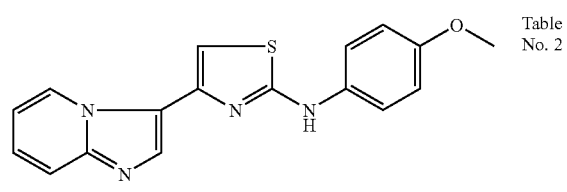

•HBr; Co. No. 70;
MP: 254° C. — Table No. 2

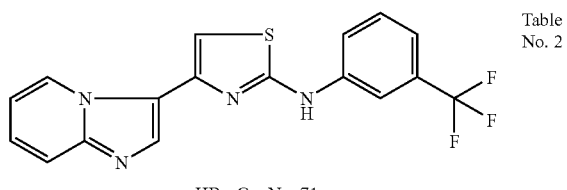

•HBr; Co. No. 71
MP: 260-262° C. — Table No. 2

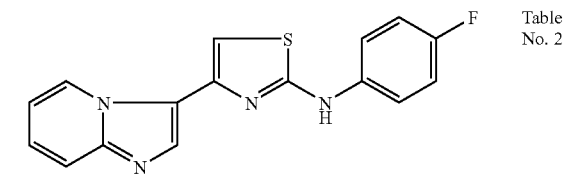

•HCl; Co. No. 72; — Table No. 2

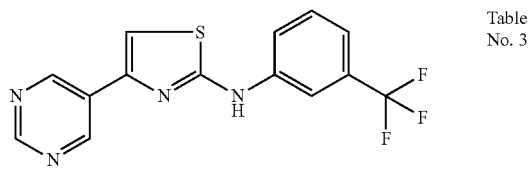

Co. No. 73; MP: 214° C. — Table No. 3

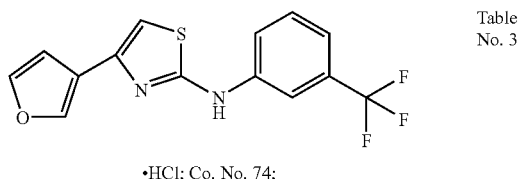

•HCl; Co. No. 74;
MP: 146-148° C. — Table No. 3

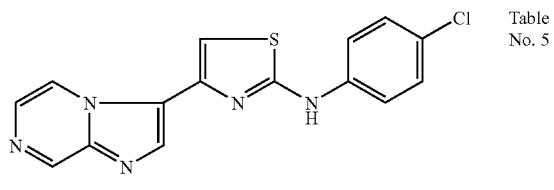

•HBr; Co. No. 75 — Table No. 5

TABLE F-Ib-continued

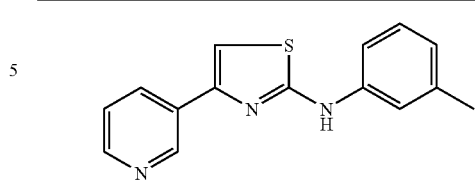

•HBr; Co. No. 76 — Table No. 7

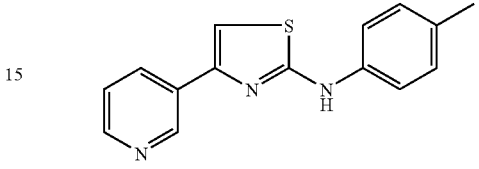

•2HBr; Co. No. 77 — Table No. 7

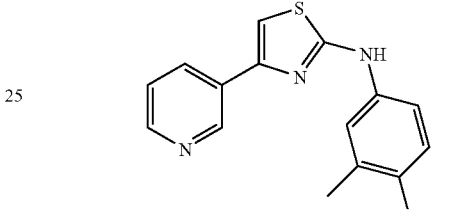

•HBr; Co. No. 78;
MP: 242-244° C. — Table No. 7

Table F-II lists the compounds that were prepared as described in Patent Publication No. WO 03/015773, according to the mentioned Example No. as described in said Patent Publication No. and retrievable in Table No. 1.

The following abbreviations were used in the table: 'MP' stands for melting point.

TABLE F-II

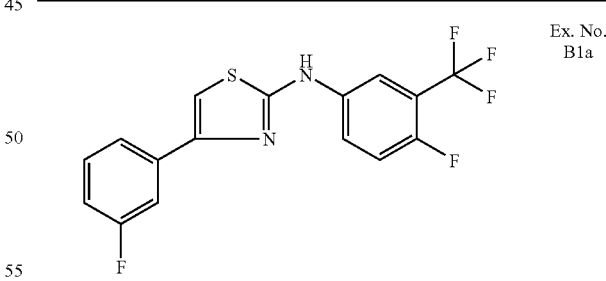

Co. No. 79 — Ex. No. B1a

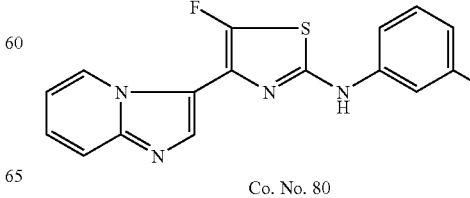

Co. No. 80 — Ex. No. B1a

TABLE F-II-continued

| Structure | Co. No. | Ex. No. |
|---|---|---|
| 5-fluoro-4-(pyridin-3-yl)-N-(4-fluoro-3-(trifluoromethyl)phenyl)thiazol-2-amine | Co. No. 81; MP: 226° C. | B1a |
| 5-fluoro-4-(imidazo[1,2-a]pyridin-3-yl)-N-(m-tolyl)thiazol-2-amine | Co. No. 82 | B1a |
| 5-fluoro-N-(4-fluoro-3-methylphenyl)-4-(pyridin-3-yl)thiazol-2-amine | Co. No. 83; MP: 176-178° C. | B1b |
| 5-bromo-4-(pyridin-3-yl)-N-(4-fluoro-3-(trifluoromethyl)phenyl)thiazol-2-amine | Co. No. 84 | B2b |
| 4-(imidazo[1,2-a]pyridin-3-yl)-5-methyl-N-(4-(trifluoromethyl)phenyl)thiazol-2-amine | Co. No. 85 | B2b |
| 5-methyl-4-(pyridin-3-yl)-N-(4-(trifluoromethyl)phenyl)thiazol-2-amine | Co. No. 86 | B2b |
| 4-methyl-5-(pyridin-3-yl)-N-(4-(trifluoromethyl)phenyl)thiazol-2-amine | Co. No. 87 | B2b |
| 6-chloro-N-(4-methyl-5-(pyridin-3-yl)thiazol-2-yl)pyridin-3-amine | Co. No. 88 | B1a |
| (2-((4-fluoro-3-(trifluoromethyl)phenyl)amino)-4-(pyridin-4-yl)thiazol-5-yl)methanol | Co. No. 89; MP: 240-247° C. | B6 |
| 5-(morpholinomethyl)-4-(pyridin-3-yl)-N-(4-fluoro-3-(trifluoromethyl)phenyl)thiazol-2-amine | Co. No. 90 | B9 |
| (2-((4-fluoro-3-(trifluoromethyl)phenyl)amino)-4-(pyridin-3-yl)thiazol-5-yl)methanol | Co. No. 91 | B9 |
| 5-fluoro-4-(pyridin-3-yl)-N-(3-(trifluoromethyl)phenyl)thiazol-2-amine | Co. No. 92 | B1a |

Table F-III lists the known compounds that where found to be positive modulators of the α7 nicotinic acetylcholine receptor, and accordingly useful in the treatment or prophylaxis of psychotic disorders, intellectual impairment disorders or diseases or conditions in which modulation of the α7 nicotinic receptor is beneficial, in particular in the treatment of cognitive deficits seen in diseases such as Alzheimer's disease and schizophrenia, more in particular in the treatment of ADHD, anxiety, schizophrenia, mania, manic depression or other neurological or psychiatric disorders in which there is loss of cholinergic function, including loss of cholinergic synapses, including jetlag, nicotine addiction and pain.

TABLE F-III

| Registry Number | Co. No. | CA Index Name |
|---|---|---|
| 315679-10-8 | 169 | 5-Thiazolecarboxamide, 2-[(4-fluorophenyl)amino]-4-phenyl-N-3-pyridinyl- |
| 356569-19-2 | 170 | 5-Thiazolecarboxamide, 2-[(2,4-dimethylphenyl)amino]-4-phenyl-N-3-pyridinyl- |
| 307513-68-4 | 171 | 5-Thiazolecarboxamide, 4-phenyl-2-(phenylamino)-N-3-pyridinyl- |
| 356569-17-0 | 172 | 5-Thiazolecarboxamide, 2-[(2-methylphenyl)amino]-4-phenyl-N-3-pyridinyl- |
| 406469-54-3 | 173 | 5-Thiazolepropanoic acid, 4-(4-methoxyphenyl)-2-[(4-methoxyphenyl)amino]-, methyl ester |
| 311791-26-1 | 174 | 5-Thiazolecarboxylic acid, 2-[(2,5-dichlorophenyl)amino]-4-phenyl-, ethyl ester |

It is accordingly an object of the invention to provide the use of the compounds enlisted in any one of tables F-Ia, F-Ib, F-II or F-III in the manufacture of a medicament for the treatment or prophylaxis of psychotic disorders, intellectual impairment disorders or diseases or conditions in which modulation of the α7 nicotinic receptor is beneficial, in particular in the treatment of cognitive deficits seen in diseases such as Alzheimer's disease and schizophrenia, more in particular in the treatment of ADHD, anxiety, schizophrenia, mania, manic depression or other neurological or psychiatric disorders in which there is loss of cholinergic function, including loss of cholinergic synapses, including jetlag, nicotine addiction and pain.

Compound Identification

LCMS-Methods:

General Procedure A

The HPLC gradient was supplied by a Waters Alliance HT 2790 system with a column heater set at 40° C. Flow from the column was split to a Waters 996 photodiode array (PDA) detector and a Waters-Micromass ZQ mass spectrometer with an electrospray ionization source operated in positive and negative ionization mode. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The HPLC gradient was supplied by an Agilent 1100 module consisting of a pump and DAD detector (wavelength used 220 nm) and column heater. Flow from the column was split to the Agilent MSD Series G1946C and G1956A. MS detector was configured with API-ES. Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

General Procedure C

The HPLC gradient was supplied by an Alliance HT 2795 (Waters) system consisting of a quaternary pump with degasser, an autosampler, a column oven (set at 40° C.) and DAD detector. Flow from the column was split to the MS detector. MS detectors were configured with an electrospray ionization source. Mass spectra were acquired by scanning from 100 to 1500 in 1 second using a dwell time of 0.1 second. The capillary needle voltage was 3.5 kV and the source temperature was maintained at 100° C. Nitrogen was used as the nebulizer gas. Data acquisition was performed with a Waters-Micromass MassLynx-Openlynx data system.

Method 1

In addition to general procedure A: Reversed phase HPLC was carried out on an Xterra MS C18 column (3.5 mm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 μl was used. Cone voltage was 10 V for positive ionization mode and 20 V for negative ionization mode.

Method 2

In addition to general procedure A: Reversed phase HPLC was carried out on an Xterra MS C18 column (3.5 mm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

Method 3

In addition to general procedure A: Reversed phase HPLC was carried out on an Xterra MS C18 column (3.5 mm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 μl was used.

Cone voltage was 10 V for positive ionization mode and 20 V for negative ionization mode.

Method 4

In addition to general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 μl was used. Cone voltage was 10 V for positive ionization mode and 20 V for negative ionization mode.

Method 5

In addition to general procedure A: Column heater was set at 60° C. Reversed phase HPLC was carried out on an Xterra MS C18 column (3.5 mm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

Method 6

In addition to general procedure A: Reversed phase HPLC was carried out on an Xterra MS C18 column (3.5 mm, 4.6×100 mm) with a flow rate of 1.2 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 2% A, 49% B and 49% C in 10 minutes, to 1% A and 99% B in 1 minute and hold these conditions for 3 minutes and reequilibrate with 100% A for 2.5 minutes. An injection volume of 10 μl was used. Cone voltage was 10 V for positive ionization mode and 20 V for negative ionization mode. Column temperature was 45° C.

Method 7

In addition to general procedure B: Reversed phase HPLC was carried out on a YMC ODS-AQ S-5 μm, 12 nm column (2.0×50 mm) with a flow rate of 0.8 ml/min. Two mobile phases (mobile phase A: water with 0.1% TFA; mobile phase B: acetonitrile with 0.05% TFA) were used to run a gradient condition from 95% A and 5% B to 100% B in 3.5 minutes. Typical injection volumes of 2 μl were used. Column temperature was 50° C.

Method 8

In addition to general procedure B: Reversed phase HPLC was carried out on a YMC ODS-AQ S-5 μm, 12 nm column (2.0×50 mm) with a flow rate of 0.8 ml/min. Two mobile phases (mobile phase A: water with 0.1% TFA; mobile phase B: acetonitrile with 0.05% TFA) were used to run a gradient condition from 90% A and 10% B to 100% B in 3.4 minutes and hold for 0.1 minutes. Typical injection volumes of 2 μl were used. Column temperature was 50° C.

Method 9

In addition to general procedure B: Reversed phase HPLC was carried out on a YMC ODS-AQ S-5 μm, 12 nm column (2.0×50 mm) with a flow rate of 0.8 ml/min. Two mobile phases (mobile phase A: water with 0.1% TFA; mobile phase B: acetonitrile with 0.05% TFA) were used to run a gradient condition from 80% A and 20% B to 100% B in 3.3 minutes and hold for 0.2 minutes. Typical injection volumes of 2 μl were used. Column temperature was 50° C.

Method 10

In addition to general procedure B: Reversed phase HPLC was carried out on a YMC ODS-AQ S-5 μm, 12 nm column (2.0×50 mm) with a flow rate of 0.8 ml/min. Two mobile phases (mobile phase A: water with 0.1% TFA; mobile phase B: acetonitrile with 0.05% TFA) were used to run a gradient condition from 70% A and 30% B to 100% B in 3.2 minutes and hold for 0.3 minutes. Typical injection volumes of 2 μl were used. Column temperature was 50° C.

Method 11

In addition to general procedure B: Reversed phase HPLC was carried out on a YMC ODS-AQ S-5 μm, 12 nm column (2.0×50 mm) with a flow rate of 0.8 ml/min. Two mobile phases (mobile phase A: water with 0.1% TFA; mobile phase B: acetonitrile with 0.05% TFA) were used to run a gradient condition from 60% A and 40% B to 100% B in 3 minutes and hold for 0.5 minutes. Typical injection volumes of 2 μl were used. Column temperature was 50° C.

Method 12

In addition to general procedure B: Reversed phase HPLC was carried out on a YMC ODS-AQ S-5 μm, 12 nm column (2.0×50 mm) with a flow rate of 0.8 ml/min. Two mobile phases (mobile phase C: 10 mmol/L $NH_4HCO_3$; mobile phase D: acetonitrile) were used to run a gradient condition from 90% C and 10% D to 100% D in 3.4 minutes and hold for 0.1 minutes. Typical injection volumes of 2 μl were used. Column temperature was 50° C.

Method 13

In addition to general procedure B: Reversed phase HPLC was carried out on a YMC ODS-AQ S-5 μm, 12 nm column (2.0×50 mm) with a flow rate of 0.8 ml/min. Two mobile phases (mobile phase A: water with 0.1% TFA; mobile phase B: acetonitrile with 0.05% TFA) were used to run a gradient condition from 90% A and 10% B to 100% B in 3.4 minutes and hold for 0.1 minutes. Typical injection volumes of 2 μl were used. Column temperature was 50° C.

Method 14

In addition to general procedure B: Reversed phase HPLC was carried out on a YMC ODS-AQ S-5 μm, 12 nm column (2.0×50 mm) with a flow rate of 0.8 ml/min. Two mobile phases (mobile phase A: water with 0.1% TFA; mobile phase B: acetonitrile with 0.05% TFA) were used to run a gradient condition from 70% A and 30% B to 100% B in 3.2 minutes and hold for 0.3 minutes. Typical injection volumes of 2 μl were used. Column temperature was 50° C.

Method 15

In addition to general procedure A: Reversed phase HPLC was carried out on an Xterra MS C18 column (3.5 mm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 30% A, 35% B; 35% C in 3 minutes to 50% B and 50% C in 3.5 minutes, to 100% B in 0.5 minutes. An injection volume of 10 μl was used. Cone voltage was 10 V for positive ionization mode.

Method 16

In addition to general procedure C: Reversed phase HPLC was carried out on an Xterra MS C18 column (3.5 mm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 7.5 minutes, to 100% B in 1 minute, 100% B for 2 minutes and reequilibrate with 100% A for 2 minutes. An injection volume of 10 μl was used. Cone voltage was 30 V for positive ionization mode and 30 V for negative ionization mode.

Method 17

In addition to general procedure B: Reversed phase HPLC was carried out on a YMC ODS-AQ S-5 μm, 12 nm column (2.0×50 mm) with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 μl were used. Oven temperature was 50° C.

TABLE

Analytical data

| Comp. Nr. | $R_t$ | $(MH)^+$ | Procedure | Physico-chemical data |
|---|---|---|---|---|
| 1 | 6.07 | 378 | 1 | 186-187° C. |
| 18 | 6.46 | 446 | 1 | 209-211° C. |
| 64 | 5.37 | 333 | 1 | HBr-salt |
| 60 | 6.03 | 313 | 1 | HCl-salt |
| 80 | 4.36 | 379 | 1 | |
| 88 | 5.45 | 303 | 1 | |
| 91 | 5.76 | 370 | 1 | |
| 17 | 6.04 | 353 | 1 | HCl-salt |
| 61 | 5.51 | 341 | 1 | HCl-salt |
| 62 | 6.31 | 367 | 1 | HCl-salt |

TABLE-continued

Analytical data

| | | | | |
|---|---|---|---|---|
| 29 | 7.12 | 375 | 1 | 154° C. HCl-salt |
| 26 | 6.34 | 347 | 1 | |
| 47 | 5.87 | 362 | 1 | >260° C. HCl-salt |
| int. 12 | 6.94 | 339 | 1 | HCl-salt |
| 55 | 5.32 | 353 | 1 | HCl-salt |
| 44 | 6.38 | 385 | 1 | HCl-salt |
| 10 | 5.67 | 355 | 1 | |
| 5 | 6.59 | 358 | 1 | |
| 52 | 6.21 | 339 | 1 | 220° C. HCl-salt |
| 58 | 6.46 | 371 | 1 | HCl-salt |
| 51 | 6.16 | 307 | 1 | 218-220° C. HCl-salt |
| 71 | 6.47 | 361 | 1 | 260-262° C. HBr-salt |
| 56 | 6.46 | 361 | 1 | HCl-salt |
| 74 | 6.54 | 311 | 1 | 146-148° C. HCl-salt |
| 11 | 7.08 | 375 | 1 | 194° C. HBr-salt |
| 20 | 7.02 | 357 | 1 | HBr-salt |
| 12 | 7.18 | 355 | 1 | HBr-salt |
| 25 | 6.22 | 322 | 1 | HBr-salt |
| 16 | 6.53 | 340 | 1 | HBr-salt |
| 63 | 5.71 | 368 | 1 | 242° C. HCl-salt |
| 93 | 6.87 | 361 | 2 | 114.1-115.0° C. |
| 115 | 1.07 | 378 | 4 | 189.5-192.7° C. |
| 162 | 1 | 433 | 4 | 146.7-156.9° C. |
| 106 | 0.92 | 437 | 4 | 218.0-224.2° C. |
| 161 | 6.13 | 421 | 2 | 256.1-263.7° C. |
| 85 | 6.59 | 375 | 1 | |
| 27 | 5.94 | 323 | 1 | >260° C. HBr-salt |
| 53 | 6.34 | 327 | 1 | HCl-salt |
| 2 | 6.54 | 320 | 1 | 175° C. |
| 15 | 5.83 | 347 | 1 | |
| 30 | 6.3 | 275 | 1 | 162° C. HCl-salt |
| 19 | 6.18 | 332 | 1 | HBr-salt |
| 40 | 7.21 | 381 | 1 | |
| 42 | 6.84 | 317 | 1 | |
| 14 | 6.3 | 340 | 1 | HBr-salt |
| 66 | 4.74 | 269 | 1 | HBr-salt |
| 90 | 6.31 | 439 | 1 | |
| 13 | 6.96 | 339 | 1 | |
| 76 | 5.86 | 268 | 1 | HBr-salt |
| 87 | 6.36 | 336 | 1 | |
| 86 | 6.37 | 336 | 1 | HBr-salt |
| 24 | 6.32 | 303 | 1 | HBr-salt |
| int. 1 | 6.89 | 321 | 1 | |
| 70 | 5.68 | 323 | 1 | 254° C. HBr-salt |
| 79 | 7 | 356 | 1 | HBr-salt |
| 101 | 6.33 | 336 | 2 | HBr-salt |
| 6 | 7.32 | 417 | 1 | HCl-salt |
| int. 5 | 3.7 | 185 | 1 | |
| int. 6 | 7.18 | 393 | 1 | 150° C. |
| 72 | 5.89 | 311 | 1 | HCl-salt |
| int. 7 | 6.31 | 347 | 1 | |
| int. 2 | 6.36 | 351 | 1 | |
| 3 | 6.62 | 351 | 1 | |
| 23 | 6.26 | 428 | 1 | 167-168° C. |
| 150 | 3.33 | 331 | 9 | |
| int. 25 | 2.27 | 378 | 7 | 206.8-208.7° C. |
| 112 | 3.41 | 422 | 8 | 204.1-205.5° C. |
| 132 | 2.48 | 494.1 | 10 | 170.2-177.0° C. |
| 123 | 2.08 | 344.1 | 7 | 104.5-106.6° C. |
| 134 | 2.91 | 454 | 8 | 177.9-181.6° C. |
| 126 | 2.35 | 437 | 8 | 160.1-169.5° C. |
| 99 | 1.92 | 431.1 | 8 | 199.3-201.7° C. |
| 100 | 2.13 | 447.1 | 13 | 183.4-187.2° C. |
| 114 | 2.36 | 387 | 7 | decomposed at 181.2° C. |
| 130 | 2.89 | 440 | 8 | |
| 116 | 3.37 | 317.1 | 12 | |
| 143 | 3.19 | 331.1 | 9 | |
| 155 | 3.49 | 359.1 | 9 | |
| 96 | 2.68 | 462 | 13 | |
| 119 | 3.53 | 343 | 12 | |
| 160 | 3.21 | 534.2 | 11 | |
| 145 | 3.26 | 357.1 | 10 | |
| 103 | 2.84 | 347 | 9 | |
| 97 | 2.9 | 476.1 | 13 | |
| 140 | 3.08 | 347 | 8 | |
| 135 | 2.28 | 459.1 | 8 | |
| 95 | 3.06 | 401.1 | 12 | |
| 105 | 2.22 | 405.1 | 7 | |
| 117 | 3.31 | 317.1 | 12 | |
| int. 19 | 3.22 | 435.1 | 12 | |
| 144 | 2.9 | 293.1 | 8 | |
| 104 | 3.15 | 496.2 | 10 | |
| 148 | 3.4 | 345.1 | 9 | |
| 151 | 3.09 | 307.1 | 8 | |
| 159 | 3.17 | 361.1 | 8 | |
| int. 20 | 3.05 | 444.1 | 8 | |
| 118 | 2.68 | 305.1 | 12 | |
| 154 | 3.13 | 347.1 | 8 | |
| 147 | 3.34 | 385 | 14 | |
| 107 | 3.14 | 440 | 8 | |
| 152 | 3.47 | 357 | 10 | |
| 149 | 3.6 | 345 | 9 | |
| 156 | 3.52 | 359 | 10 | |
| 153 | 3.23 | 367 | 9 | |
| 158 | 2.78 | 323.1 | 8 | |
| 146 | 3.3 | 319.1 | 8 | |
| 102 | 2.88 | 321.1 | 9 | |
| 157 | 3.33 | 361 | 8 | |
| 133 | 2.5 | 516 | 9 | |
| 174 | 10.69 | 393 | 6 | |
| 129 | 1.04 | 366 | 4 | |
| 128 | 1.07 | 366 | 4 | |
| 125 | 0.92 | 377 | 4 | 196.2-198.9° C. |
| 65 | 5.62 | 323 | 1 | >250° C. HBr-salt |
| 73 | 5.93 | 323 | 1 | 214° C. |
| 59 | 6.34 | 367 | 1 | 170-172° C. HCl-salt |
| 49 | 5.61 | 340 | 1 | 238° C. HCl-salt |
| 45 | 5.65 | 372 | 1 | HCl-salt |
| 54 | 6.8 | 395 | 1 | HCl-salt |
| 69 | 5.54 | 318 | 1 | HBr-salt |
| 78 | 5.97 | 286 | 1 | 242-244° C. HBr-salt |
| 48 | 5.82 | 362 | 1 | >260° C. HCl-salt |
| 68 | 6.45 | 336 | 1 | HBr-salt |
| 50 | 5.85 | 353 | 1 | 158° C. HCl-salt |
| 34 | 6.65 | 343 | 1 | |
| 75 | 5.84 | 328 | 1 | HBr-salt |
| 77 | 5.87 | 268 | 1 | HBr-salt |
| 22 | 5.89 | 355 | 1 | HBr-salt |
| 67 | 6.67 | 336 | 1 | HBr-salt |
| 83 | 6.4 | 304 | 1 | 176-178° C. |
| 9 | 6.5 | 379 | 1 | 248° C. HCl-salt |
| 84 | 6.74 | 418 | 1 | |
| 7 | 7.26 | 357 | 1 | HCl-salt |
| 127 | 4.72 | 313 | 5 | 179.9-182.4° C. |
| 89 | 5.75 | 370 | 1 | 240-247° C. |
| 46 | | | | 271.0-274.1° C. HCl-salt |
| 81 | | | | 226° C. |
| int. 3 | | | | 121-122° C. |
| 28 | 7.45 | 389 | 2 | |
| 8 | 8.11 | 381 | 15 | |
| 31 | 6.09 | 419 | 1 | |
| 35 | 6.72 | 353 | 15 | |
| 36 | 8.09 | 381 | 15 | |
| 37 | 6.69 | 353 | 15 | |
| 38 | 7.56 | 345 | 15 | |
| 39 | 8.24 | 381 | 15 | |

TABLE-continued

Analytical data

| | | | | |
|---|---|---|---|---|
| 41 | 1.17 | 355 | 4 | |
| 57 | 6.45 | 361 | 2 | |
| 82 | | | | 228.37° C. |
| 43 | 7.61 | 347 | 15 | |
| 33 | 7.51 | 345 | 15 | |
| 32 | 0.87 | 411 | 4 | |
| 120 | 6.34 | 286 | 2 | |
| 94 | 6.73 | 302 | 16 | |
| 110 | 6.5 | 301 | 16 | |
| 168 | 6.15 | 423 | 16 | |
| 141 | | | | 207.26° C. |
| 138 | 6.2 | 282 | 16 | |
| 142 | 6.22 | 340 | 16 | |
| 139 | 5.63 | 298 | 16 | |
| 137 | 6.38 | 346 | 16 | |
| 169 | 6.02 | 391 | 16 | |
| 170 | 6.2 | 401 | 16 | |
| 171 | 5.9 | 373 | 16 | |
| 172 | 5.88 | 387 | 16 | |
| 173 | 6.42 | 399 | 16 | |
| 111 | 5.14 | 403 | 17 | 168.8-171.0° C. |

| Comp. Nr. | $R_t$ | $(MH)^-$ | Procedure | Melting point (° C.) |
|---|---|---|---|---|
| 4 | 0.96 | 391 | 4 | |
| 124 | 0.84 | 363 | 4 | 155.5-159.7° C. |
| 109 | 0.9 | 427 | 4 | 213.6-219.8° C. |
| 167 | 1.04 | 433 | 4 | 248.7-249.4° C. |
| 164 | 1.03 | 453 | 4 | 215.5-218.9° C. |
| 166 | 0.98 | 454 | 4 | 245.9-247.3° C. |
| int. 23 | 1.11 | 349 | 4 | 172.8-175.0° C. |
| 131 | 0.99 | 390 | 4 | |
| 122 | 0.82 | 312 | 4 | 126.2-126.8° C. |
| 113 | 0.89 | 377 | 4 | 249.6-257.1° C. |
| 165 | 0.98 | 454 | 4 | |
| 108 | 1.02 | 458 | 4 | 222.5-223.4° C. |
| 98 | 1.22 | 363 | 4 | 105.1-105.5° C. |
| 136 | 1.22 | 364 | 4 | 205.3-205.8° C. |
| int. 30 | 1.03 | 406 | 4 | 156.8-163.5° C. |
| 163 | 0.92 | 391 | 4 | 237.2-244.0° C. (Buchi visual) |

C. Pharmacological Example

Example C.1

Ca$^{2+}$ Flux Imaging

Stable expression in mammalian cells in general and rat GH4C1 cells in particular, of cDNA clones encoding the human α7 wild-type sequence (hα7-wt nAChR) and in which the coding region is placed downstream of a promoter results in the appearance of functional α7 nAChRs on the surface of the mammalian cells. This technique has provided a powerful means of assessing the function of α7 wild-type protein. Given the fact that the cation permeability of the α7 nicotinic receptor preferentially favours calcium, fluorescent imaging of Ca$^{2+}$ flux through the hα7-wt nAChR stably expressed in the GH4C1 cell line was used as a first means of assaying modulator activity of the compounds of the present invention.

Materials a) Assay Buffer

Hanks buffered saline solution (HBSS, Invitrogen, Belgium), supplemented with 10 mM HEPES (Invitrogen, Belgium), CaCl$_2$ to a final concentration of 5 mM, 0.1% Bovine serum albumin (Sigma-Aldrich NV, Belgium), 2.5 mM probenecid (Sigma-Aldrich NV, Belgium).

b) Calcium-Sensitive Dye—Fluo-4AM

Fluo-4AM (Molecular Probes, USA) was dissolved in DMSO containing 10% Pluronic acid (Molecular Probes, USA) to give a stock solution which was aliquoted and could be stored at −20° C. until later use. On the day of the experiment Fluo-4AM stock was defrosted and diluted in DMEM/F12 (Invitrogen, Belgium) containing 2.5 mM probenicid and 0.1% BSA to give a final concentration of 2 µM.

c) 96-well Plates

BD Biocoat poly-D-lysine 96-well black/clear bottom plates (BD Biosciences, Belgium)

d) Calcium Flux Measurement

A Fluorimetric Imaging Plate Reader (FLIPR, Molecular Devices Corporation, Sunnyvale, USA) was used to measure intracellular free-calcium flux signals Method Monolayers of hα7-wt nAChR-expressing cells were grown in multi-well plates, in particular black-sided, transparent bottomed 96 well plates coated with poly-D-lysine for 24 hours prior to loading with a fluorescent calcium indicator, in a particular embodiment loading with fluo-3 or fluo-4AM for up to 90 minutes, in an even more particular embodiment loading with fluo-4AM for up to 90 minutes, and in a preferred embodiment loading with fluo-4AM for 60 minutes.

PAM activity was detected in real time by applying the compounds to be tested to the loaded cells along with a α7 nicotinic receptor agonist during constant monitoring of cellular fluorescence in a FLIPR. Compounds giving peak fluorescent responses greater than the response due to agonist alone, were considered to be α7 nAChR PAM's. In a particular embodiment, the α7 nicotinic receptor agonist was choline, a more particular embodiment choline applied at a sub-maximal concentration of 100 µM. In a further setting of the present invention the compounds to be tested were applied prior to the α7 nicotinic receptor agonist, in a particular embodiment up to 20 minutes prior to the agonist, a more particular embodiment up to 10 minutes prior to the agonist, and an even more particular embodiment 10 minutes prior to the agonist.

A control response to choline was calculated on each plate from the difference in peak fluorescence in wells receiving either choline or assay buffer alone. Compounds of the present invention were tested at a concentration range from 0.1 µM to 30 µM. Compounds were considered to have an interesting activity when their efficacy was at least 1.1 when tested at a concentration of 10 µM (the efficacy of 100 µM choline was defined as 1 in the absence of a PAM). Analogously, more preferred compounds have an efficacy of at least 1.5 relative to choline, even more preferred compounds at least 2.0, still more preferred compounds at least 3.0 and most preferred compounds at least 4.5. In a most preferred embodiment of the invention, compounds also have a potentiating effect on the response to choline when measured by whole-cell patch clamp electrophysiology in GH4C1 cells stably over-expressing the human wild-type α7 receptor.

Table 1 lists the results for the compounds of the present invention in the Ca$^{2+}$ flux imaging assay. The activity ranges are defined as follows; A denotes an activity range from 1.1 till 1.5, B denotes an activity range from 1.5 till 2.0, C denotes an activity range from 2.0 till 3.0, D denotes an activity range from 3.0 till 4.5 and E denotes an efficacy from at least 4.5.

TABLE 1

| Compound No. | Activity Range |
|---|---|
| 1 | C |
| 2 | D |
| 3 | D |
| 4 | D |
| 5 | D |
| 6 | C |
| 7 | C |
| 8 | C |
| 9 | C |
| 10 | A |
| 11 | D |
| 20 | C |
| 12 | C |
| 21 | D |
| 13 | C |
| 22 | B |
| int. 3 | D |
| 23 | D |
| 14 | C |
| 24 | D |
| 15 | D |
| 25 | C |
| int. 1 | C |
| 26 | C |
| 19 | C |
| 16 | C |
| 27 | C |
| 17 | A |
| 28 | A |
| 18 | B |
| int. 6 | E |
| 31 | B |
| 32 | C |
| 33 | D |
| 38 | D |
| 34 | C |
| 39 | C |
| 35 | C |
| 40 | C |
| 36 | C |
| 41 | A |
| 37 | C |
| 42 | B |
| 43 | B |
| 44 | C |
| 29 | A |
| 30 | C |
| 79 | B |
| 80 | C |
| 81 | C |
| 82 | B |
| 83 | C |
| 84 | C |
| 85 | C |
| 86 | D |
| 87 | C |
| 88 | C |
| 89 | E |
| 90 | C |
| 91 | C |
| 45 | D |
| 46 | C |
| 47 | C |
| 49 | E |
| 50 | D |
| 51 | C |
| 52 | C |
| 53 | D |
| 54 | A |
| 55 | B |
| 56 | C |
| 57 | C |
| 58 | C |
| 59 | B |
| 60 | B |
| 61 | C |
| 62 | D |

TABLE 1-continued

| Compound No. | Activity Range |
|---|---|
| 62 | B |
| 64 | D |
| 65 | C |
| 66 | D |
| 67 | C |
| 68 | E |
| int. 12 | C |
| 69 | D |
| 70 | D |
| 71 | B |
| 72 | C |
| 73 | C |
| 74 | B |
| 75 | C |
| 76 | C |
| 77 | C |
| 78 | B |
| 174 | E |
| 173 | D |
| 150 | E |
| 172 | E |
| 171 | E |
| 170 | D |
| 133 | E |
| 140 | E |
| 161 | E |
| 106 | E |
| 97 | E |
| 103 | E |
| 157 | E |
| 102 | E |
| 146 | E |
| 158 | E |
| 153 | E |
| 163 | E |
| 162 | E |
| 156 | E |
| 149 | E |
| 152 | E |
| 145 | E |
| 107 | E |
| 160 | E |
| 147 | E |
| 119 | E |
| 96 | E |
| 154 | E |
| 118 | E |
| int. 20 | E |
| 159 | E |
| 151 | E |
| 110 | E |
| 155 | E |
| 148 | E |
| 104 | E |
| 143 | E |
| 144 | E |
| int. 19 | E |
| 117 | E |
| 116 | E |
| 105 | E |
| int. 30 | E |
| 136 | E |
| 95 | E |
| 135 | E |
| 129 | E |
| 128 | E |
| 125 | E |
| 98 | E |
| 130 | E |
| 114 | E |
| 108 | E |
| 165 | E |
| 100 | D |
| 99 | D |
| 126 | E |
| 134 | E |

TABLE 1-continued

| Compound No. | Activity Range |
|---|---|
| 123 | D |
| 132 | E |
| 113 | E |
| 122 | E |
| 115 | E |
| 131 | E |
| 112 | E |
| int. 23 | D |
| int. 25 | C |
| 166 | E |
| 164 | E |
| 167 | D |
| 109 | E |
| 124 | E |
| 127 | E |
| 93 | E |
| 101 | D |
| 139 | D |
| 142 | E |
| 138 | E |
| 141 | C |
| 137 | D |
| 94 | D |
| 111 | E |
| 120 | C |
| 168 | E |

Example C.2

Patch-Clamp Current Recording

Patch-clamp recording from mammalian cells has provided a powerful means of assessing the function of membrane-bound proteins thought to be subunits of ligand-gated ion channels. Activation of such proteins by endogenous or exogenous ligands cause opening of a pore associated with the receptor through which ions flow down their electrochemical gradient. In the case of the hα7-wt nAChR-expressing GH4C1 recombinant cell line the preferential permeability to calcium of this receptor means that calcium flows into the cell upon activation by ACh, choline and other nicotinic ligands giving rise to a calcium current. Since this receptor rapidly desensitizes in the presence of agonist it is important an application system is used which is capable of very rapid switching of solutions (<100 ms) to prevent partial or full desensitisation of receptor responses coincident with the time of agonist application. Consequently, a second convenient technique to assess the enhancement of nicotinic efficacy is patch-clamp recording from hα7-wt nAChR-expressing GH4C1 cells coupled with a rapid-application system.

Materials a) Assay buffers

The external recording solution consisted of 152 mM NaCl, 5 mM KCl, 1 mM $MgCl_2$, 1 mM Calcium, 10 mM HEPES; pH 7.3. The internal recording solution consisted of 140 mM CsCl, 10 mM HEPES, 10 mM EGTA, 1 mM $MgCl_2$, pH 7.3.

b) Patch-clamp recording was carried out using a Patch-clamp amplifier (Multiclamp 700A, Axon Instruments, CA, USA). hα7-wt nAChR-expressing GH4C1 cells were patch-clamp in the whole cell configuration (Hamill et al, 1981) with a borosilicate glass electrode of 1.5-3 MΩ tip resistance when filled with the internal recording solution. Recordings were made on cells with membrane resistance >500 MΩ and more preferably 1 GΩ and series resistance <15 MΩ with at least 60% series resistance compensation. Membrane potential was clamped at −70 mV.

c) Agonists

ACh, choline, were purchased from Sigma-Aldrich NV, Belgium.

d) Compound application

A 16-channel Dynflow DF-16 microfluidics system (Cellectricon, Sweden) for rapid switching of solutions (switching resolution time <100 ms) was used to apply control, agonist and PAM compounds to hα7-wt nAChR-expressing GH4C1 cells.

Method hα7-wt nAChR-expressing GH4C1 cells were plated in external recording solution in the Dynaflow perfusion chamber and were allowed to settle for up to 20 minutes. Individual cells were whole-cell patched and gently lifted off the chamber bottom with the patch pipette into a continuously-flowing perfusion stream (12 μl/min) of external recording solution. PAM activity was detected in real time by pre-applying the compounds to be tested to the loaded cells followed by an α7 nicotinic receptor agonist during constant monitoring of cellular membrane current. Compounds giving current responses greater than the response due to agonist alone, were considered to be α7 nAChR PAM's. In a particular embodiment, the α7 nicotinic receptor agonist was activated by a non-selective nicotinic agonist, in a more particular embodiment the agonist was choline, and an even more particular embodiment choline applied at a sub-maximal concentration of 1 mM. In a further setting of the present invention the compounds to be tested were applied prior to the α7 nicotinic receptor agonist, in a more particular embodiment up to 30 seconds prior to the agonist and even more particularly 5 seconds prior to the agonist. A control response was calculated from the area under the curve of the current elicited in each cell to an application of submaximal choline for 250 ms. Area under the curve is the integration of net current over time and is a common representation of the total ion flux through the channel. Increases in agonist efficacy elicited by a positive modulator were calculated as percent potentiation of "area under curve" (AUC) of the agonist response. Potentiation greater than control AUC caused by compounds of the invention indicates that they are expected to have useful therapeutic activity. EC50 values, maximal effect, and Hill slopes were estimated by fitting the data to the logistic equation using GraphPad Prism (GraphPad Software, Inc., San Diego, Calif.).

The invention claimed is:

1. A compounds of formula

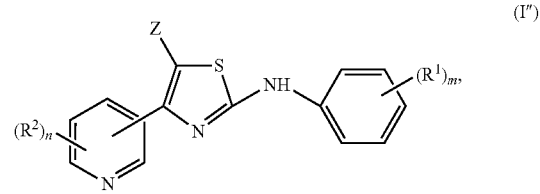

(I″)

a pharmaceutically acceptable addition salt, or a stereochemically isomeric form thereof, wherein n is 0, 1, 2, 3 or 4;

m is 0, 1, 2, 3 or 4;

$R^1$ each independently represents halo; hydroxy; $C_{1-6}$alkyl; $C_{1-6}$alkyloxy; $C_{1-6}$alkylthio; $C_{1-6}$alkyloxycarbonyl; polyhalo$C_{1-6}$alkyl-O— or polyhalo$C_{1-6}$alkyl;

$R^2$ each independently represents halo; hydroxy; amino; cyano; mono- or di($C_{1-6}$alkyl)amino; $C_{1-6}$alkyl; HO—$C_{1-6}$alkyl-; amino-$C_{1-6}$alkyl-; HO—C(=O)—$C_{1-6}$alkyl-; polyhalo$C_{1-6}$alkyl; $C_{1-6}$alkyl-O—; $C_{1-6}$alkylthio; $C_{1-6}$alkyl-O—C(=O)—; aminocarbonyl; polyhalo$C_{1-6}$alkyl-O— or $C_{1-6}$alkyl-C(=O)—NH—;

Z is; $C_{1-6}$alkyl-C(=O)—NH—$C_{1-4}$alkyl-;
 $C_{3-6}$cycloalkyl-C(=O)—NH—$C_{1-4}$alkyl-; formylamino-$C_{1-4}$alkyl-; Ar$^4$—$C_{1-4}$alkyl-; $R^xR^yN$—C(=O)—$C_{1-4}$alkyl-;
 $C_{1-6}$alkyl-O—$C_{1-6}$alkyl; $C_{1-6}$alkyl-C(=O)—NH—$C_{1-6}$alkyl; $C_{1-6}$alkyl-S(=O)$_2$—NH—$C_{1-6}$alkyl;
 Het$^5$-C(=O)—NH—$C_{1-6}$alkyl; Ar$^5$—C(=O)—NH—$C_{1-6}$alkyl or Z represents $C_{1-6}$alkyloxy-C(=O)—$C_{2-4}$alkyl-;

Het$^5$ represents isoxazolyl or pyridyl wherein each of said ring systems may optionally be substituted with up to 3 substituents, each substituent independently being selected from halo or $C_{1-6}$alkyl;

Ar$^4$ represents phenyl optionally substituted with halo, $C_{1-6}$alkyl, $C_{1-6}$alkyloxy, polyhalo$C_{1-6}$alkyloxy or polyhalo$C_{1-6}$alkyl;

Ar$^5$ represents phenyl optionally substituted with halo, $C_{1-6}$alkyl, $C_{1-6}$alkyloxy, polyhalo$C_{1-6}$alkyloxy or polyhalo$C_{1-6}$alkyl;

$R^x$ and $R^y$ each independently represent hydrogen, $C_{1-6}$alkyl, $C_{1-6}$alkyl-O—$C_{1-6}$alkyl or $R^x$ and $R^y$ taken together with the N atom to which they are attached form a 5 or 6 membered heterocycle selected from pyrrolidinyl, thiomorpholinyl, piperidinyl or morpholinyl.

2. A compound according to claim 1 wherein;
n is 0, 1, 2, 3 or 4;
m is 0, 1, 2, 3 or 4;

$R^1$ each independently represents halo; hydroxy; $C_{1-6}$alkyl; $C_{1-6}$alkyloxy; $C_{1-6}$alkylthio; $C_{1-6}$alkyloxycarbonyl; polyhalo$C_{1-6}$alkyl-O— or polyhalo$C_{1-6}$alkyl;

$R^2$ each independently represents, halo; hydroxy; amino; cyano; mono- or di($C_{1-6}$alkyl)amino; $C_{1-6}$alkyl; HO—$C_{1-6}$alkyl-; amino-$C_{1-6}$alkyl-; HO—C(=O)—$C_{1-6}$alkyl-; polyhalo$C_{1-6}$alkyl; $C_{1-6}$alkyl-O—; $C_{1-6}$alkylthio; $C_{1-6}$alkyl-O—C(=O)—; aminocarbonyl; polyhalo$C_{1-6}$alkyl-O— or $C_{1-6}$alkyl-C(=O)—NH—;

Z is; $C_{1-6}$alkyl-C(=O)—NH—$C_{1-4}$alkyl-;
 $C_{3-6}$cycloalkyl-C(=O)—NH—$C_{1-4}$alkyl-; formylamino-$C_{1-4}$alkyl-; Ar$^4$—$C_{1-4}$alkyl-; $R^xR^yN$—C(=O)—$C_{1-4}$alkyl-; or Z represents $C_{1-6}$alkyloxy-C(=O)—$C_{2-4}$alkyl-;

Ar$^4$ represents phenyl optionally substituted with halo, $C_{1-6}$alkyl, $C_{1-6}$alkyloxy or polyhalo$C_{1-6}$alkyl;

$R^x$ and $R^y$ each independently represent hydrogen, $C_{1-6}$alkyl or $R^x$ and $R^y$ taken together with the N atom to which they are attached form a 5 or 6 membered heterocycle selected from pyrrolidinyl, thiomorpholinyl, piperidinyl or morpholinyl.

3. A pharmaceutical composition comprising a pharmaceutically acceptable carrier and as active ingredient a therapeutically effective amount of a compound as claimed in claim 1 or 2.

4. A process of preparing a composition as claimed in claim 3 characterized in that a pharmaceutically acceptable carrier is intimately mixed with a therapeutically effective amount of a compound as claimed claim 1 or 2.

* * * * *